(12) United States Patent
Lorenz et al.

(10) Patent No.: US 11,839,689 B2
(45) Date of Patent: *Dec. 12, 2023

(54) FORMULATIONS OF ENZALUTAMIDE

(71) Applicants: Astellas Pharma Inc., Tokyo (JP); Medivation Prostate Therapeutics LLC, New York, NY (US)

(72) Inventors: Douglas Alan Lorenz, Bend, OR (US); Sanjay Konagurthu, Bend, OR (US); Randy J. Wald, Bend, OR (US); Jason A. Everett, Bend, OR (US); Sheila Matz, North Conway, NH (US); Yuuki Takaishi, Tokyo (JP); Toshiro Sakai, Tokyo (JP); Ryousuke Irie, Tokyo (JP); Shinsuke Oba, Tokyo (JP); Hiroyasu Toyota, Tokyo (JP); Koji Nishimura, Tokyo (JP); Atsushi Kanbayashi, Tokyo (JP)

(73) Assignees: Astellas Pharma Inc., Tokyo (JP); Medivation Prostate Therapeutics LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/985,235

(22) Filed: Nov. 11, 2022

(65) Prior Publication Data
US 2023/0210778 A1    Jul. 6, 2023

Related U.S. Application Data

(63) Continuation of application No. 17/662,278, filed on May 6, 2022, now abandoned, which is a continuation
(Continued)

(51) Int. Cl.
*A61K 9/20* (2006.01)
*C07D 233/86* (2006.01)
(Continued)

(52) U.S. Cl.
CPC .............. *A61K 9/2054* (2013.01); *A61K 9/10* (2013.01); *A61K 9/16* (2013.01); *A61K 9/1652* (2013.01);
(Continued)

(58) Field of Classification Search
CPC ................................ A61K 9/2054; A61K 9/10
See application file for complete search history.

(56) References Cited

U.S. PATENT DOCUMENTS 6,899,899 B2    5/2005  Takagi et al.
7,189,415 B2    3/2007  Takagi et al.
(Continued)

FOREIGN PATENT DOCUMENTS

EP    0901786 A2    3/1999
EP    0901786 B1    3/1999
(Continued)

OTHER PUBLICATIONS

Center of Drug Evaluation and Research, Clinical Pharmacology and Biopharmaceutics Review. (Year: 2012).*
(Continued)

*Primary Examiner* — Carlos A Azpuru
(74) *Attorney, Agent, or Firm* — Banner & Witcoff, Ltd.

(57) ABSTRACT

This disclosure provides formulations of enzalutamide and their use for treating hyperproliferative disorders.

7 Claims, 9 Drawing Sheets

Related U.S. Application Data of application No. 17/487,546, filed on Sep. 28, 2021, now abandoned, which is a continuation of application No. 17/178,580, filed on Feb. 18, 2021, now abandoned, which is a continuation of application No. 16/924,656, filed on Jul. 9, 2020, now abandoned, which is a continuation of application No. 16/693,655, filed on Nov. 25, 2019, now abandoned, which is a continuation of application No. 16/044,255, filed on Jul. 24, 2018, now abandoned, which is a continuation of application No. 15/267,352, filed on Sep. 16, 2016, now abandoned, which is a continuation of application No. 14/023,878, filed on Sep. 11, 2013, now abandoned.

(60) Provisional application No. 61/699,351, filed on Sep. 11, 2012.

(51) Int. Cl.
  A61K 9/10 (2006.01)
  A61K 31/4166 (2006.01)
  A61K 47/32 (2006.01)
  A61K 47/38 (2006.01)
  A61K 9/16 (2006.01)
  A61K 31/4164 (2006.01)

(52) U.S. Cl.
  CPC ........ *A61K 9/2095* (2013.01); *A61K 31/4164* (2013.01); *A61K 31/4166* (2013.01); *A61K 47/32* (2013.01); *A61K 47/38* (2013.01); *C07D 233/86* (2013.01)

(56) References Cited

U.S. PATENT DOCUMENTS

| | | | |
|---|---|---|---|
| 7,709,517 B2 | 5/2010 | Sawyers et al. | |
| 7,780,988 B2 | 8/2010 | Beyerinck et al. | |
| 8,183,274 B2 | 5/2012 | Sawyers et al. | |
| 8,445,507 B2 | 5/2013 | Jung et al. | |
| 2001/0053778 A1 | 12/2001 | Hoover et al. | |
| 2002/0009494 A1* | 1/2002 | Curatolo | A61K 9/1652 |
| | | | 424/489 |
| 2002/0031547 A1 | 3/2002 | Takagi et al. | |
| 2004/0074350 A1 | 4/2004 | Hanada | |
| 2005/0038111 A1 | 2/2005 | Bateman et al. | |
| 2006/0079706 A1 | 4/2006 | Parthasaradhi et al. | |
| 2007/0004753 A1 | 1/2007 | Sawyers et al. | |
| 2008/0181960 A1 | 7/2008 | Doney | |
| 2010/0297194 A1 | 11/2010 | Catron et al. | |
| 2010/0310659 A1 | 12/2010 | Desai et al. | |
| 2011/0020455 A1 | 1/2011 | Yoshida et al. | |
| 2014/0100256 A1 | 4/2014 | Lorenz et al. | |
| 2014/0179749 A1 | 6/2014 | Lorenz et al. | |
| 2014/0378517 A1 | 12/2014 | Lorenz et al. | |
| 2015/0216813 A1 | 8/2015 | Everett et al. | |
| 2015/0239848 A1 | 8/2015 | Peddy et al. | |
| 2017/0027910 A1 | 2/2017 | Lorenz et al. | |
| 2017/0224624 A1 | 8/2017 | Lorenz et al. | |
| 2017/0267645 A1 | 9/2017 | Peddy et al. | |
| 2022/0347102 A1 | 11/2022 | Fradera Gelabert et al. | |

FOREIGN PATENT DOCUMENTS

| | | | |
|---|---|---|---|
| EP | 1368001 B1 | 10/2005 | |
| EP | 1741424 A1 | 1/2007 | |
| EP | 1741424 A2 | 1/2007 | |
| EP | 1893196 B1 | 3/2008 | |
| EP | 1893196 B2 | 7/2015 | |
| EP | 1741424 B1 | 10/2018 | |
| EP | 3725778 A1 | 10/2020 | |
| EP | 3735778 B1 | 11/2020 | |
| EP | 3725778 B1 | 8/2021 | |
| EP | 3971167 A1 | 3/2022 | |
| WO | 200109143 A1 | 2/2001 | |
| WO | 2002067893 A2 | 9/2002 | |
| WO | 2003032950 A1 | 4/2003 | |
| WO | 2003033508 A1 | 4/2003 | |
| WO | 2003043606 A1 | 5/2003 | |
| WO | 2003063821 A2 | 8/2003 | |
| WO | 2003089499 A1 | 10/2003 | |
| WO | 2004074350 A2 | 9/2004 | |
| WO | 2006123223 A1 | 11/2006 | |
| WO | 2006124118 A1 | 11/2006 | |
| WO | 2007016435 A2 | 2/2007 | |
| WO | 2008110534 A1 | 9/2008 | |
| WO | 2010114928 A2 | 10/2010 | |
| WO | 2011106570 A1 | 9/2011 | |
| WO | 2011112558 A2 | 9/2011 | |
| WO | 2013184681 A1 | 12/2013 | |
| WO | 2014042945 A1 | 3/2014 | |
| WO | 2014043208 A1 * | 3/2014 | |
| WO | 2014167428 A2 | 10/2014 | |
| WO | 2018199282 A1 | 11/2018 | |

OTHER PUBLICATIONS

Singh, Spray drying formulation of amorphous solid dispersions, Advanced Drug Delivery Reviews, 100 , 27-50 (Year: 2016).*
Guo et al, A Comparative Study on In Vivo Characteristics of Enzalutamide Nanocrystals Versus Amorphous Solid Dispersions and a Better Prediction for Bioavailability Based on the "Spring Parachute" Model, International Journal of Pharmaceuticals (628) (Year: 2022).*
Fryer et al., "Physical Properties and Effect in a Battery of Safety Pharmacology Models for Three Structurally Distinct Enteric Polymers Employed as Spray-Dried Dispersions Carriers, " Frontiers in Pharmacology 7, 12 pages Oct. 13, 2016.
Gao & Shi, "Characterization of Supersaturatable Formulations for Improved Absorption of Poorly Soluble Drugs," The AAPS Journal 14, 703-13, 2012.
Ghadi & Dand, "BCS class IV drugs: Highly notorious candidates for formulation development," J. Controlled Release 248, 71-95, 2017.
Guedes et al., "Solid Dispersions of Imidazolidinedione by PEG and PVP Polymers with Potential Antischistosomal Activities," AAPS PharmSciTech 12, 401-10, 2011.
Gupta et al., "Formulation Strategies to Improve the Bioavailability of Poorly Absorbed Drugs with Special Emphasis on Self-Emulsifying Systems," ISRN Pharmaceutics 2013, 16 pages.
Hamm Wittkopp, Opposition to EP3725778 filed May 18, 2022.
Harris, "Solid Dispersions. A universal formulation strategy for poorly soluble drugs?" available at www.contractpharma.com/issues/2016-04-01/view_features/solid-dispersions-a-universal-formulation-strategy-for-poorly-soluble-drugs, 8 pages, Apr. 5, 2016.
Holm et al., "Bile salts and their importance for drug absorption," Int. J. Pharmaceutics 453, 44-55, available online Apr. 15, 2013.
Hong, "Solid Molecular Dispersions of Itraconazole for Enhanced Dissolution and Controlled Drug Delivery," Thesis submitted to Graduate Department of Pharmaceutical Sciences, University of Toronto, 2009, 92 pages.
Huang & Dai, "Fundamental aspects of solid dispersion technology for poorly soluble drugs," Acta Pharmaceutica Sinica B 4, 18-25, 2014.
Hugo, "Selection of excipient, solvent and packaging to optimize the performance of spray-dried formulations," Drug Development and Industrial Pharmacy 39, 402-12, 2012.
International Search Report and Written Opinion for PCT/US2013/059223, dated Dec. 20, 2013, 9 pages.
Janssens and Van den Mooter, "Review: physical chemistry of solid dispersions," J. Pharmacy Pharmacology 61, 1571-86, 2009.
Kalepu & Nekkanti, "Insoluble drug delivery strategies: review of recent advances and business prospects," Acta Pharmaceutica Sinica B 5, 422-53, 2015.
Kalepu et al., "Oral lipid-based drug delivery systems—an overview," Acta Pharmaceutica Sinica B 3(6):361-72, 2013.

(56) References Cited

OTHER PUBLICATIONS

Kaushal & Bansal, "Thermodynamic behavior of glassy state of structurally related compounds," Eur. J. Pharmaceutics Biopharmaceutics 69, 1067-76, 2008.

Kawabata et al., "Novel crystalline solid dispersion of tranilast with high photostability and improved oral bioavailability," European Journal of Pharmaceutical Sciences 39, 256-62, 2010.

Kennedy et al.; "Enhanced Bioavailability of a Poorly Soluble VR1 Antagonist Using an Amorphous Solid Dispersion Approach: A Case Study"; 2008; Molecular Pharmaceutics; 5(6): 981-993.

Kollipara & Ghandi, "Pharmacokinetic aspects and in vitro-in vivo correlation potential for lipid-based formulations," Acta Pharmaceutica Sinica B 4, 333-49, 2014.

Kumar & Singh, "A Study on Solubility Enhancement Methods for Poorly Water Soluble Drugs," Am. J. Pharmacol. Sci. 1, 67-73, 2013.

Kurkov & Loftsson, "Cyclodextrins," Int. J. Pharmaceutics 453, 167-80, available online Jul. 5, 2012.

LaFountaine et al., "Challenges and Strategies in Thermal Processing of Amorpous Solid Dispersions: A Review," AAPS PharmSciTech 17, 43-55. 2016.

Laitinen et al., "Emerging trends in the stabilization of amorphous drugs," Int. J. Pharmaceutics 453, 65-79, available online Apr. 28, 2012.

Lauer et al., "Atomic Force Microscopy-Based Screening of Drug-Excipient Miscibility and Stability of Solid Dispersions," Pharm. Res. 28, 572-84, 2011.

Lauer et al., "Rapid Assessment of Homogeneity and Stability of Amorphous Solid Disperions by Atomic Force Microscopy—From Bench to Batch," Pharm. Res. 30, 2010-22, 2013.

Leuner et al., "Improving drug solubility for oral delivery using solid dispersions," European Journal of Pharmaceutics and Biopharmaceutics 50, 47-60, 2000.

Lin and Wong, "Predicting Oral Drug Absorption: Mini Review on Physiologically-Based Pharmacokinetic Models," Pharmaceutics 9, 41, 2017, 14 pages.

Lissy et al., "Pharmacokinetic comparison of an oral diclofenac potassium liquid-filled soft gelatin capsule with a diclofenac potassium tablet," Expert Opinion on Pharmacotherapy 11:5, 701-08, 2010.

Loftsson, Preface for the special IJP issue "Poorly soluble drugs," Int. J. Pharmaceutics 453, 1-2, available online Jun. 3, 2013.

Lorenz et al., EP 13766437.1, response filed Aug. 25, 2017.

Lorenz et al., EP1376647.1, Examination Report dated Oct. 2, 2019.

Lorenz et al., U.S. Appl. No. 14/023,637 claims filed Dec. 24, 2013.

Lorenz et al., U.S. Appl. No. 14/023,878, claims filed Mar. 3, 2014, 3 pages.

Lorenz et al., U.S. Appl. No. 14/023,878, response filed Dec. 2, 2015, 17 pages.

Variankaval et al., "From Form to Function: Crystallization of Active Pharmaceutical Ingredients," AIChE Journal 54, 1682-88, 2008.

Vasconcelos et al., "Solid dispersions as a strategy to improve oral bioavailability of poor water soluble drugs," Drug Discovery Today 12, 1068-75, 2007.

Verma & Rudraraju, "Wetting Kinetics: an Alternative Approach Towards Understanding the Enhanced Dissolution rate for Amorphous Solid Dispersion of a Poorly Soluble Drug," AAPS PharmSciTech 16, 1079-90, 2015.

Vialpando et al., "Evaluation of Three Amorphous Drug Delivery Technologies to Improve the Oral Absorption of Flubendazole," J. Pharmaceutical Sciences 105, 2782-93, 2016.

Warren et al., "Using polymeric precipitation inhibitors to improve the absorption of poorly water-soluble drugs: A mechanistic basis for utility," Journal of Drug Targeting 18, 704-31, 2010.

Wen et al., "Drug Delivery Approaches in Addressing Clinical Pharmacology-Related Issues: Opportunities and Challenges," The AAPS Journal 17, 1327-40, 2015.

Wenglowsky et al., "Pyrazolopyridine Inhibitors of B-RafV600E. Part 1: The Development of Selective, Orally Bioavailable, and Efficacious Inhibitors," ACS Med. Chem. Lett. 2, 342-47, 2011.

Wilson et al., "Bioavailability Comparison of Various Amorphous Solid Dispersion Formulations of Enzalutamide," poster, 1 page, 2016 AAPS meeting.

Woo et al., "Reduced food-effect and enhanced bioavailability of a self-microemulsifying formulation of itraconazole in healthy volunteers," Eur. J. Pharm. Sci. 33, 159-65, 2008.

Xtandi® prescribing information (Europe), Aug. 2012, 3 pages.

Xtandi® prescribing information (JP), Feb. 2018 with translation.

Xtandi® prescribing information (US), Aug. 2012, 16 pages.

Xtandi® prescribing information (US), Aug. 2020, 34 pages.

Xtandi® prescribing information (US), Oct. 2020, 28 pages.

Xu & Dai, "Drug precipitation inhibitors in supersaturable formulations," Int. J. Pharmaceutics 453, 26-43, available online May 13, 2013.

Xu et al., "Mesoporous systems for poorly soluble drugs," Int. J. Pharmaceutics 453, 181-97, available online Sep. 8, 2012.

Yasir et al., "Biopharmaceutical Classification System: An Account," Int. J. PharmTech Res. 2, 1681-90, 2010.

Yu et al., "Molecular Interaction Studies of Amorphous Solid Dispersions of the Antimelanoma Agent Betulinic Acid," AAPS PharmSciTech 16, 384-97, 2015.

Zentiva, k.s., Opposition to EP3725778 filed May 13, 2022.

Zheng et al., "Selection of oral bioavailability enhancing formulations during drug discovery," Drug Development and Industrial Pharmacy 38, 235-47, 2012.

Peddy et al., U.S. Appl. No. 15/611,486, preliminary amendment, dated Jun. 1, 2017, 4 pages.

Peddy et al., U.S. Appl. No. 15/611,486, response to non-final office action, dated Jan. 18, 2018, 6 pages.

Peddy et al., U.S. Appl. No. 15/611,486, response to Restriction Requirement filed Aug. 23, 2017, 5 pages.

Pingali et al., "Mixing order of glidant and lubricant—Influence on powder and tablet properties," Int. J. Pharm. 409, 269-77, 2011.

Pre-Grant Opposition filed against 2875/DELNP/2015, dated Jul. 7, 2019, 31 pages.

Puri et al., "Investigation of Atypical Dissolution Behavior of an Encapsulated Amorphous Solid Dispersion," J. Pharm. Sci. 100, 2460-68, 2011.

Qian et al., "Drug-Polymer Solubility and Miscibility: Stability Consideration and Practical Challenges in Amorphous Solid Dispersion Development," J. Pharm. Sci. 99, 2941-2947, 2010.

Raijada et al., "A high throughput platform for understanding the influence of excipients on physical and chemical stability," Int. J. Pharmaceutics 453, 285-92, available online Aug. 24, 2012.

Ray, "Excipient Update: Addressing Challenges With Low-Solubility Compounds: The Importance of Functional Excipients in the Formulation of Amorphous Dispersions," available at drug-dev.com/excipient-update-addressing-challenges-with-low-solubility-compounds-the-importance-of-functional-excipients-in-the-formulation-of-amorphous-dispersions/, posted Oct. 2012.

Reymond, "Oval pill coated tablets easier to swallow", Oct. 31, 2006.

Rodriguez-Vida et al., "Enzalutamide for the treatment of metastatic castration-resistant prostate cancer," Drug Design, Development and Therapy 9, 3325-39, 2015.

Rumondor & Taylor, "Effect of Polymer Hygroscopicity on the Phase Behavior of Amorphous Solid Dispersions in the Presence of Moisture," Mol. Pharmaceutics 7, 477-90, 2009.

Rumondor et al., "Understanding the Tendency of Amorphous Solid Dispersions to Undergo Amorphous-Amorphous Phase Separation in the Presence of Absorbed Moisture," APS PharmSciTech 12, 1209-19, 2011.

Samy, "Class II drugs; a dissolution/bioavailability challenge: Flutamide-loaded spray dried lactose for dissolution control," Int. J. Drug Dev. & Res. 4, 195-203, 2012.

Savla et al., "Review and analysis of FDA approved drugs using lipid-based formulations," Drug Development and Industrial Pharmacy 43, 1743-58, 2017.

Savla, "Bringing Poorly Soluble Molecules to Market with Bioavailability Enhancement Technologies," available at

(56) References Cited

OTHER PUBLICATIONS americanpharmaceuticalreview.com/Featured-Articles/188660-Bringing-Poorly-Soluble-Molecules-to-Market-with-Bioavailability-Enhancement-Technologies/, 9 pages, posted Jun. 15, 2016.
Savla, "Softgel Formulations—Lipid-Based Drug Delivery System to Bring Poorly Soluble Drugs to Market," available at drug-dev.com/softgel-formulations-lipid-based-drug-delivery-system-to-bring-poorly-soluble-drugs-to-market/, 5 pages, posted Aug. 30, 2016.
Sawicki et al., "Inventory of Oral Anticancer Agents: Pharmaceutical Formulation Aspects with Focus on the Solid Dispersion Technique," Cancer Treatment Reviews 50, 247-63, 2016.
Sawicki et al., "Validation of a liquid chromatographic method for the pharmaceutical; quality control of products containing elacridar," Journal of Pharmaceutical Analysis 2016; 6(4): 268-275.
Sawicki, "Solid dispersions in oncology: a solution to solubility-limited oral drug absorption," Thesis, Utrecht University Depository, 2017, 229 pages.
Scher et al., "Increased Survival with Enzalutamide in Prostate Cancer after Chemotherapy," N. Eng. J. Med. 367, 1187-97, Aug. 15, 2012.
Scher et al., Trial Protocol for Scher et al., "Increased Survival with Enzalutamide in Prostate Cancer after Chemotherapy," N. Eng. J. Med. 367, 1187-97, Aug. 15, 2012.
Sethia & Squillante, "Solid Dispersions: Revival with Greater Possibilities and Applications in Oral Drug Delivery," Critical Review in Therapeutic Drug Carrier Systems 20, 215-47, 2003.
Shah et al., "Approaches for Improving Bioavailability of Poorly Soluble Drugs," Chapter 2 in Pharmaceutical Dosage Forms—Tablets. Rational Design and Formulation, Augsburger & Hoag, eds., 3rd ed., CRC Press, Boca Raton, 2008, 54 pages.
Shah et al., "Melt extrusion with poorly soluble drugs," Int. J. Pharmaceutics 453, 233-52, available online Nov. 20, 2012.
Siepmann & Siepmann, "Mathematical modeling of drug dissolution," Int. J. Pharmaceutics 453, 12-24, available online Apr. 22, 2013.
Sigurdsson et al., "Mucus as a barrier to lipophilic drugs," Int. J. Pharmaceutics 453, 56-64, available online May 29, 2013.
Sim et al., "Characterization and pharmacokinetic study of itraconazole solid dispersions prepared by solvent-controlled precipitation and spray-dry methods," J. Pharmacy and Pharmacology 69, 1707-15, 2017.
Sinha et al., "Bottom-up approaches for preparing drug nanocrystals: Formulations and factors affecting particle size," Int. J. Pharmaceutics 453, 126-41, available online Jan. 18, 2013.
Sotthivirat et al., "Development of amorphous solid dispersion formulations of a poorly water-soluble drug, MK-0364," Int. J. Pharmaceutics 452, 73-81, 2013.
Stada Arzneimittel AG, Opposition to EP3725778 filed May 18, 2022.
Stewart et al., "Impact of Drug-Rich Colloids of Itraconazole and HPMCAS on Membrane Flux in Vitro and Oral Bioavailability in rats," Molecular Pharmaceutics 14, 2437-49, 2017.
Synthon BV, Opposition to EP3725778 filed May 18, 2022.
Talukder et al., "Dissolution and Solid-State Characterization of Poorly Water-Soluble Drugs in the Presence of a Hydrophilic Carrier," AAPS PharmSciTech 12, 1227-33, 2011.
Tanno et al., "Evaluation of Hypromellose Acetate Succinate (HPMCAS) as a Carrier in Solid Dispersions," Drug Development and Industrial Pharmacy 30, 9-17, 2004.
Taylor, "Probing the Precipitation Behavior of Poorly Water Soluble Compounds," Purdue University, retrieved at zerista.s3.amazonaws.com/item_files/edaf/attachments/413306/original/75_01.pdf, no date provided.
Teja et al., "Drug-excipient behavior in polymeric amorphous solid dispersions," J. Excipients and Food Chem. 4, 70-94, 2013.
Teva Pharmaceutical Industries Ltd., Opposition to Patent 237604 in Israel, May 18, 2022.
Thakuria et al., "Pharmaceutical cocrystals and poorly soluble drugs," Int. J. Pharmaceutics 453, 101-25, available online Dec. 1, 2012.
Third Party Observations filed in EP 13766437.1, Jun. 17, 2019, 11 pages.
Third Party Observations filed in EP 13766437.1, Jun. 17, 2019, 5 pages.
Third Party Observations filed in Lorenz, EP20177837.0, Apr. 15, 2021.
Ting et al., "Deconstructing HPMCAS: Excipient Design to Tailor Polymer-Drug Interactions for Oral Drug Delivery," ACS Biomater. Sci. Eng. 1, 978-90, 2015.
University of Colorado Denver, "Enzalutamide adds five months survival in late-stage prostate cancer," available at www.sciencedaily.com/releases/2012/08/12816101035.htm, 3 pages, Aug. 16, 2012.
Accord Healthcare Limited, Opposition to EP3725778 filed May 18, 2022.
Al-Obaidi & Buckton, "Evaluation of Griseofulvin Binary and Ternary Solid Dispersions with HPMCAS," AAPS PharmSciTech 10, 1172-77, 2009.
Alfred E. Tiefenbacher (GmbH & Co. KG), Opposition to EP3725778 filed May 18, 2022.
Ali et al., "The role of lipid geometry in designing liposomes for the solubilisation of poorly water soluble drugs," Int. J. Pharmaceutics 453, 225-32, available online Jul. 3, 2012.
Ambike et al., "Stability study of amophrous valdecoxib," Int. J. Pharmaceutics 282, 151-62, 2004.
Andrews et al., "Physicochemical Characterization of Hot Melt Extruded Bicalutamide-Polyvinylpyrrolidone Solid Dispersions," J. Pharmaceut. Sci. 99, 1322-35, 2010.
Anonymous, "A Study to Compare Capsule and Tablet Forms of MDV3100 (Enzalutamide) After Administration of a Single Set Dose Under Fasted Conditions in Healthy Male Subjects," ClinicalTrials.gov identifier NCT01911741, Jul. 30, 2013.
Anonymous, "Enzalutamide and difficulty swallowing the capsules," available at databankws.lareb.nl/Downloads/Signals_2016_Enzalutamidedysphagia.pdf, 2 pages, 2016.
Anonymous, Excerpt from the National Drug Code Directory for Xtandi dated Mar. 31, 2022.
Anonymous, Press Release, "U.S. FDA Approves Xtandi® (enzalutamide) After Priority Review for Patients With Metastatic Castration-Resistant Prostate Cancer Previously Treated with Docetaxel," Astellas.com, Sep. 1, 2012.
Aulton, ed., Pharmaceutics, The Science of Dosage Form Design, 2nd Ed., p. 241, 2002.
Baghel et al., "Polymeric Amorphous Solid Dispersions: A Review of Amorphization, Crystallization, Stabilization, Solid-State Characterization, and Aqueous Solubilization of Biopharmaceutical Classification System Class II Drugs," J. Pharmaceut. Sci. 105, 2527-44, 2016.
Bend Research, "Spray Drying of Amorphous Dispersions," Pharmaceutical Technology Europe 24(9), 3 pages, Sep. 2, 2012.
Beringer, et al., Eds.; "Remington: The Science and Practice of Pharmacy; 21st Ed."; 2005; Lippencott, Williams & Wilkins; pp. 229-230, 675-676, 730.
Bevernage et al., "Evaluation of gastrointestinal drug supersaturation and precipitation: Strategies and issues," Int. J. Pharmaceutics 453, 25-35, available online Nov. 27, 2012.
Bevernage et al., "Excipient-Mediated Supersaturation Stabilization in Human Intestinal Fluids," Molecular Pharmaceutics 8, 564-70, Jan. 26, 2011.
Bhatnagar et al., "Solid Dispersion in Pharmaceutical Drug Development: From Basics to Clinical Applications," Current Drug Delivery 10, 2013, 17 pages.
Broadbent & Bennette, "Fundamentals of Spray-Dried Dispersion Technology," 2015.
Brough & Williams, "Amorphous solid dispersions and nanocrystal technologies for poorly water-soluble drug delivery," Int. J. Pharmaceutics 453, 157-66, available online Jun. 7, 2013.
Buelle, Opposition to EP3725778 filed May 18, 2022.
Byrn et al., "Pharmaceutical Solids: A Strategic Approach to Regulatory Considerations," Pharmaceutical Research 12, 945-54, 1995.
Calahan et al.; "Isothermal Microcalorimetry to Investigate the Phase Separation for Amorphous Solid Dispersions of AMG 517 with HPMC-AS"; Apr. 2013; Mol. Pharmaceutics 2013, 10, 1949-1957.

(56) References Cited

OTHER PUBLICATIONS

Calahan, Characterization of Amorphous Solid Dispersions of AMG 517 in HMPC-AS and crystallization using sothermal Microcalorimetry, Apr. 4, 2011, pp. 1-128.
Cantarini et al., "Pharmacokinetics of Two Novel Bicalutamide Formulations in Healthy Male Volunteers," Pharmacology 77, 171-78, 2006.
Censi & Di Martino, "Polymorph Impact on the Bioavailability and Stability of Poorly Soluble Drugs," Molecules 20, 18759-76, 2015.
Center of Drug Evaluation and Research, Clinical Pharmacology and Biopharmaceutics Review, submitted May 22, 2012, not publicly available before Aug. 31, 2012, pp. 1-83.
Chiang et al., "Evaluation of Drug Load and Polymer by Using a 96-Well Plate Vacuum Dry System for Aorphous Solid Dispersion Drug Delivery," AAPS PharmSciTech 13, 713-22, available online May 5, 2012.
Chiang et al., "In Vitro and In Vivo Evaluation of Amorphous Solid Dispersions Generated by Different Bench-Scale Processes, Using Griseofulvin as a Model Compound," The AAPS Journal 15, 608-17, available online Mar. 2, 2013.
Chokshi et al., "Improving the Dissolution Rate of Poorly Water Soluble Drug by Solid Dispersion and Solid Solution—Pros and Cons," Drug Delivery 14, 33-45, 2008.
Clegg et al.; "ARN-509: A Novel Antiandrogen for Prostate Cancer Treatment"; Jan. 2012; Cancer Res; 72(6): 1494-1503 & Supplemental pp. 1-13.
Curatolo et al., "Utility of Hydroxypropylmethylcellulose Acetate Succinate (HPMCAS) for Initiation and Maintenance of Drug Supersaturation in the GI Milieu," Pharm Res. 26, 1419-31, 2009.
Davis et al., "Amorphous solid dispersions of BCS class II drugs: A rational approach to solvent and polymer selection," Chemical Engineering Research and Design 110, 192-99, 2016.
Domingos et al., "New forms of old drugs: improving without changing," J. Pharmacy and Pharmacology 67, 830-46, 2015.
Dong & Choi, "Hydroxypropyl Methylcellulose Acetate Succinate: Potential Drug-Excipient Incompatibility," AAPS PharmSciTech 9, 991-97, 2008.
Drug Bank Entry for Enzalutamide, available at https://www.drugbank.ca/drugs/DB08899, 9 pages, created on Jun. 4, 2013.
Drugs.com, "Silicon Dioxide", available online Oct. 29, 2011.
Edueno et al., "The Need for Restructuring the Disordered Science of Amorphous Drug Formulations," Pharm. Res. 34, 1754-72, 2017.
Elder et al., "Aqueous solubility: Simple predictive methods (in silico, in vitro and bio-relevant approaches)," Int. J. Pharmaceutics 453, 3-11, available online Nov. 2, 2012.
Elder et al., "Use of pharmaceutical salts and cocrystals to address the issue of poor solubility," Int. J. Pharmaceutics 453, 88-100, available online Nov. 24, 2012.
Environmental Protection Agency, "The Presidential Green Chemistry Challenge Awards Program: Summary of 2009 Award Entries and Recipients," pp. 1-47, 2009.
Environmental Protection Agency, "The Presidential Green Chemistry Challenge Awards Program: Summary of 2010 Award Entries and Recipients," pp. 1-47, 2010.
EP 20177837.0, "Information about non-relevance of third-party observations," Examiner's statement dated Apr. 9, 2021.
FDA Draft Guidance for Industry, Bioavailability and Bioequivalence Studies Submitted in NDAs or INDs—General Considerations, Mar. 2014, 83 pages.
FDA Draft Guidance on Enzalutamide, Jun. 2015, 2 pages.
FDA Guidance for Industry: Bioavailability and Bioequivalence Studies for Orally Administered Drug Products—General Considerations, 2002, 27 pages.
Ferrari et al., "The Surface Roughness of Lactose Particles Can be Modulated by Wet-Smoothing Using a High-Shear Mixer," AAPS PharmSciTech 5, 1-6, 2004.
Friesen et al., "Hydroxypropyl Methylcellulose Acetate Succinate-Based Spray-Dried Dispersions: An Overview," Molecular Pharmaceutics 5, 1003-19, available online Dec. 1, 2008.
Center for Drug Evaluation and Research, Multi-Discipline Review for Xtandi® Tablets, Jan. 25, 2021.
Clinical Pharmacology and Biopharmaceutics Review portion of the Xtandi® capsules FDA approval package, Sep. 12, 2012.
Cordes et al.,, "Study to Compare Capsule and Liquid Formulations of Enzalutamide After Single-Dose Administration Under Fasting Conditions in Prostate Cancer," The Oncologist 26(9), 729-e1493, 2021.
Grohganz et al., "Amorphous drugs and dosage forms," J. Drug Del. Sci. Tech. 23, 403-08, 2013.
Guo et al., "Physical stability of pharmaceutical formulations: solid-state characterization of amorphous dispersions," Trends in Analytical Chem. 49, 137-44, 2013.
Int. J. Pharmaceutics 453, Table of Contents, https://www.sciencedirect.com/journal/international-journal-of-pharmaceutics/vol/453/issue/1, 2013.
Kawahara et al., "Changing the enzalutamide form from a capsule to a tablet improves the adherence of medicine Intake: A case of a significant decrease in the prostate-specific antigen level and improvement in radiographic findings," IJU Case Reports 2, 143-45, 2019.
Lorenz et al., EP 20 177 837.0, EPO Preliminary Opinion, dated Mar. 29, 2023.
Lorenz et al., EP 22197255.7 Search Report and Opinion, dated Mar. 3, 2023, 12 pages.
Lu & Park, "Polymeric micelles and alternative nanonized delivery vehicles for poorly water soluble drugs," Int. J. Pharmaceutics 453, 198-214, 2013.
Mahlin & Bergstrom, "Early drug development predictions of glass-forming ability and physical stability of drugs," Eur. J. Pharm. Sci. 49, 323-32, 2013.
Mohanachandran, "Superdisintegrants: An Overview," Int. J. Pharm. Sci. Rev. & Res. 6(1), 105-09, 2011.
Ninomiya et al., "Preference for enzalutamide capsules versus tablet pills in patients with prostate cancer," Int. J. Urology 26(12), 1161-62, 2019.
Novo et al., "Designing synergistic crystallization inhibitors: Bile salt derivatives of cellulose with enhanced hydrophilicity," Carbohydrate Polymers 292, 119680, 1-10, 2022.
Panini et al., "Myth or Truth: The Glass Forming Ability Class II Drugs Will Always Form Single-Phase Homogenous Amorphous Solid Dispersion Formulations," Pharmaceutics 11, 529, 2019 (17 pages).
Schittny et al., "Mechanism of increased bioavailability through amorphous solid dispersions: a review," Drug Delivery 27, 110-27, 2019.
Singh et al., "Oral formulation strategies to improve solubility of poorly water-soluble drugs," Expert Opin. Drug Deliv. 3, 1361-78, 2011.
Sun et al., "Stability of Amorphous Pharmaceutical Solids: Crystal Growth Mechanisms and Effect of Polymer Additives," The AAPS Journal 14, 380-88, 2012.
Van den Mooter, "The use of amorphous solid dispersions: A formulation strategy to overcome poor solubility and dissolution rate," Drug Discovery Today: Technologies 9, e79-e85, 2012.
Van Eerdenbrugh & Taylor, "Small Scale Screening to Determine the Ability of Different Polymers to Inhibit Drug Crystallization Upon Rapid Solvent Evaporation," Molecular Pharmaceutics 7(4), 1328-37, 2010.
Van Eerdenbrugh et al., "Crystallization Tendency of Active Pharmaceutical Ingredients Following Rapid Solvent Evaporation—Classification and Comparison with Crystallization Tendency from Undercooled Melts," J. Pharm. Sci. 99, 3826-38, 2010.
Wen et al., "Drug Delivery Approaches in Addressing Clinical Pharmacology-Related Issues: Opportunities and Challenges," The AAPS Journal 17, 1327-40, Nov. 2015.
Lorenz et al., U.S. Appl. No. 15/267,352 Preliminary Amendment filed Mar. 27, 2019.
Lorenz et al., U.S. Appl. No. 15/267,352 response filed Dec. 1, 2017.
Lorenz et al., U.S. Appl. No. 15/268,352 Nonfinal Office Action dated May 28, 2019.
Lorenz et al., U.S. Appl. No. 17/985,220 Nonfinal Office Action dated Mar. 13, 2023.

(56) References Cited

OTHER PUBLICATIONS

Lorenz et al., U.S. Appl. No. 17/985,235, filed Nov. 11, 2022.
Lu & Park, "Polymeric micelles and alternative nanonized delivery vehicles for poorly soluble drugs," Int. J. Pharmaceutics 453, 198-214, available online Aug. 25, 2012.
Lu & Rohani, "Polymorphism and Crystallization of Active Pharmaceutical Ingredients (APIs)," Current Medicinal Chemistry 16, 884-905, 2009.
Löbmann et al., "A theoretical and spectroscopic study of co-amorphous naproxen and indomethacin," Int. J. Pharmaceutics 453, 80-87, available online 18, 2012.
Mahmoudi et al., "In Vitro Characterization of a Novel Polymeric System for Preparation of Amorphous Solid Drug Dispersions," The AAPS Journal 16, 685-97, 2014.
Manitpisitkul et al., "Bioavailability and Pharmacokinetics of TRPV1 Antagonist Mavatrep (JNJ-39438335) Tablet and Capsule Formulations in Healthy Men: Two Open-Label, Crossover, Single-Dose Phase 1 Studies," Clin. Pharmacol. Drug Dev. 7, 2017, abstract, 2 pages.
Midha et al., "Solid Dispersion: A Recent Update," Int. J. Pharmacol. 1, 17 pages, 2017.
Morgen et al., "Polymeric nanoparticles for Increased Oral Bioavailability and Rapid Absorption Using Celecoxib as a Model of a Low-Solubility, High-Permeability Drug," Pharm. Res. 29, 427-40, 2012.
Mu et al., "Lipid-based formulations for oral administration of poorly water-soluble drugs," Int. J. Pharmaceutics 453, 215-24, available online Apr. 8, 2013.
Möschwitzer et al., "Drug nanocrystals in the commercial pharmaceutical development process," Int. J. Pharmaceutics 153, 142-56, available online Sep. 21, 2012.
Newman et al., "Assessing the Performance of Amorphous Solid Dispersions," J. Pharmaceut. Sci. 101, 1355-77, 2012.
Newman, ed., Pharmaceutical Amorphous Solid Dispersions, Wiley, 2015.
Othman et al., "A Phase 1 Study to Evaluate the Bioavailability and Food Effect of 2 Solid-Dispersion Formulations of the TRPV1 Antagonist ABT-102, Relative to the Oral Solution Formulation, in Healthy Human Volunteers," Clin. Pharmacol. Drug Dev. 1, 24-31, 2012.
Pamu et al., "Formulation and In Vitro Evaluation of Gastroretentive Floating Drug Delivery of Valsartan Using Hot Melt Extrusion Technique," International Journal of Pharmaceutical Sciences and Research 8, 1813-19, 2017.
Patel et al., "Revealing facts behind spray dried solid dispersion technology used for solubility enhance,ment," Saudi Pharmaceutical Journal 23, 352-65, 2015.
Paudel et al., "Manufacturing of solid dispersions of poorly water soluble drugs by spray drying: Formulation and process considerations," Int. J. Pharmaceutics 453, 253-84, available online Jul. 20, 2012.
Peddy et al., U.S. Appl. No. 15/611,486, final rejection, dated May 17, 2018, 13 pages.
Peddy et al., U.S. Appl. No. 15/611,486, non-final Office Action dated Sep. 18, 2017, 9 pages.
Center for Drug Evaluation & Research, Product Quality Review for Xtandi® Tablet NDA 213674, 2020.
Invalidation Action filed for Taiwan Patent No. I673051 reported by Taiwan Intellectual Property Office dated May 12, 2023, with English translation of Part 1.
Labrasol Technical Data Sheet, May 26, 2020.
Lorenz et al., U.S. Appl. No. 17/985,220, Declaration of John J. Koleng, Jr., Ph.D. Under 37 C.F.R. § 1.132 filed on Jun. 13, 2023.
Lorenz et al., U.S. Appl. No. 17/985,220, Declaration of Toshiro Sakai, Ph.D. Under 37 C.F.R. § 1.132 filed on Jun. 13, 2023.
Lorenz et al., U.S. Appl. No. 17/985,220, Exhibits 1-10 to Koleng Declaration filed Jun. 13, 2023.
Lorenz et al., U.S. Appl. No. 17/985,220, Exhibits 11-20 to Koleng Declaration filed Jun. 13, 2023.
Lorenz et al., U.S. Appl. No. 17/985,220, Exhibits 21-33 to Koleng Declaration filed Jun. 13, 2023.
Lorenz et al., U.S. Appl. No. 17/985,220, Exhibits 1-5 to Sakai Declaration filed Jun. 13, 2023.
Lorenz et al., U.S. Appl. No. 17/985,220, Exhibits 6-8 to Sakai Declaration filed Jun. 13, 2023.
Lorenz et al., U.S. Appl. No. 17/985,220, Interview Request, dated Apr. 28, 2023.
Lorenz et al., U.S. Appl. No. 17/985,220, Interview Summary, dated May 23, 2023.
Lorenz et al., U.S. Appl. No. 17/985,220, Response to Non-Final Office Action filed on Jun. 13, 2023.
Xtandi® prescribing information (US), Sep. 9, 2022, 16 pages.
Lorenz et al., U.S. Appl. No. 16/371,618 response filed Mar. 22, 2021.
Lorenz et al., U.S. Appl. No. 16/371,618 response filed Sep. 28, 2021.
Lorenz et al., U.S. Appl. No. 16/371,618 response filed Sep. 8, 2020.
Lorenz et al., U.S. Appl. No. 16/371,618, Non-final Office Action dated Mar. 9, 2020.
Lorenz et al., U.S. Appl. No. 16/371,618, Preliminary Amendment filed Nov. 14, 2019.
Lorenz et al., U.S. Appl. No. 17/178,580, filed Feb. 18, 2021.
Lorenz et al., U.S. Appl. No. 17/985,220, filed Nov. 11, 2022.
Lorenz et al., U.S. Appl. No. 61/699,351, filed Sep. 11, 2012.
Maiwald Patentanwalts, Opposition to EP3725778 filed May 18, 2022.
Miller et al.; "A Win-Win Solution in Oral Delivery of Lipophilic Drugs: Supersaturation via Amorphous Solid Dispersions Increases Apparent Solubility without Sacrifice of Intestinal Membrane Permeability"; Feb. 2012; Mol. Pharmaceutics; 9: 2009-2016.
Newman, ed., Pharmaceutical Amorphous Solid Dispersions, Wiley, 2015, 505 pages.
Ray, "Bioavailability Enhancement—Addressing Solubility Challenges: Using Effective Technology & Problem-Solving for Delivery Solutions," Drug Development and Delivery, Jul./Aug. 2012.
Ritschel & Bauer-Brandl eds., Die Tablette, Handbuch der Entwicklung, Herstellung und Qualitaetssicherung, p. 582.
Rowe et al., eds., Handbook of Pharmaceutical Excipients, pp. 377-380, revised Mar. 1, 2012.
Sandoz AG, Opposition to EP3725778 filed May 11, 2022.
Srinarong, "Improved dissolution behavior of lipophilic drugs by solid dispersions," University of Groningen research database, published 2011, 153 pages.
Vasconcelos et al., "Amorphous solid dispersions: Rational selection of a manufacturing process," Advanced Drug Delivery Reviews 100, 85-101, 2016.
Alhalaweh et al., "Physical stability of drugs after storage above and below the glass transition temperature: Relationship to glass-forming ability," Int. J. Pharm. 495, 312-17, 2015.
Edueng et al., "Long-Term Physical (In)Stability of Spray-Dried Amorphous Drugs: Relationship with Glass-Forming Ability and Physicochemical Properties," Pharmaceutics 11, 20 pages, 2019.
First Examination Report, 2875/DELNP/2015, dated Aug. 21, 2018, 6 pages.
Gibson, "Pharmaceutical Preformulation and Formulation. A Practical Guide from Candidate Drug Selection to Commercial Dosage Form," Interpharm/CRC, vol. 199, 2nd ed., preface, contents, contributors, and chapters 4 and 11, 2009, 119 pages.
Hadida, Case History: Kalydeco (VX-770, Ivacaftor), a CTFR Potentiator for the Treatment of Patients with Cystic Fibrosis and the G551D-CTFR Mutation, Annual Reports in Medicinal Chemistry 49, 383-98, 2014.
Invalidation Action filed for Taiwan Patent No. 1673051 reported by Taiwan Intellectual Property Office dated May 12, 2023, including English translation.
Kwong, "Discovery and development of telaprevir: an NS3-4A protease inhibitor for treating genotype 1 chronic hepatitis C virus," Nature Biotechnology 29, 993-1003, 2011.
Lorenz et al., EP13766437.1 filed Apr. 1, 2015, 99 pages.
Lorenz et al., EP13766437.1 response including claims filed May 22, 2019, 10 pages.

(56) References Cited

OTHER PUBLICATIONS

Lorenz et al., EP13766437.1, Application Deemed Withdrawn, Jun. 26, 2020, 2 pages.
Lorenz et al., EP13766437.1, Communication from Examining Division, dated Nov. 14, 2018, 4 pages.
Lorenz et al., EP13766437.1, Examiner's communication, dated Feb. 16, 2017, 4 pages.
Lorenz et al., EP13766437.1, Response filed Aug. 25, 2017, 8 pages.
Lorenz et al., EP13766437.1, Response to Written Opinion filed Oct. 28, 2015, 5 pages.
Lorenz et al., EP13766437.1, Statement of Non-Relevance of Third Party Observations dated Mar. 15, 2021.
Lorenz et al., EP20177837 as filed Jun. 2, 2020, 102 pages.
Lorenz et al., EP20177837 response to oppositions filed Dec. 12, 2022, 79 pages.
Lorenz et al., EP20177837 Search Opinion, dated Sep. 17, 2020, 2 pages.
Lorenz et al., EP20177837, Intent to Grant and Examiner's Response to Third Party Observations, Mar. 2, 2021, 8 pages.
Lorenz et al., EP21190086.5, Search Opinion, dated Feb. 1, 2022, 6 pages.
Lorenz et al., IL237604, Petition to Amend Claims dated Nov. 16, 2022 with English translation, 10 pages.
Lorenz et al., U.S. Appl. No. 17/985,220, Response to Non-Final Office Action, dated Jun. 13, 2023, 27 pages.
Medivation Press Release dated Aug. 31, 2012, 4 pages.
Patil et al., "Solid-state characterization and dissolution properties of bicalutamide-beta-cyclodextrin inclusion complex," Pharmazie 63, 282-85, 2008.
Public Assessment Report (EPAR) of Xtandi® dated Apr. 25, 2013, 86 pages.
Qui et al., "Developing solid oral dosage forms: pharmaceutical theory and practice," Academic Press (Elsevier), 1st edition, pp. 46, 48, 53, and 54, 2009.
Response to First Examination Report, 2875/DELNP/2015, dated May 20, 2019, 45 pages.
Romanova et al., "Amorphous Enzalutamide—Non-isothermal recrystallization kinetics and thermal stability," Thermochimica Acta 665, 134-41, 2018.
Rumondor et al., "Effects of Polymer Type and Storage Relative Humidity on the Kinetics of Felodipine Crystallization from Amorphous Solid Dispersions," Pharmaceutical Research 26, pp. 2599-2606, Dec. 2009.
Schittny et al., "Particle Forming Amorphous Solid Dispersions: A Mechanistic Randomized Pharmacokinetic Study in Humans," Pharmaceutics 13, 401, 2021, 16 pages.
Shah et al., "Improved Human Bioavailability of Vemurafenib, a Practically Insoluble Drug, Using an Amorphous Polymer-Stabilized Solid Dispersion Prepared by a Solvent-Controlled Coprecipitation Process," Journal of Pharmaceutical Sciences 102, 967-81, 2013.
Sharma, Pre-Grant Opposition to IN 2875/DELNP/2015 filed Dec. 24, 2021, 24 pages, exhibits submitted separately.
Shreya, Pre-Grant Opposition to IN 2875/DELNP/2015 filed Jul. 5, 2019, 335 pages including exhibits.
Singh & Van den Mooter, "Spray drying formulation of amorphous solid dispersions," Advanced Drug Delivery Reviews 100, 27-50, 2016.
Srinarong et al., "Improved dissolution behavior of lipophilic drugs by solid dispersions: the production process as starting point for formulation considerations" (review article), Expert Opin. Drug Deliv. 8, 1121-40, 2012.
Stewart et al., "Practical Approach to Modeling the Impact of Amorphous Drug Nanoparticles on the Oral Absorption of Poorly Soluble Drugs," Mol. Pharmaceutics 17, 180-89, 2020.
Summary of Product Characteristics (SmPC) of Xtandi® associated with marketing authorization dated Jun. 21, 2013, 85 pages.
Summary of Studies (D49) submitted with Proprietors' Response to Opppositions to EP3725778, dated Dec. 12, 2022, 10 pages.
Swarbrick, ed., Encyclopedia of Pharmaceutical Technology, Informa Healthcare USA, Inc., 2007 (3rd edition, vol. 1), contributors, contents, preface, and pp. 19-45 and 1242-1265.
Synthon BV, Writ of Summons, Revocation of EP 3725778B1 in Italy filed Jul. 6, 2023, with English machine translation, 103 pages.
Synthon BV, Writ of Summons, Revocation of EP 3725778B1 in The Netherlands filed Jun. 13, 2023, Dutch and Japanese and English translations, 160 pages.
Taylor, "Physical Stability and Crystallization Inhibition," Chapter 5 of Pharmaceutical Amorphous Solid Dispersions, first edition, Newman, ed., John Wiley & Sons, Inc., pp. 179-217, 2015.
Teva Pharmaceutical Industries Ltd., Opposition to Patent 237604 in Israel, Amended Statement dated Jun. 22, 2023, Hebrew with English translation.
Third Party Observations filed in Lorenz EP20177837.0, dated Nov. 2, 2020, 11 pages.
Third Party Observations filed in Lorenz EP20177837.0, dated Nov. 4, 2020, 2 pages.
Third Party Observations filed in Lorenz, EP20177837.0, Mar. 25, 2021.
Williams et al., "Formulating Poorly Water Soluble Drugs," American Association of Pharmaceutical Scientsts/Springer, Advances in Pharmaceutical Sciences Series 3, 2012, preface, contents, contributors, and chapters 2 and 3, 2012, 117 pages.
Wilson et al., "Amorphous solid dispersions of enzalutamide and novel polysaccharide derivatives: investigation of relationships between polymer structure and performance," Nature Research Scientific Reports 10, 18535, 2020, 12 pages.
Wilson et al., "Interaction of Polymers with Enzalutamide Nanodroplets—Impact on Droplet Properties and Induction Times," Mol. Pharmaceutics 18, 836-49, 2021.
Center for Drug Evaluation & Research, Product Quality Review for Xtandi® Tablet NDA 213674.
DiNunzio et al., "Production of advanced solid dispersions for enhanced bioavailability of itraconazole using KinetiSol® Dispersing," Drug Development and Industrial Pharmacy 36, 1064-78, Nov. 5, 2010.
Dr. Schoen Neymeyr & Partner, Opposition to EP3725778 filed May 17, 2022.
Drugs@FDA, NDA 213674, https://www.accessdata.fda.gov/scripts/cder/daf/index.cfm?event=overview.process&ApplNo=213674.
Elkington + Fife, Opposition to EP3725778 filed May 18, 2022.
Environmental Protection Agency, "The Presidential Green Chemistry Challenge Awards Program: Summary of 2009 Award Entries and Recipients," 71 pages, 2009.
Environmental Protection Agency, "The Presidential Green Chemistry Challenge Awards Program: Summary of 2010 Award Entries and Recipients," 58 pages, 2010.
Gao, "Amorphous Pharmaceutical Solids: Characterization, Stabilization, and Development of Marketale Formulations of Poorly Soluble Drugs with Improved Oral Absorption," Molecular Pharmaceutics 5, 903-04, 2008.
Ghosh et al., "Comparison of HPMC based polymers performance as carriers for manufacture of solid dispersions using the melt extruder," International Journal of Pharmaceutics 419, 12-19, 2011.
Hamm Wittkopp, Opposition to EP3725778 filed May 17, 2022.
Konno & Taylor, "Ability of Different Polymers to Inhibit the Crystallization of Amorphous Felodipine in the Presence of Moisture," Pharmaceutical Research 25, 969-78, 2007.
Konno et al., "Effect of polymer type on the dissolution profile of amorphous solid dispersions containing felodipine," Eur. J. Pharmaceutics Biopharmaceutics 70, 493-99, 2008.
Kumar et al., "Development and Optimization of Enzalutamide-Loaded Solid Lipid Nanoparticles Using Box-Behnken Design," Asian Journal of Pharmaceutical and Clinical Research 12, 67-76, 2019.
Lorenz et al., EP 13766437.1 Examination Report—Examiner's Statement of Relevance of Third Party Observations, dated Oct. 2, 2019, 3 pages.
Lorenz et al., EP 20177837.0, "Information about non-relevance of third-party observations," Examiner's statement dated Apr. 15, 2021.

(56) References Cited

OTHER PUBLICATIONS

Lorenz et al., EP 3725778 Provisional Opinion, dated Mar. 29, 2023.
Lorenz et al., U.S. Appl. No. 14/023,637 claims filed Sep. 11, 2013.
Lorenz et al., U.S. Appl. No. 14/023,637 non-final Office Action dated Mar. 10, 2014.
Lorenz et al., U.S. Appl. No. 14/023,637 Response to Notice to File Corrected Application Papers, including substitute specification and drawings with claims filed Dec. 24, 2013.
Lorenz et al., U.S. Appl. No. 14/023,878, claims filed Sep. 11, 2013.
Lorenz et al., U.S. Appl. No. 14/023,878, final Office Action dated Mar. 17, 2016.
Lorenz et al., U.S. Appl. No. 14/023,878, Non-Final Office Action dated Jun. 2, 2015.
Lorenz et al., U.S. Appl. No. 14/023,878, response filed Dec. 2, 2015.
Lorenz et al., U.S. Appl. No. 14/023,878, Restriction Requirement dated Dec. 1, 2014.
Lorenz et al., U.S. Appl. No. 14/023,878, Preliminary Amendment and Response to Notice to File Corrected Application Papers, including substitute specification with claims filed Mar. 3, 2014.
Lorenz et al., U.S. Appl. No. 14/481,986 claims filed Sep. 10, 2014.
Lorenz et al., U.S. Appl. No. 14/481,986, Final Office Action dated Sep. 9, 2015.
Lorenz et al., U.S. Appl. No. 14/481,986, non-final Office Action dated Feb. 25, 2015.
Lorenz et al., U.S. Appl. No. 14/481,986, response filed Jul. 27, 2015.
Lorenz et al., U.S. Appl. No. 15/018,078, claims filed Feb. 8, 2016.
Lorenz et al., U.S. Appl. No. 15/018,078, final office action, dated Aug. 21, 2017.
Lorenz et al., U.S. Appl. No. 15/018,078, interview summary dated Sep. 19, 2018.
Lorenz et al., U.S. Appl. No. 15/018,078, non-final Office Action dated Apr. 2, 2018.
Lorenz et al., U.S. Appl. No. 15/018,078, non-final Office Action dated Nov. 25, 2016.
Lorenz et al., U.S. Appl. No. 15/018,078, response filed Feb. 21, 2018.
Lorenz et al., U.S. Appl. No. 15/018,078, response filed May 25, 2017.
Lorenz et al., U.S. Appl. No. 15/267,352 Preliminary Amendment and Response to Restriction Requirement filed Dec. 1, 2017.
Lorenz et al., U.S. Appl. No. 15/267,352 restriction requirement dated Jun. 12, 2017.
Lorenz et al., U.S. Appl. No. 15/267,352, application filed Sep. 16, 2016.
Lorenz et al., U.S. Appl. No. 15/267,352, non-final Office Action dated Jan. 25, 2018.
Lorenz et al., U.S. Appl. No. 15/267,352, preliminary amendment filed May 1, 2017.
Lorenz et al., U.S. Appl. No. 16/044,255 preliminary amendment filed Mar. 27, 2019.
Lorenz et al., U.S. Appl. No. 16/044,255, filed Jul. 24, 2018.
Lorenz et al., U.S. Appl. No. 16/044,255, Office Action dated May 28, 2019.
Lorenz et al., U.S. Appl. No. 16/371,618 claims filed Apr. 1, 2019.
Lorenz et al., U.S. Appl. No. 16/371,618 final Office Action dated Nov. 10, 2021.
Lorenz et al., U.S. Appl. No. 16/371,618 final Office Action dated Sep. 21, 2020.
Lorenz et al., U.S. Appl. No. 16/371,618 Koleng Declaration filed Mar. 22, 2021.
Lorenz et al., U.S. Appl. No. 16/371,618 non-final Office Action dated Mar. 29, 2021.
Wilson et al., "Relationship between amorphous solid dispersion in vivo absorption and in vitro dissolution: phase behavior during dissolution, speciation, and membrane mass transport," Journal of Controlled Release 292, 172-82, 2018.

Xtandi® Drug Approval Package webpage printout for Xtandi® capsules (date created Sep. 12, 2012).
Xtandi® Drug Approval Package webpage printout for Xtandi® tablets, Jan. 25, 2021.
Amended Claims filed Aug. 21, 2023 in Invalidation Action Against TW Patent 1673051, including English translation, 4 pages.
Center for Drug Evaluation and Research, Index for Approval Package and Approval Letter for Xtandi® capsules dated Aug. 31, 2012, not publicly available before Sep. 12, 2012, 10 pages.
Guo et al., "A comparative study on in vitro and in vivo characteristics of enzalutamide nanocrystals versus amorphous solid dispersions and a better prediction for bioavailability based on 'spring-parachute' model," International Journal of Pharmaceutics 628, 122333, 2022, 14 pages.
Incivek®, US Prescribing Information, May 2011, 23 pages.
Jannin et al., "Approaches for the development of solid and semi-solid lipid-based formulations," Advanced Drug Delivery Reviews 60, 734-46, 2008.
Joshi et al., "Bioavailability enhancement of a poorly water-soluble drug by solid dispersion in polyethylene glycol-polysorbate 80 mixture," International Journal of Pharmaceutics 269, 251-58, 2004.
Kalydecor, US Prescribing Information, Feb. 2017, 17 pages.
Kambayashi & Dressman, "Towards Virtual Bioequivalence Studies for Oral Dosage Forms Containing Poorly Water-Soluble Drugs: A Physiologically Based Biopharmaceutics Modeling (PBBM) Approach," Journal of Pharmaceutical Sciences 111, 135-45-2022.
Lorenz et al., EP22197255.7 Claims filed Dec. 15, 2022, 3 pages.
Lorenz et al., EP22197225.7 Search Report and Opinion, dated Mar. 3, 2023, 12 pages.
Lorenz et al., EP20177837 Search Report, dated Sep. 8, 2020, 3 pages.
Lorenz et al., EP21190086.5 Claims filed Oct. 21, 2021, 2 pages.
Lorenz et al., IL237604 Response to Opposition filed Sep. 26, 2023, Hebrew and English translation, 31 pages.
Lorenz et al., IL237604, Amended Claims filed Mar. 8, 2015, 3 pages.
Lorenz et al., IL237604, First Office Action, English translation, dated Oct. 24, 2017, 4 pages.
Lorenz et al., IL237604, Notice of Acceptance and Allowed Claims in English, dated Apr. 8, 2021, 4 pages.
Lorenz et al., IL237604, Response to First Office Action in English, dated May 24, 2018, 89 pages.
Lorenz et al., IL237604, Response to Second Office Action with English translation, dated May 30, 2019, 9 pages.
Lorenz et al., IL237604, Response to Third Office Action with English translation, dated Oct. 26, 2020, 7 pages.
Lorenz et al., IL237604, Second Office Action, English translation, dated Jan. 31, 2019, 2 pages.
Lorenz et al., IL237604, Third Office Action, with English translation, dated Feb. 27, 2020, 6 pages.
Lorenz et al., U.S. Appl. No. 14/023,637 claims filed Sep. 11, 2013, 1 page.
Lorenz et al., U.S. Appl. No. 14/481,986 claims filed Sep. 10, 2014, 1 page.
Lorenz et al., U.S. Appl. No. 16/371,618, application filed, Apr. 1, 2019, 100 pages.
Lorenz et al., U.S. Appl. No. 17/985,220 nonfinal Office Action dated Jul. 17, 2023, 16 pages.
Lorenz et al., U.S. Appl. No. 17/985,220 response to nonfinal Office Action filed Sep. 15, 2023, 10 pages.
Lorenz et al., U.S. Appl. No. 17/985,220 Terminal Disclaimer and Approval, Sep. 15, 2023, 3 pages.
Lorenz et al., TW102132800, Allowance with English Translation, Jun. 11, 2019, 3 pages.
Lorenz et al., TW102132800, Amended Claims with English Translation, Aug. 29, 2018, 4 pages.
Lorenz et al., TW102132800, Amended Claims with English Translation, Jun. 23, 2017, 6 pages.
Lorenz et al., TW102132800, Amended Claims with English Translation, Sep. 8, 2016, 6 pages.
Lorenz et al., TW102132800, Application for Amendment and Response, dated Jun. 23, 2017, 7 pages.

(56) References Cited

OTHER PUBLICATIONS

Lorenz et al., TW102132800, Application for Amendment, Re-Examination, and Response, dated Aug. 29, 2018, 10 pages.

Lorenz et al., TW102132800, Decision of Rejection with English Translation, dated Dec. 28, 2017, 7 pages.

Lorenz et al., TW102132800, Office Action with English Translation, dated Dec. 22, 2016, 16 pages.

Marsac et al., "A Comparison of the Physical Stability of Amorphous Felodipine and Nifedipine Systems," Pharmaceutical Research 23, 2306-16, 2006.

Medivation Press Release, "Medivation's MDV3100 Shown to be Effective in a Preclinical Model of Hormone-Refractory Prostate Cancer," Feb. 26, 2007, 2 pages.

Patentee's Response to Invalidation Action Against TW Patent 1673051, including English translation, dated Aug. 21, 2023, 135 pages.

Perrie & Rades, "Themed issue: Improve dissolution, solubility and bioavailability of poorly soluble drugs," Journal of Pharmacy and Pharmacology 62, 1517-18, 2010.

Xtandi® European Medicines Agency package leaflet for tablets, last revised Oct. 2018, 6 pages.

Xtandi® European Medicines Agency Summary of Product Characteristics of tablets, updated Jul. 2019, 20 pages.

Zelboraf®, US Prescribing Information, Apr. 2017, 21 pages.

FDA list of 2012 approval notifications, dated Feb. 13, 2018, 2 pages.

\* cited by examiner

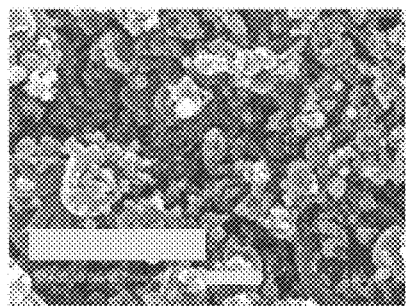
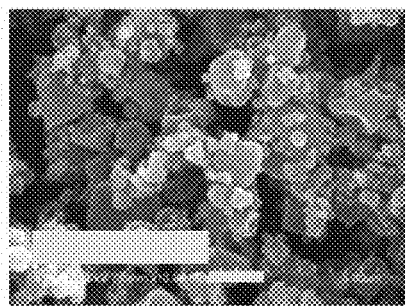
FIG. 2A INITIAL  
FIG. 2B 1 DAY 50°C/75% RH  
60%A:HPMCAS-MG DISPERSION D6
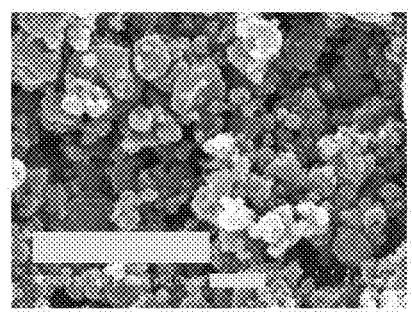
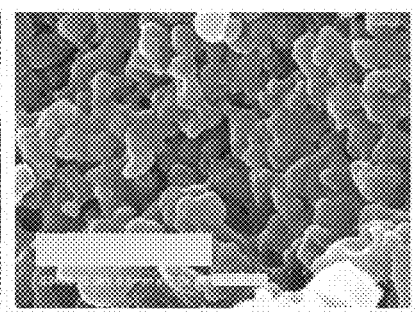
FIG. 2C INITIAL  
FIG. 2D 1 DAY 50°C/75% RH  
80%A:HPMCAS-MG DISPERSION D7

FIG. 2E 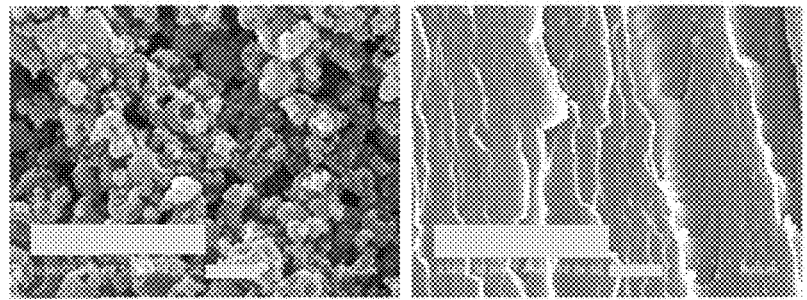 FIG. 2F
INITIAL     1 DAY 50°C/75% RH
40%A:PVPVA
DISPERSION D10
FIG. 2G 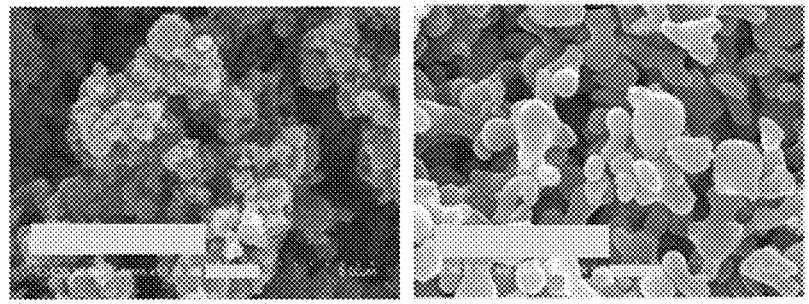 FIG. 2H
INITIAL     1 DAY 50°C/75% RH
100% SPRAY DRIED
AMORPHOUS MDV3100

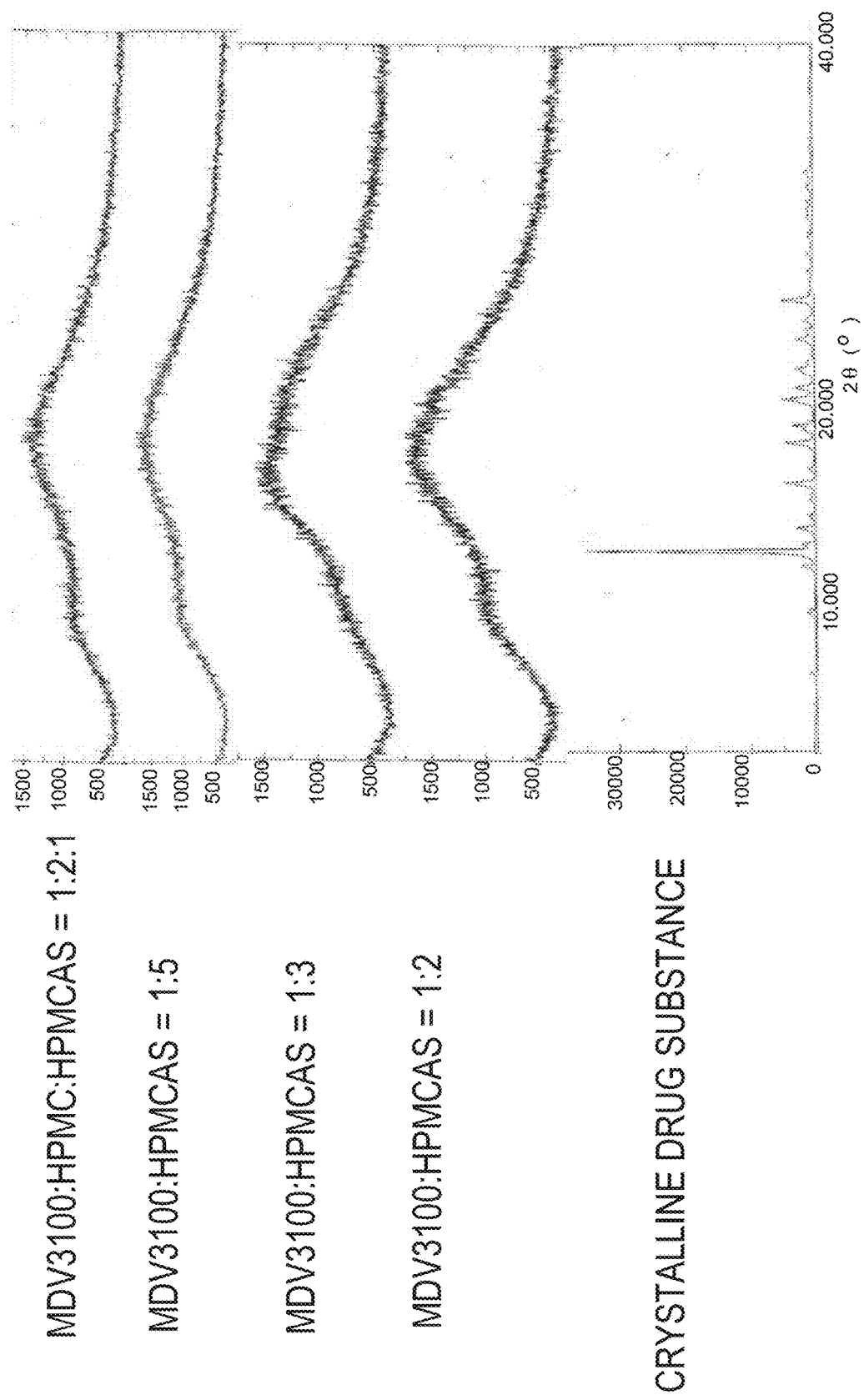

FORMULATIONS OF ENZALUTAMIDE

FORMULATIONS OF ENZALUTAMIDE

This application is a continuation of Ser. No. 17/662,278 filed on May 6, 2022, which is a continuation of Ser. No. 17/487,546 filed on Sep. 28, 2021, which is a continuation of Ser. No. 17/178,580 filed on Feb. 18, 2021, which is a continuation of Ser. No. 16/924,656 filed on Jul. 9, 2020, which is a continuation of Ser. No. 16/693,655 filed on Nov. 25, 2019, which is a continuation of Ser. No. 16/044,255 filed on Jul. 24, 2018, which is a continuation of Ser. No. 15/267,352 filed on Sep. 16, 2016, now abandoned, which is a continuation of Ser. No. 14/023,878 filed on Sep. 11, 2013, now abandoned, which claims priority to and incorporates by reference Ser. No. 61/699,351 filed on Sep. 11, 2012.

All documents cited in this disclosure are incorporated herein by reference in their entireties.

TECHNICAL FIELD

This disclosure relates to solid formulations of enzalutamide.

BRIEF DESCRIPTION OF THE DRAWINGS

FIGS. 2A-H. Scanning Electron Micrograph (SEM) images of amorphous enzalutamide (100% A Spray-dried) and spray-dried dispersions (SDDs) comprising enzalutamide and HPMCAS or PVPVA. FIG. 2A, 60% A:HPMCAS-MG Dispersion D6 before exposure to a 50° C./75% RH environment. FIG. 2B, 60% A:HPMCAS-MG Dispersion D6 after 1 day exposure to a environment. FIG. 2C, 80% A:HPMCAS-MG Dispersion D7 before exposure to a environment. FIG. 2D, 80% A:HPMCAS-MG Dispersion D7 after 1 day exposure to a 50° C./75% RH environment. FIG. 2E, 40% A:PVPVA Dispersion D10 before exposure to a environment. FIG. 2F, 40% A:PVPVA Dispersion D10 after 1 day exposure to a environment. FIG. 2G, 100% spray dried amorphous MDV3100 before exposure to a 50° C./75% RH environment. FIG. 2H, 100% spray dried amorphous MDV3100 after 1 day exposure to a 50° C./75% RH environment. See Example 6.

FIG. 6 is an X-ray diffraction spectrum of the solid dispersions prepared in Example 16 (1:3), 18 (1:2), and crystalline drug substance obtained by measuring it immediately after its preparation.

DETAILED DESCRIPTION

Figure 1:
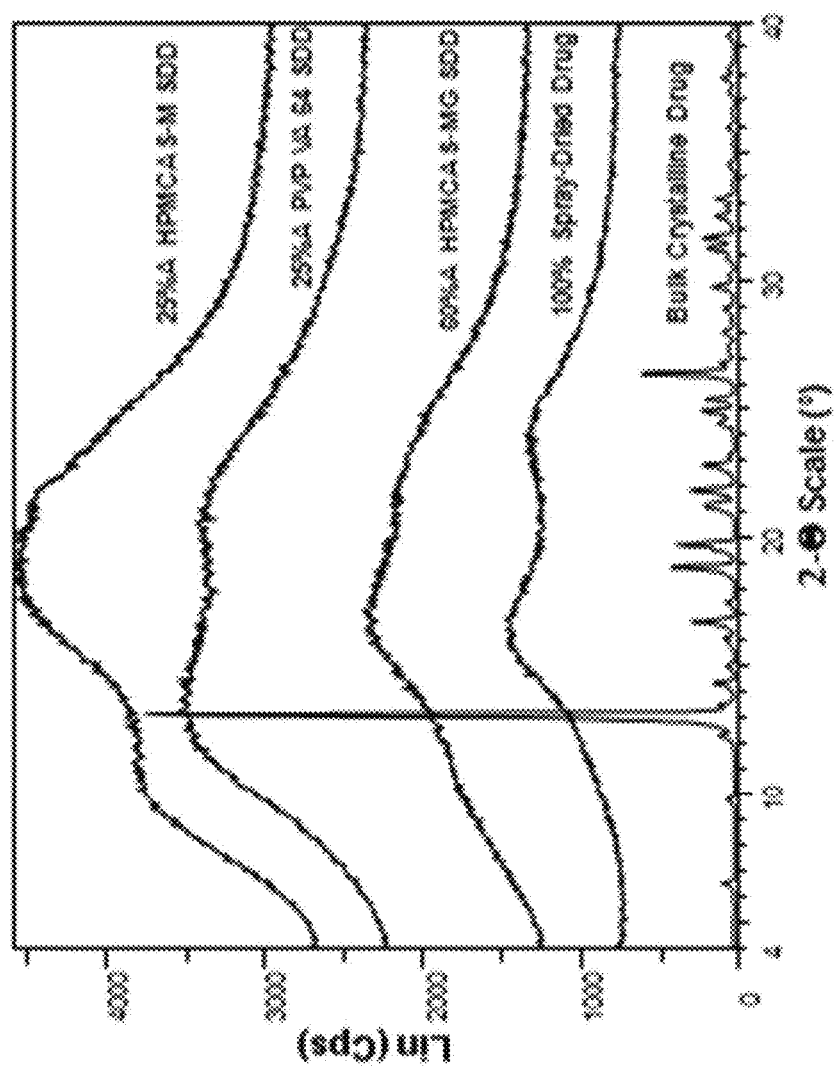
FIG. 1. PXRD Diffractograms of amorphous enzalutamide, three spray-dried dispersions of enzalutamide with concentration-enhancing polymers, and crystalline enzalutamide. See Example 3.

Enzalutamide is an androgen receptor signaling inhibitor. The chemical name is 4-{3-[4-cyano-3-(trifluoromethyl) phenyl]-5,5-dimethyl-4-oxo-2-sulfanylideneimidazolidin-1-yl}-2-fluoro-N-methylbenzamide. The structural formula is:

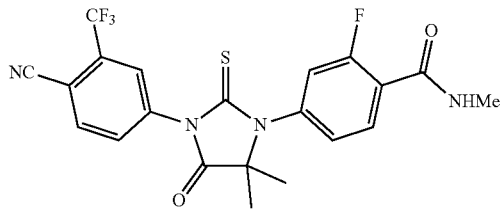 [SMILES: CNC(=O)c1ccc(N2C(=S)N(c3ccc(C#N)c(C(F)(F)F)c3)C(=O)C2(C)C)cc1F]

Enzalutamide is used as an agent for treating castration-resistant prostate cancer who have received docetaxel therapy; enzalutamide also is disclosed for treating breast cancer, prostate cancer, benign prostate hyperplasia and ovarian cancer; See, e.g., U.S. Pat. No. 7,709,517.

The present disclosure provides a solid dispersion having the properties such as improvement solubility and absorption of enzalutamide, and a pharmaceutical composition containing the solid dispersion which has dissolution stability.

Further, the present disclosure provides a method for making pharmaceutical composition which has dissolution stability of enzalutamide.

According to the present disclosure, (1) a pharmaceutical composition which improves solubility and absorption of enzalutamide, (2) a pharmaceutical composition which has rapid disintegrating property and dispersibility of enzalutamide when said pharmaceutical composition (tablet and the like) is used, and (3) a process of manufacturing the pharmaceutical composition which has said effect, can be provided.

These dosage forms provide unusually large enhancements in aqueous concentration in an environment of use. These compositions also provide the opportunity to dose the entire daily therapeutic dose of enzalutamide in a single dosage unit, by improving the oral bioavailability of the drug.

Amorphous Enzalutamide

In some embodiments, enzalutamide is amorphous (i.e., in a non-crystalline state). Amorphous enzalutamide dissolves more quickly and to a greater extent than crystalline enzalutamide in an aqueous use environment, such as an aqueous dissolution medium of an in vitro dissolution test (e.g., phosphate buffered saline or model fasted duodenal fluid or simulated gastric fluid) or the in vivo environment of the stomach or small intestine. This enhanced dissolution results in higher enzalutamide oral bioavailability, compared to crystalline drug. An example of a crystalline form of enzalutamide is Form A, characterized by the powder x-ray diffraction pattern designated 'Bulk Crystalline Drug' in FIG. 1.

In some embodiments, enzalutamide is greater than 80% amorphous (i.e., containing less than 20% crystalline enzalutamide). In some embodiments, enzalutamide is greater than 90% amorphous (i.e., containing less than 10% crystalline enzalutamide). In some embodiments, enzalutamide is greater than 95% amorphous (i.e., containing less than 5% crystalline enzalutamide). In some embodiments, enzalutamide exhibits no crystalline character when measured by powder x-ray diffraction, by low angle x-ray scattering, by $^{13}$C-NMR, or by $^{19}$F-NMR.

Amorphous enzalutamide may be prepared by any known means, including spray-drying, hot melt extrusion, and precipitation from solution on addition of a non-solvent.

Pharmaceutical Compositions

The exact amount (effective dose) of enzalutamide will vary from subject to subject, depending on, for example, the species, age, weight and general or clinical condition of the subject, the severity or mechanism of any disorder being treated, the particular agent or vehicle used, the method and scheduling of administration, and the like.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

Enzalutamide conveniently administered in unit dosage form; for example, containing 0.05 to 10000 mg, 0.5 to 10000 mg, 5 to 1000 mg, 10 to 200 mg, or 40 to 160 mg of enzalutamide per unit dosage form.

Enzalutamide may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

In some embodiments, compositions comprise amorphous enzalutamide and a concentration-enhancing polymer. In some embodiments, compositions comprise amorphous enzalutamide and more than one concentration-enhancing polymer.

Amorphous enzalutamide and a concentration-enhancing polymer may be physically mixed, that is the two materials, as separate powders, may be blended by methods known in the pharmaceutical arts, including dry-blending, dry-granulation, and wet granulation.

In some embodiments, compositions comprise solid amorphous dispersions of enzalutamide and a concentration-enhancing polymer. In some embodiments, at least a major portion of the enzalutamide in the composition is amorphous. As used herein, the term "a major portion" of the enzalutamide means that at least 60% of the enzalutamide in the composition is in the amorphous form, rather than the crystalline form. In some embodiments, the enzalutamide in the dispersion is substantially amorphous. As used herein, "substantially amorphous" means that the amount of the enzalutamide in crystalline form does not exceed about 20%. In some embodiments, the enzalutamide in the dispersion is "almost completely amorphous, meaning that the amount of enzalutamide in the crystalline form does not exceed about 10%. Amounts of crystalline enzalutamide may be measured by powder X-ray diffraction, low angle x-ray scattering, differential scanning calorimetry (DSC), solid state 19F-NMR, solid state 13C-NMR, or any other standard quantitative measurement.

Compositions may contain from about 1 to about 80 wt % enzalutamide, depending on the dose of the drug and the effectiveness of the concentration-enhancing polymer. Enhancement of aqueous enzalutamide concentrations and relative bioavailability are typically best at low enzalutamide levels in the dispersion, typically less than about 75 wt %. In some embodiments, dispersions comprise greater than 20 wt % and less than 75 wt % enzalutamide. In some embodiments, dispersions comprise greater than 25 wt % and less than 75 wt % enzalutamide. In some embodiments, dispersions comprise greater than 50 wt % and less than 70 wt % enzalutamide.

Amorphous enzalutamide can exist within the solid amorphous dispersion as a pure phase, as a solid solution of enzalutamide homogeneously distributed throughout the polymer, or any combination of these states or states that lie intermediate between them.

In some embodiments, the dispersion is substantially homogeneous so that the amorphous enzalutamide is dispersed as homogeneously as possible throughout the polymer. "Substantially homogeneous" means that the fraction of enzalutamide that is present in relatively pure amorphous domains within the solid dispersion is relatively small, on the order of less than 20%, and in some embodiments, less than 10% of the total amount of enzalutamide.

In some embodiments, the solid amorphous dispersion may have some enzalutamide-rich domains. In some embodiments, the dispersion itself has a single glass transition temperature (Tg) which demonstrates that the dispersion is substantially homogeneous. This contrasts with a simple physical mixture of pure amorphous enzalutamide particles and pure amorphous polymer particles which generally displays two distinct Tgs, one that of the enzalutamide and one that of the polymer. Tg as used herein is the characteristic temperature where a glassy material, upon gradual heating, undergoes a relatively rapid (e.g., 10 to 100 seconds) physical change from a glass state to a rubber state. The Tg of an amorphous material such as a polymer, drug or dispersion can be measured by several techniques, including by a dynamic mechanical analyzer (DMA), a dilatometer, dielectric analyzer, and by a differential scanning calorimeter (DSC). The exact values measured by each technique can vary somewhat but usually fall within 10° to 30° C. of each other. Regardless of the technique used, when an amorphous dispersion exhibits a single Tg, this indicates that the dispersion is substantially homogenous.

Dispersions that are substantially homogeneous generally are more physically stable and have improved concentration-enhancing properties and, in turn, improved bioavailability, relative to nonhomogeneous dispersions.

Compositions comprising the enzalutamide and a concentration-enhancing polymer provide enhanced concentration of the dissolved enzalutamide in in vitro dissolution tests. It has been determined that enhanced drug concentration in in vitro dissolution tests in Model Fasted Duodenal (MFD) solution (MFDS) or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM 1-palmitoyl-2-oleyl-sn-glycero-3-phosphocholine. A composition can be dissolution-tested by adding it to MFD or PBS solution and agitating to promote dissolution. Generally, the amount of composition added to the solution in such a test is an amount that, if all the drug in the composition dissolved, would produce an enzalutamide concentration that is at least about 2-fold and, in some embodiments, at least 5-fold the equilibrium solubility of the crystalline enzalutamide alone in the test solution.

In some embodiments, compositions provide a Maximum Drug Concentration (MDC) that is at least about 2-fold the maximum concentration of a control composition comprising an equivalent quantity of crystalline enzalutamide but free from the concentration-enhancing polymer, during the first 90 minutes after dosing the dispersion into the in vitro medium. In other words, if the maximum concentration provided by the control composition is 10 μg/mL, then a composition provides an MDC of at least about 20 μg/mL. The comparison composition is conventionally crystalline enzalutamide. In some embodiments, the MDC of enzalutamide achieved with the compositions is at least about 5-fold the maximum concentration of the control composition. In some embodiments, the MDC of enzalutamide achieved with the compositions is at least about 10-fold the maximum concentration of the control composition.

In some embodiments, compositions, when tested in the in vitro test described above, exhibit a enzalutamide concentration one hour after reaching $C_{max}$ which is at least 80% of the $C_{max}$ concentration, where $C_{max}$ is the maximum enzalutamide concentration achieved in the in vitro test.

In some embodiments, compositions provide in an aqueous use environment a enzalutamide concentration versus time Area Under The Curve ($AUC_{90}$), for any period of at least 90 minutes between the time of introduction into the use environment and about 270 minutes following introduction to the use environment, that is at least 2-fold the $AUC_{90}$ of a control composition comprising an equivalent quantity of undispersed crystalline enzalutamide. In some embodiments, the compositions provide in an aqueous use environment a concentration versus time $AUC_{90}$, for any period of at least 90 minutes between the time of introduction into the use environment and about 270 minutes following introduction to the use environment, that is at least about 5-fold, in some embodiments at least about 10-fold, that of a control composition as described above. Such large enhancements in aqueous concentration versus time $AUC_{90}$ values are surprising given the extremely low aqueous solubility and hydrophobicity of enzalutamide.

In some embodiments, compositions meet both the $C_{max}$ and $AUC_{90}$ criteria when tested in vitro. The in vitro test to evaluate enhanced drug concentration in aqueous solution can be conducted by (1) adding with agitation a sufficient quantity of control composition, that is, the crystalline enzalutamide alone, to the in vitro test medium, typically MFD or PBS solution, to determine the maximum concentration of the enzalutamide achieved under the conditions of the test; (2) adding with agitation a sufficient quantity of test composition (e.g., the enzalutamide and polymer) in an equivalent test medium, such that if all the enzalutamide dissolved, the theoretical concentration of enzalutamide would exceed the observed maximum concentration of enzalutamide by a factor of about 20; and (3) comparing the measured MDC and/or aqueous concentration versus time $AUC_{90}$ of the test composition in the test medium with the maximum concentration, and/or the aqueous concentration versus time $AUC_{90}$ of the control composition. In conducting such a dissolution test, the amount of test composition or control composition used is an amount such that if all of the enzalutamide dissolved, the test enzalutamide concentration would be at least about 20-fold that of the control enzalutamide concentration.

The concentration of dissolved enzalutamide is typically measured as a function of time by sampling the test medium and plotting enzalutamide concentration in the test medium vs. time so that the MDC can be ascertained. The MDC is taken to be the maximum value of dissolved enzalutamide measured over the duration of the test. The aqueous concentration of the enzalutamide versus time $AUC_{90}$ is calculated by integrating the concentration versus time curve over any 90-minute time period between the time of introduction of the composition into the aqueous use environment (time equals zero) and 270 minutes following introduction to the use environment (time equals 270 minutes). Typically, when the composition reaches its MDC rapidly, in less than about 30 minutes, the time interval used to calculate $AUC_{90}$ is from time equals zero to time equals 90 minutes. However, if the $AUC_{90}$ over any 90-minute time period described above of a composition meets this criterion, it is encompassed within the compositions described in this disclosure. The time period 270 min is chosen because of its physiological relevance. Drug absorption in mammals generally occurs in the small intestine, and the small intestinal transit time in humans is approximately 4.5 hr, or 270 min.

In the in vivo situation, for example after oral dosing to a human, it is important that undissolved enzalutamide/polymer dispersion be capable of dissolving and resupplying the gastrointestinal fluid with dissolved drug as drug is removed from the system by absorption through the gastrointestinal wall into the bloodstream. The capacity of a dispersion to carry on this resupply function may be tested in vitro in a so-called "membrane test." In some embodiments, enzalutamide/polymer dispersions have high capacity to support transmembrane flux in the in vitro membrane test.

In some embodiments, when dosed orally to a human or other mammal, compositions provide an area under the plasma enzalutamide concentration versus time curve (AUC) that is at least about 1.25-fold that observed when a control composition comprising an equivalent quantity of crystalline drug is dosed. It is noted that such compositions can also be said to have a relative bioavailability of at least about 1.25. In some embodiments, compositions dosed orally to a human or other animal provide a plasma enzalutamide AUC that is at least about 2-fold that observed when a control composition comprising an equivalent quantity of crystalline drug is dosed. In some embodiments, the in vivo AUC is $AUC_{0-7days}$, as described below. Thus, the compositions can be evaluated in either in vitro or in vivo tests, or both.

Relative bioavailability of enzalutamide in the dispersions can be tested in vivo in animals or humans using conventional methods for making such a determination. An in vivo test, such as a crossover pharmacokinetic study, may be used to determine whether a composition of enzalutamide and concentration-enhancing polymer (or a composition comprised of amorphous enzalutamide without a concentration-enhancing polymer) provides an enhanced relative bioavailability compared with a control composition comprised of crystalline enzalutamide but no polymer as described above. In an in vivo crossover study a "test composition" of enzalutamide and polymer is dosed to half a group of test subjects and, after an appropriate washout period (at least 42 days) the same subjects are dosed with a "control composition" that comprises an equivalent quantity of crystalline enzalutamide with no concentration-enhancing polymer present. The other half of the group is dosed with the control composition first, followed by the test composition. The relative bioavailability is measured as the area under the plasma drug concentration versus time curve (AUC) determined for the test group divided by the plasma AUC provided by the control composition. In some embodiments, this test/control ratio is determined for each subject, and then the ratios are averaged over all subjects in the study. In vivo determinations of AUC can be made by plotting the plasma concentration of drug along the ordinate (y-axis) against time along the abscissa (x-axis), and using the trapezoidal rule method.

Thus, as noted above, one embodiment is one in which the relative bioavailability of the test composition is at least about 1.25 relative to a control composition comprised of crystalline enzalutamide but with no concentration-enhancing polymer as described above. (That is, the in vivo AUC provided by the test composition is at least about 1.25-fold the in vivo AUC provided by the control composition.) In some embodiments, the relative bioavailability of the test composition is at least about 2, relative to a control composition composed of crystalline enzalutamide but with no concentration-enhancing polymer present, as described above. The determination of AUCs is a well-known procedure and is described, for example, in Welling, "Pharmacokinetics Processes and Mathematics," ACS Monograph 185 (1986).

To carry out the in vivo AUC measurements for enzalutamide, the enzalutamide test and control compositions should be dosed at a 160 mg dose to a cohort of at least 24 subjects in the fasted state. Blood samples should be collected at 0 time (pre-dose), and at post-dose times 15, 30, and 45 minutes; and at 1, 2, 3, 4, 6, 8, and 12 hours; and at 0 and 12 hours on day 2; and at 0 hours on days 3, 5, and 7 (where 0 hours on days 2, 3, 5, and 7 correspond to the time of day when dosing occurred on day 1).

Relative bioavailability is measured using $AUC_{0-7days}$. The absolute value of the $AUC_{0-7days}$ is also used to determine if a dispersion formulation falls within compositions of this disclosure; i.e., pharmaceutical compositions comprising a solid amorphous dispersion of enzalutamide and a concentration-enhancing polymer, which when dosed to a cohort of 24 or more humans at a dose of 160 mg provides a mean area under the plasma enzalutamide concentration vs. time curve from the time of dosing to 7 days after dosing, $AUC_{0-7days}$, which is greater than 150 μg·hr/ml. This constraint applies to other doses as well, providing a plasma $AUC_{0-7days}$ which is greater than (150 μg·hr/ml)/(160 mg) or more generally greater than 0.94 μg·hr/ml·mg, where mg refers to the weight of the enzalutamide dose.

Inspection of the plasma enzalutamide concentration versus time curves for the dosed subjects will give the maximum enzalutamide concentration $C_{max}$ achieved during the post-dose period. A mean $C_{max}$ can be calculated for the cohort of subjects. This disclosure provides a pharmaceutical composition comprising a solid amorphous dispersion of enzalutamide and a concentration-enhancing polymer, said dispersion when dosed to a cohort of 24 or more humans at a dose of 160 mg providing a mean maximum plasma enzalutamide concentration $C_{max}$ which is greater than 2 μg/ml, In some embodiments, greater than 2.5 μg/ml. This constraint applies to other doses as well, providing a $C_{max}$ greater than (2 μg/ml)/(160 mg), where mg refers to the weight of the enzalutamide dose. In some embodiments, $C_{max}$ is greater than (2.5 μg/ml)/(160 mg); this constraint can be expressed as providing a $C_{max}$ greater than 12.5 ng/ml·mg. In some embodiments, $C_{max}$ is greater than 15.6 ng/ml·mg.

Concentration-Enhancing Polymers

Concentration-enhancing polymers suitable for use in the compositions are be inert, in the sense that they do not chemically react with enzalutamide, are pharmaceutically acceptable (i.e. are non-toxic), and have at least some solubility in aqueous solution at physiologically relevant pHs (e.g. 1-8). The concentration-enhancing polymer can be neutral or ionizable, and should have an aqueous-solubility of at least 0.1 mg/mL over at least a portion of the pH range of 1-8.

A polymer is a "concentration-enhancing polymer" if it meets at least one, or, in some embodiments, both, of the following conditions. The first condition is that the concentration-enhancing polymer increases the in vitro MDC of enzalutamide in the environment of use relative to a control composition consisting of an equivalent amount of crystalline enzalutamide but no polymer. That is, once the composition is introduced into an environment of use, the polymer increases the aqueous concentration of enzalutamide relative to the control composition. In some embodiments, the polymer increases the MDC of enzalutamide in aqueous solution by at least 2-fold relative to a control composition; in some embodiments, by at least 5-fold; in some embodiments, by at least 10-fold. The second condition is that the concentration-enhancing polymer increases the $AUC_{90}$ of the enzalutamide in the in vitro environment of use relative to a control composition consisting of enzalutamide but no polymer as described above. That is, in the environment of use, the composition comprising the enzalutamide and the concentration-enhancing polymer provides an area under the concentration versus time curve ($AUC_{90}$) for any period of 90 minutes between the time of introduction into the use environment and about 270 minutes following introduction to the use environment that is at least 2-fold that of a control composition comprising an equivalent quantity of enzalutamide but no polymer. In some embodiments, the AUC provided by the composition is at least 5-fold; in some embodiments, at least 10-fold that of the control composition.

Concentration-enhancing polymers may be cellulosic or non-cellulosic. The polymers may be neutral or ionizable in aqueous solution. In some embodiments, polymers are ionizable and cellulosic. In some embodiments, polymers are ionizable cellulosic polymers.

In some embodiments, polymers are "amphiphilic" in nature, meaning that the polymer has hydrophobic and hydrophilic portions. The hydrophobic portion may comprise groups such as aliphatic or aromatic hydrocarbon groups. The hydrophilic portion may comprise either ionizable or non-ionizable groups that are capable of hydrogen bonding such as hydroxyls, carboxylic acids, esters, amines or amides. The relative contents of hydrophobic, ionizable hydrophilic, and non-ionizable hydrophilic groups in the polymer can be optimized to provide improved functionality as a concentration-enhancing polymer.

Amphiphilic polymers may have relatively strong interactions with enzalutamide and may promote the formation of various types of polymer/drug assemblies in the use environment. In addition, the repulsion of the like charges of ionized groups of such polymers may serve to limit the size of the polymer/drug assemblies to the nanometer or submicron scale. For example, while not wishing to be bound by a particular theory, such polymer/drug assemblies may comprise hydrophobic enzalutamide clusters surrounded by the polymer with the polymer's hydrophobic regions turned inward towards the enzalutamide and the hydrophilic regions of the polymer turned outward toward the aqueous environment. Alternatively, the polar functional groups of the polymer may associate, for example, via hydrogen bonds, with polar groups of the enzalutamide. In the case of ionizable polymers, the hydrophilic regions of the polymer would include the ionized functional groups. Such polymer/drug assemblies in solution may well resemble charged polymeric micellar-like structures. In any case, regardless of the mechanism of action, the inventors have observed that such amphiphilic polymers, particularly ionizable cellulosic polymers, have been shown to improve the MDC and/or $AUC_{90}$ of enzalutamide in aqueous solution in vitro relative to crystalline control compositions free from such polymers.

Surprisingly, such amphiphilic polymers can greatly enhance the maximum concentration of enzalutamide obtained when enzalutamide is dosed to a use environment. In addition, such amphiphilic polymers interact with enzalutamide to prevent the precipitation or crystallization of the enzalutamide from solution despite its concentration being substantially above its equilibrium concentration. In some embodiments, when the compositions are solid amorphous dispersions of enzalutamide and the concentration-enhancing polymer, the compositions provide a greatly enhanced drug concentration, particularly when the dispersions are substantially homogeneous. The maximum drug concentration may be 5-fold and often more than 10-fold the equilibrium concentration of the crystalline enzalutamide. Such enhanced enzalutamide concentrations in turn lead to substantially enhanced relative bioavailability for enzalutamide.

One class of polymers comprises neutral non-cellulosic polymers, including, but not limited to, vinyl polymers and copolymers having substituents of hydroxyl, alkylacyloxy, and cyclicamido polyvinyl alcohols that have at least a portion of their repeat units in the unhydrolyzed (vinyl acetate) form; polyvinyl alcohol polyvinyl acetate copolymers; polyvinyl pyrrolidone; polyvinylpyrrolidone vinyl acetate; and polyethylene polyvinyl alcohol copolymers.

Another class of polymers comprises ionizable non-cellulosic polymers, including, but not limited to, carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass; amine-functionalized polyacrylates and polymethacrylates; proteins; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Commercial grades of such copolymers include the EUDRAGITS®, which are copolymers of methacrylates and acrylates; and graft copolymers of polyethyleneglycol, polyvinylcaprolactam, and polyvinylacetate, one commercially available version of a graft copolymer known as SOLUPLUS®.

Other polymers comprise ionizable and neutral cellulosic polymers with at least one ester- and/or ether-linked substituent, in which the polymer has a degree of substitution of at least 0.1 for each substituent. In the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

As used herein, a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.1 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics may be prepared by substituting the cellulose at any or all of the 3 hydroxyl substituents present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Hydrophilic regions of the polymer can be either those portions that are relatively unsubstituted, since the unsubstituted hydroxyls are themselves relatively hydrophilic, or those regions that are substituted with hydrophilic substituents. Examples of hydrophobic substitutents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic groups include ether-or ester-linked nonionizable groups such as the hydroxy alkyl substituents hydroxyethyl, hydroxypropyl, and the alkyl ether groups such as ethoxyethoxy or methoxyethoxy. In some embodiments, hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable groups include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

In some embodiments, neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

In some embodiments, cellulosic polymers comprise polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic group may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

A particularly desirable subset of cellulosic ionizable polymers are those that possess both a carboxylic acid functional aromatic substituent and an alkylate substituent and thus are amphiphilic. Exemplary polymers include cellulose acetate phthalate (CAP), methyl cellulose acetate phthalate, ethyl cellulose acetate phthalate, hydroxypropyl cellulose acetate phthalate, hydroxylpropyl methyl cellulose phthalate (HPMCP), hydroxypropyl methyl cellulose acetate phthalate (HPMCAP), hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

In some embodiments, cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate.

While, as listed above, a wide range of polymers may be used to form dispersions of enzalutamide, the inventors have found that relatively hydrophobic polymers have shown the best performance as demonstrated by high MDC and $AUC_{90}$ in vitro dissolution values. In particular, cellulosic polymers that are aqueous insoluble in their nonionized state but are aqueous soluble in their ionized state perform particularly well. A particular subclass of such polymers are the so-called "enteric" polymers which include, for example, hydroxypropylmethylcellulose acetate succinate (HPMCAS) and certain grades of hydroxypropyl methyl cellulose acetate phthalate (HPMCAP) and cellulose acetate trimellitate (CAT). Dispersions formed from such polymers generally show very large enhancements in the maximum drug concentration achieved in dissolution tests relative to that for a crystalline drug control.

In some embodiments, concentration-enhancing polymers for use in dispersions with enzalutamide are hydroxypropylmethylcellulose acetate succinate (HPMCAS), hydroxypropylmethylcellulose (HPMC), hydroxypropylmethylcellulosephthalate (HPMCP), polyvinylpyrrolidonevinylacetate (PVP-VA), copolymers of methacrylic acid and methylmethacrylate (approximate 1:1 ratio) available as EUDRAGIT L-100®, and graft copolymers of polyethyleneglycol, polyvinylcaprolactam, and polyvinylacetate, one commercially available version of a graft copolymer is known as SOLUPLUS®.

In some embodiments, the enzalutamide/polymer dispersion, regardless of preparation method, may contain one or more lipophilic microphase-forming materials, comprising surfactants and lipidic mesophase-forming materials, or mixtures thereof. Examples of lipophilic microphase-forming materials are sulfonated hydrocarbons and their salts, such as dioctylsodiumsulfocuccinate and sodium laurylsulfate; polyoxyethylene sorbitan fatty acid esters, such as polysorbate-80 and polysorbate-20; polyoxyethylene alkyl ethers; polyoxyethylene castor oil; polyoxyethylene (−40 or −60) hydrogenated castor oil; tocopheryl polyethyleneglycol 1000 succinate; glyceryl polyethyleneglycol-8 caprylate/caprate; polyoxyethylene-32 glyceryl laurate; polyoxyethylene fatty acid esters; polyoxyethylene-polyoxypropylene block copolymers; polyglycolized glycerides; long-chain fatty acids such as palmitic and stearic and oleic and ricinoleic acids; medium-chain and long-chain saturated and unsaturated mono-, di- and tri-glycerides and mixtures thereof; fractionated coconut oils; mono- and di-glycerides of capric and caprylic acids; bile salts such as sodium taurocholate; and phospholipids such as egg lecithin, soy lecithin, 1,2-diacyl-sn-glycerophosphorylcholines such as 1-palmitoyl-2-oleyl-sn-glycerophosphorylcholine, dipalmitoyl-sn-glycerophosphorylcholine, distearoyl-sn-glycerophosphorylcholine, and 1-palmitoyl-2-stearoyl-sn-glycerophosphorylcholine.

In some embodiments, the enzalutamide/polymer dispersion contains less than 30% by weight of lipophilic microphase-forming materials. In some embodiments, the enzalutamide/polymer dispersion contains less than 20% by weight of lipophilic microphase-forming materials. In some embodiments, the enzalutamide/polymer dispersion contains less than 10% by weight of lipophilic microphase-forming materials. In some embodiments, the enzalutamide/polymer dispersion contains less than 5% by weight of lipophilic microphase-forming materials.

To obtain the best performance, particularly upon storage for long times prior to use, it is preferred that the enzalutamide remain, to the extent possible, in the amorphous state. The inventors have found that this is best achieved when the glass-transition temperature, Tg, of the solid amorphous dispersion is substantially above the storage temperature of the composition. In particular, it is preferable that the Tg of the amorphous state of the dispersion be at least 40° C. In some embodiments, the Tg of the amorphous state of the dispersion is at least 60° C. To achieve a high Tg for an enzalutamide/polymer dispersion, it is desirable that the polymer have a high Tg. Exemplary high Tg concentration-enhancing polymers are HPMCAS, HPMCP, CAP, CAT.

The polymer is not particularly limited, so long as enzalutamide can be carried as the solid dispersion. In some embodiments, the polymer is not particularly limited, so long as enzalutamide can be an amorphous state. Examples of the polymer include polyvinyl pyrrolidone (PVP), polyethyleneoxide (PEO), 5 poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose (HPMC), hydroxypropyl cellulose (HPC), carboxymethyl ethylcellulose (CMEC), hydroxypropyl methylcellulose acetate succinate (HPMCAS), cellulose acetate phthalate (CAP), cellulose acetate trimellitate (CAT), ethyl cellulose, cellulose acetate, cellulose butyrate, cellulose acetate butyrate, dextran polymer derivatives, and pharmaceutically acceptable forms, derivatives. In some embodiments, the polymer is hydroxypropyl methylcellulose acetate succinate (HPMCAS)..

Preparation of Compositions

Dispersions of enzalutamide and concentration-enhancing polymer may be made according to any known process which results in at least a major portion (at least 60%) of the enzalutamide being in the amorphous state. Exemplary mechanical processes include milling and hot-melt extrusion; melt processes include high temperature fusion, solvent modified fusion and melt-congeal processes; and solvent processes include non-solvent precipitation, spray coating and spray-drying. Although the dispersions may be made by any of these processes, the dispersions generally have their maximum bioavailability and stability when the enzalutamide is dispersed in the polymer such that it is substantially amorphous and substantially homogeneously distributed throughout the polymer.

Particularly effective methods for forming solid amorphous dispersions of enzalutamide and concentration-enhancing polymers are solvent processing and hot melt extrusion.

In general, as the degree of homogeneity of the dispersion increases, the enhancement in the aqueous concentration of enzalutamide and relative bioavailability increases as well. Given the low aqueous solubility and bioavailability of crystalline enzalutamide, it is highly preferred for the dispersions to be as homogeneous as possible. Thus, most preferred are dispersions having a single glass transition temperature, which indicates a high degree of homogeneity.

In some embodiments, substantially amorphous and substantially homogeneous dispersions are made by any of the methods described above. In some embodiments, dispersions are formed by "solvent processing," in which enzalutamide and a polymer are dissolved in a common solvent. "Common" here means that the solvent, which can be a mixture of compounds, will simultaneously dissolve the drug and the polymer(s). After both the enzalutamide and the polymer have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. In some embodiments, removal of the solvent results in a solid dispersion which is substantially homogeneous. As described previously, in such substantially homogeneous dispersions, the enzalutamide is dispersed as homogeneously as possible throughout the polymer and can be thought of as a solid solution of enzalutamide in the polymer(s). When the resulting dispersion constitutes a solid solution of enzalutamide in polymer, the dispersion may be thermodynamically stable, meaning that the concentration of enzalutamide in the polymer is at or below its equilibrium value. Alternatively, the composition may be a supersaturated solid solution where the enzalutamide concentration in the dispersion polymer(s) is above its equilibrium value.

The solvent may be removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying can be any organic compound in which enzalutamide and polymer are mutually soluble. In some embodiments, the solvent is also volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying subsequent to the spray-drying or spray-coating process. Solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and enzalutamide are sufficiently soluble to make the spray-drying process practicable. Generally, due to the hydrophobic nature of enzalutamide, non-aqueous solvents used. Non-aqueous solvents comprise less than about 10 wt % water; in some embodiments, less than 1 wt % water.

In some embodiments, solvents for spray drying enzalutamide/polymer solutions are acetone, ethanol, methanol, mixtures thereof, and mixtures with water.

Generally, the temperature and flow rate of the drying gas is chosen so that the polymer/drug-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 µm to 500 µm in diameter, with 5 to 100 µm being more typical. The large surface-to-volume ratio of the droplets and the large driving force for evaporation of solvent leads to actual drying times of a few seconds or less, and more typically less than 0.1 second. This rapid drying is often critical to the particles maintaining a uniform, homogeneous dispersion instead of separating into drug-rich and polymer-rich phases. As above, to get large enhancements in concentration and bioavailability it is often necessary to obtain as homogeneous a dispersion as possible. Solidification times should be less than 100 seconds. In some embodiments, solidification time is less than a few seconds. In some embodiments, solidification time is less than 1 second. In general, to achieve this rapid solidification of the enzalutamide/polymer solution, the size of droplets formed during the spray-drying process is less than about 100 µm in diameter. The resultant solid particles thus formed are generally less than about 100 µm in diameter.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of enzalutamide molecules in the dispersion, thereby improving its stability. Generally, the solvent content of the dispersion as it leaves the spray-drying chamber should be less than 10 wt %. In some embodiments, the solvent content of the dispersion as it leaves the spray-drying chamber is less than 2 wt %. In some cases, it may be preferable to spray a solvent or a solution of a polymer or other excipient into the spray-drying chamber to form granules, so long as the dispersion is not adversely affected.

Spray-drying processes and spray-drying equipment are described generally in Perry's Chemical Engineers' Handbook, Sixth Edition (R. H. Perry, D. W. Green, J. O. Maloney, eds.) McGraw-Hill Book Co. 1984, pages 20 54 to 20 57. More details on spray-drying processes and equipment are reviewed by Marshall "Atomization and Spray-Drying," 50 Chem. Eng. Prog. Monogr. Series 2 (1954).

The spray drying equipment used in the Examples below were:

Mini Spray Dryer. This bench-top spray dryer is an atomizer in the top cap of a vertically oriented 10-cm diameter stainless steel pipe. The atomizer was a two-fluid nozzle (Spraying Systems Co. 1650 fluid cap and 64 air cap). Atomizing gas (nitrogen) was delivered to the nozzle at 100° C. at a flow rate of 15 gm/min, and the spray solution was delivered to the nozzle at room temperature and at a flow rate of 1.0 gm/min using a syringe pump (Harvard Apparatus, Syringe Infusion Pump. Filter paper attached to a supporting screen was clamped to the bottom end of the pipe to collect the solid spray-dried material and allow the nitrogen and evaporated solvent to escape. .

Bend Laboratory Spray Drier (BLD). The BLD is a custom-made spray drier manufactured at Bend Research, Inc. The spray solution is delivered to an atomizer located in the spray drying chamber. The chamber consists of three sections: a top section, a straight-side section, and a cone section. The top section contains a perforated plate to create an organized co-current flow of drying gas and the atomized spray solution within the drying chamber. The drying gas enters the top section through the drying-gas inlet and passes through the perforated plate. The drying gas then enters the straight side section of the spray-drying chamber. The atomizer slightly protrudes from the perforated plate. The spray solution is sprayed into the straight-side section of the spray-drying chamber. The flow rate of drying gas and spray solution are selected such that the atomized spray solution forms solid particles, which are collected in the cone section of the spray-drying chamber. The spray-dried particles, evaporated solvent, and drying gas are removed from the spray-drying chamber through an outlet port and sent to a cyclone separator where the spray-dried particles are collected. The evaporated solvent and drying gas are then sent to a filter for removal of any remaining particles before discharge.

PSD-1 Spray Drier. This spray drying apparatus is a type XP Portable Spray-Dryer with a Liquid Feed Process Vessel Model No. PSD-1 (Niro A/S, Soeborg, Denmark). The PSD-1 is equipped with a pressure nozzle. Heated drying gas (nitrogen, typically at 100° C.) is delivered to the drying chamber through an inlet duct and a DPH gas disperser (Niro) that surrounds the nozzle. The resulting SDD exits the chamber with the drying gas and evaporates solvents through transport ducts and into a cyclone. At the top of the cyclone is an exhaust vent that allowed the nitrogen and evaporated solvent to escape. The SDD is collected in a canister.

In some embodiments, formation of enzalutamide/polymer amorphous dispersions is achieved using hot-melt extrusion. Powder mixtures of enzalutamide and concentration-enhancing polymer are heated and passed through an extruder such as a 7.5 mm MP&R extruder, which is capable of reaching 210° C. and is equipped with a ⅛ inch cylindrical die. After the extruded enzalutamide/polymer mass exits the extruder, it is milled. In some embodiments, for the purpose of enhancing the in vitro $C_{max}$ and $AUC_{90}$ in an enzalutamide dissolution test, a enzalutamide/polymer dispersion has a mean particle size less than 150 µm. In some embodiments, mean particle size is less than 50 µm. In some embodiments, concentration-enhancing polymers for use in hot-melt extruded enzalutamide/polymer solid amorphous dispersions are hydroxypropylmethylcellulose acetate succinate (HPMCAS) and polyvinylpyrrolidonevinylacetate (PVP-VA).

The amount of concentration-enhancing polymer relative to the amount of enzalutamide present in the dispersions may vary widely. The composition of enzalutamide/polymer dispersions is expressed, for example, as 25% A:HPMCAS-M, where 25% A means "25% active" and the dispersion contains 25% (by weight) enzalutamide and 75% (by weight) hydroxypropylmethlycellulose acetate succinate M-grade. In enzalutamide dispersions described herein, the enzalutamide content is generally greater than 20% A; in some embodiments, from 25% A to 75% A; in some embodiments, from 50% A to 70% A. For a specific concentration-enhancing polymer, the enzalutamide/polymer ratio that yields optimum results is best determined in in vitro dissolution tests and/or in vivo bioavailability tests.

The ratio of the polymer to enzalutamide is not particularly limited, so long as enzalutamide can be formed the solid dispersion. In some embodiments, the ratio of the polymer to enzalutamide is not particularly limited, so long as enzalutamide can be an amorphous state. The ratio of the polymer is specifically 0.5 to 3 parts by weight, 1 to 3 parts by weight in other embodiments, and 2 to 3 parts by weight in still other embodiments, with respect to 1 part by weight of enzalutamide.

In addition, the amount of concentration-enhancing polymer that can be used in a dosage form is often limited by the total mass requirements of the dosage form. For example, when oral dosing to a human is desired, at low enzalutamide-to-polymer ratios the total mass of drug and polymer may be unacceptably large for delivery of the desired dose in a single tablet or capsule. Thus, it is often necessary to use enzalutamide-to-polymer ratios that are less than optimum in specific dosage forms to provide a sufficient enzalutamide dose in a dosage form that is small enough to be easily swallowed by a human.

Solid amorphous dispersions having fine particles, such as less than 50 μm in average particle diameter, can have poor flow characteristics. Poor flowability of a solid amorphous dispersion can lead to difficulties in handling and compressing the solid amorphous dispersion. For example, poor flowability of the solid amorphous dispersion can lead to inconsistent flow through processing equipment and/or inconsistent or incomplete filling of tablet or capsule dies, which can lead to delivery of inconsistent dosages.

In addition to particle size, the flow characteristics of the solid amorphous dispersion can also be dependent on the bulk specific volume of the solid amorphous dispersion. The bulk specific volume of a powder is the inverse of the bulk density of a powder and can be measured as the volume occupied by a unit mass of the powder, such as in cubic centimeters per gram, when the powder is poured into a container, such as a graduated cylinder. Generally, the lower the bulk specific volume of a powder, the better the flowability of the particles. Improving the flowability of the solid amorphous dispersion can therefore be more desirable for a solid amorphous dispersion having a higher bulk specific volume. For example, in some exemplary methods, the solid amorphous dispersion can have a bulk specific volume greater than or equal to 3 cc/g, greater than or equal to 5 cc/g, greater than or equal to 8 cc/g, from 3 to 5 cc/g, and/or from 3 to 8 cc/g.

High-shear mixing of the solid amorphous dispersion and a glidant can increase the uniformity of the mixed particles, such as producing an ordered mixture and/or an interactive mixture. As used herein, the term "glidant" means a substance that, when added to a powder, improves the flowability of the powder, such as by reducing inter-particle friction. Exemplary glidants include but are not limited to colloidal silicas, colloidal silicon dioxide, fumed silica, CAB-O-SILO M-5P, AEROSIL®, talc, starch, and magnesium aluminum silicates.

A blend of the solid amorphous dispersion and the glidant using high-shear mixing can have improved flowability, as measured by Carr's Index, compared to the flowability of the solid amorphous dispersion alone. In general, the lower the Carr's Index, the better the flowability of the substance. As used herein, the term "Carr's Index" means a dimensionless parameter "C" used to characterize the flowability of a substance, such as a powder, where $C=1-(B/T)$, B is the bulk density of the substance and T is the tapped density of the substance. The Carr's Index can be expressed as a percentage, e.g., if $C=0.5$, the Can's Index can be expressed as 50%. The bulk density is equal to mass per volume (g/cc) of a sample before being tapped and the tapped density is equal to the mass of a sample divided by the volume of the sample after the sample is tapped for 2000 cycles in a Vankel Tap density instrument.

A powder having a lower Carr's Index can also be easier to compress into a tablet. In some exemplary methods, a mixture having a Can's Index greater than 40%, for example, can be difficult to compress into a tablet. For example, a tablet formed from a mixture having a high Can's Index can be more likely to crack, fracture, or otherwise fail to stick together or maintain a tablet form after compression. Adding a glidant to the solid amorphous dispersion with high-shear mixing can produce a mixture having a low Can's Index, such as below 40% and/or 35%, that is suitable for direct compression. This allows direct compression of the solid amorphous dispersion without the need to include an intermediate granulation process to decrease the Can's Index of the mixture to a suitable level.

An exemplary method for forming a pharmaceutical dosage form comprises: providing a solid amorphous dispersion comprising particles wherein the particles comprise enzalutamide and a polymer, the solid amorphous dispersion having an average particle diameter of less than 50 μm; forming an ordered mixture by high-shear mixing a blend comprising the solid amorphous dispersion and a powdered glidant, the glidant having an average particle diameter of less than or equal to one-fifth the average particle diameter of the solid amorphous dispersion after high-shear mixing; and forming the pharmaceutical dosage form by at least one of directly compressing the ordered mixture to form a tablet and encapsulating the ordered mixture to form a capsule.

Another exemplary method of preparing a pharmaceutical dosage form comprises: providing a solid amorphous dispersion comprising particles wherein the particles comprise enzalutamide and a polymer, the solid amorphous dispersion having an average particle diameter of less than 50 μm; forming an ordered mixture comprising the solid amorphous dispersion and a glidant using high-shear mixing, the ordered mixture having a Carr's Index of less than 40%; and forming the pharmaceutical dosage form by directly compressing the ordered mixture to form a tablet or encapsulating the ordered mixture to form a capsule.

Another exemplary method for forming a pharmaceutical dosage form comprises: providing a solid amorphous dispersion comprising particles, the particles comprising enzalutamide and a polymer, the solid amorphous dispersion having an average particle diameter of less than 50 μm;

forming a blend comprising the solid amorphous dispersion and a powdered glidant using high-shear mixing, the high-shear mixing having a Froude Number greater than 0.2; and forming the pharmaceutical dosage form by at least one of directly compressing the blend to form a tablet and encapsulating the blend to form a capsule.

As used herein, the term "Froude Number" means a dimensionless parameter "Fr" used to characterize a mixing process, such that $Fr=V^2/gD_c$, where V is the characteristic velocity of the particles in a mixing chamber, $D_c$ is the characteristic diameter of the chamber, and g is the acceleration due to Earth's gravity. For a rotating agitator, such as an impeller, the characteristic velocity may be defined as $V=\pi D_a N$, where $D_a$ is the diameter of the agitator and N is the agitator rotation rate in revolutions per unit time.

As used herein, the term "high-shear mixing" means a powder mixing process characterized by a Froude Number within a specified range, such as greater than 0.01, greater than 0.1, greater than greater than 0.5, greater than 1, greater than 10, and/or greater than 20, for example Where the Froude Number is not specified, the term "high-shear mixing" means a powder mixing process characterized by a Froude Number of at least 1. The term "high-shear mixing" does not include high-shear granulation using a liquid, or dissolving or dispersing a solid in a liquid.

As used herein, the term "low-shear mixing" means a conventional mixing process that is not high-shear mixing.

As used herein, the term "ordered mixture" means a mixture of powders having a level of uniformity that is greater than a level achievable by random mixing.

As used herein, the term "interactive mixture" means a mixture of a first powder having a first average particle size and a second powder having a second average particle size that is larger than the first average particle size, wherein all, substantially all or at least 90% of the particles of the first powder interact with and adhere to at least one of the plurality of the particles of the second powder. In some embodiments, an ordered mixture is also an interactive mixture.

As used herein, the term "average particle size" means the D50. The term D50 means that 50 vol % of the particles have a diameter that is smaller than this, and 50 vol % of the particles have a diameter that is larger than this. The average particle size may be measured using standard laser diffraction particle sizing techniques known in the art. One example of an instrument to measure the particle size of the dry powders is the Masteresizer 2000, manufactured by Malvern Instruments Ltd (Worcestershire, UK). In some embodiments, the average particle diameter of the glidant after high-shear mixing is less than that of the dispersion particles. This can be determined by scanning-electron microscopy analysis of the blend. A comparison of the dispersion particles before high-shear mixing with the glidant and after high-shear mixing will show small particles of glidant on the surfaces of the dispersion particles.

Excipients and Dosage Forms

Although the key ingredients present in the compositions are simply the enzalutamide to be delivered and the concentration-enhancing polymer(s), the inclusion of other excipients in the composition may be useful. These excipients may be utilized with the enzalutamide and polymer composition in order to formulate the composition into tablets, capsules, suspensions, powders for suspension, creams, transdermal patches, depots, and the like. The composition of enzalutamide and polymer can be added to other dosage form ingredients in essentially any manner that does not substantially alter the enzalutamide. The excipients may be either physically mixed with the dispersion and/or included within the dispersion.

The solid dispersion comprising enzalutamide and the polymer is further mixed with one or more pharmaceutically acceptable additives to prepare a pharmaceutical composition.

The additives are not particularly limited, so long as they are pharmaceutically acceptable. Examples of the additives include a filler, a binder, a disintegrator, an acidulant, an effervescent agent, an artificial sweetener, a flavor, a lubricant, a coloring agent, a stabilizing agent, a buffer, an antioxidant, a glidant, and the like.

The filler may be selected from, for example, mannitol, lactose, starch, corn starch, calcium hydrogen phosphate hydrate, magnesium carbonate, calcium carbonate, purified sucrose, glucose, and the like.

The binder may be selected from, for example, hydroxypropylmethyl cellulose, hydroxypropyl cellulose, polyvinyl alcohol, methyl cellulose, gum arabic, and the like.

The disintegrator may be selected from, for example, corn starch, starches, crystalline cellulose, carmellose calcium, carmellose sodium, croscarmellose sodium, light anhydrous silicic acid, calcium silicate, low-substituted hydroxypropyl cellulose, partially pregelatinized starch, sodium carboxymethyl starch, agar powder, crospovidone, synthetic aluminum silicate, sucrose fatty acid esters, lactose hydrate, D-mannitol, anhydrous citric acid, and the like.

The acidulant may be selected from, for example, citric acid, tartaric acid, malic acid, and the like.

The effervescent agent may be selected from, for example, sodium bicarbonate and the like.

The artificial sweetener may be selected from, for example, saccharin sodium, dipotassium glycyrrhizinate, aspartame, *stevia*, thaumatin, and the like.

The flavor may be selected from, for example, lemon, lemon-lime, orange, menthol, and the like.

The lubricant may be selected from, for example, magnesium stearate, calcium stearate, sucrose fatty acid esters, sodium stearyl fumarate, polyethylene glycol, talc, stearic acid, and the like.

The coloring agent may be selected from, for example, yellow ferric oxide, red ferric oxide, food yellow No. 4, food yellow No. 5, food red No. 3, food red No. 102, food blue No. 3, and the like.

The buffer may be selected from, for example, citric acid, succinic acid, fumaric acid, tartaric acid, ascorbic acid, or salts thereof; glutamic acid, glutamine, glycine, aspartic acid, alanine, arginine, or salts thereof; magnesium oxide, zinc oxide, magnesium hydroxide, phosphoric acid, boric acid, or their salts; and the like.

The antioxidant may be selected from, for example, ascorbic acid, dibutyl hydroxytoluene, propyl gallate, and the like.

The glidant may be selected from, for example, light anhydrous silicic acid, titanium oxide, stearic acid, colloidal silica, colloidal 20 silicon dioxide, fumed silica, CAB-O-SILO M-5P, AEROSIL®, talc, starch, and magnesium aluminum silicates and the like.

These additives may be added alone in an appropriate amount, or as a combination of two or more thereof in appropriate amounts.

One very useful class of excipients to be added to the formulation after formation of the enzalutamide/polymer dispersion comprises surfactants and surface-active agents. Suitable surfactants and surface-active agents are sulfonated hydrocarbons and their salts, such as dioctylsodiumsulfocuccinate and sodium laurylsulfate; polyoxyethylene sorbitan fatty acid esters, such as polysorbate-80 and polysorbate-20; polyoxyethylene alkyl ethers; polyoxyethylene castor oil; polyoxyethylene (−40 or −60) hydrogenated castor oil; tocopheryl polyethyleneglycol 1000 succinate; glyceryl polyethyleneglycol-8 caprylate/caprate; polyoxyethylene-32 glyceryl laurate; polyoxyethylene fatty acid esters; polyoxyethylene-polyoxypropylene block copolymers; polyglycolized glycerides; long-chain fatty acids such as palmitic and stearic and oleic and ricinoleic acids; medium-chain and long-chain saturated and unsaturated mono-, di- and triglycerides and mixtures thereof; fractionated coconut oils; mono- and di-glycerides of capric and caprylic acids; bile salts such as sodium taurocholate; and phospholipids such as egg lecithin, soy lecithin, 1,2-diacyl-sn-glycerophosphorylcholines such as 1-palmitoyl-2-oleyl-sn-glycerophosphorylcholine, dipalmitoyl-sn-glycerophosphorylcholine, distearoyl-sn-glycerophosphorylcholine, and 1-palmitoyl-2-stearoyl-sn-glycerophosphorylcholine. Such materials can be advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug, crystalline or amorphous. These surfactants may comprise up to 5% of the composition.

The addition of pH modifiers such as acids, bases, or buffers may also be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is anionic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, calcium diphosphate, and starch.

Examples of disintegrants include sodium starch glycolate, sodium alginate, carboxy methyl cellulose sodium, methyl cellulose, and croscarmellose sodium.

Examples of binders include methyl cellulose, microcrystalline cellulose, starch, and gums such as guar gum, and tragacanth.

Examples of lubricants include magnesium stearate and calcium stearate.

Other conventional excipients may be employed, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

The compositions may be delivered by a wide variety of routes, including, but not limited to, oral, nasal, rectal, and pulmonary. In some embodiments, compositions are delivered by the oral route.

The pharmaceutical compositions comprising the solid dispersion, can be formulated into various dosage forms, including tablets, powders, fine granules, granules, dry syrups, capsules and the like as well as the solid dispersion itself. In some embodiments, the solid pharmaceutical composition is in tablet form.

Compositions disclosed herein may also be used in a wide variety of dosage forms for administration of enzalutamide. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions disclosed herein to form a material suitable for the above dosage forms.

The compositions may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating.

In some embodiments, dispersions of enzalutamide are formulated for long-term storage in the dry state as this promotes the chemical and physical stability of the enzalutamide. Various excipients and additives are combined with the compositions to form the dosage form. For example, it may be desirable to add some or all of the following: preservatives such as sulfites (an antioxidant), benzalkonium chloride, methyl paraben, propyl paraben, benzyl alcohol or sodium benzoate; suspending agents or thickeners such as xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, or titanium dioxide; anticaking agents or fillers such as silicon oxide, or lactose; flavorants such as natural or artificial flavors; sweeteners such as sugars such as sucrose, lactose, or sorbitol as well as artificial sweeteners such as aspartame or saccharin; wetting agents or surfactants such as various grades of polysorbate, docusate sodium, or sodium lauryl sulfate; solubilizers such as ethanol propylene glycol or polyethylene glycol; coloring agents such as FD and C Red No. 3 or FD and C Blue No. 1; and pH modifiers or buffers such as carboxylic acids (including citric acid, ascorbic acid, lactic acid, and succinic acid), various salts of carboxylic acids, amino acids such as glycine or alanine, various phosphate, sulfate and carbonate salts such as trisodium phosphate, sodium bicarbonate or potassium bisulfate, and bases such as amino glucose or triethanol amine.

In some embodiments, an additional concentration-enhancing polymer may be added. An additional concentration-enhancing polymer may act as a thickener or suspending agent in formulations which are constituted with a liquid before dosing, and which may provide additional precipitation inhibition for all dosage forms after dosing to an aqueous use environment.

In some cases, the overall dosage form or particles, granules or beads that make up the dosage form may have superior performance if coated with an enteric polymer to prevent or retard dissolution until the dosage form leaves the stomach. Exemplary enteric coating materials include hydroxypropyl methyl cellulose acetate succinate, hydroxypropyl methyl cellulose phthalate, cellulose acetate phthalate, cellulose acetate trimellitate, carboxylic acid-functionalized polymethacrylates, and carboxylic acid-functionalized polyacrylate.

Compositions may be administered in a controlled release dosage form. In one such dosage form, the composition of the enzalutamide and polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the dispersion of enzalutamide and polymer. The aqueous-swollen matrix gradually erodes, swells, disintegrates or dissolves in the environment of use, thereby controlling the release of the dispersion to the environment of use.

In some embodiments, compositions are administered by or incorporated into a non-erodible matrix device.

In some embodiments, compositions are delivered using a coated osmotic controlled release dosage form. This dosage form has two components: (a) the core which contains an osmotic agent and the dispersion of enzalutamide and concentration-enhancing polymer; and (b) a non-dissolving and non-eroding coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, osmogen, or osmagent. The coating is in some embodiments, polymeric, aqueous-permeable, and has at least one delivery port.

In some embodiments, compositions are delivered via a coated hydrogel controlled release form having at least two components: (a) a core comprising the dispersion and a hydrogel, and (b) a coating through which the dispersion has passage when the dosage form is exposed to a use environment.

In some embodiments, a drug mixture is delivered via a coated hydrogel controlled release dosage form having at least three components: (a) a composition containing the dispersion, (b) a water-swellable composition wherein the water-swellable composition is in a separate region within a core formed by the drug-containing composition and the water-swellable composition, and (c) a coating around the core that is water-permeable, water-insoluble, and has at least one delivery port therethrough. In use, the core imbibes water through the coating, swelling the water-swellable composition and increasing the pressure within the core, and fluidizing the dispersion-containing composition. Because the coating remains intact, the dispersion-containing composition is extruded out of the delivery port into an environment of use.

In some embodiments, compositions may be administered as multiparticulates. Multiparticulates generally refer to dosage forms that comprise a multiplicity of particles that may range in size from about 10 µm to about 2 mm, more typically about 100 µm to 1 mm in diameter. Such multiparticulates may be packaged, for example, in a capsule such as a gelatin capsule or a capsule formed from an aqueous-soluble polymer such as HPMCAS, HPMC or starch or they may be dosed as a suspension or slurry in a liquid.

Such multiparticulates may be made by any known process, such as wet- and dry-granulation processes, extrusion/spheronization, roller-compaction, or by spray-coating seed cores. For example, in wet- and dry-granulation processes, the composition of enzalutamide and concentration-enhancing polymer is prepared as described above. This composition is then granulated to form multiparticulates of the desired size. Other excipients, such as a binder (e.g., microcrystalline cellulose), may be blended with the composition to aid in processing and forming the multiparticulates. In the case of wet granulation, a binder such as microcryscalline cellulose may be included in the granulation fluid to aid in forming a suitable multiparticulate.

In any case, the resulting particles may themselves constitute the multiparticulate dosage form or they may be coated by various film-forming materials such as enteric polymers or water-swellable or water-soluble polymers, or they may be combined with other excipients or vehicles to aid in dosing to patients.

The solid dispersion can be prepared by dissolving and/or suspending enzalutamide and the polymer in a pharmaceutically acceptable solvent, and removing the solvent. Pharmaceutically acceptable additives can be added to the solvent which dissolved and/or suspended enzalutamide.

The pharmaceutically acceptable solvent is not particularly limited, so long as enzalutamide can be an amorphous state in the presence of the polymer. Examples of the pharmaceutically acceptable solvent include ketones such as acetone, alcohols such as methanol, ethanol, or propanol, a mixture thereof, and a mixed solvent of water with one or more of these solvents. These pharmaceutically acceptable solvents may be used alone or as an appropriate combination of two or more thereof.

The amount of the pharmaceutically acceptable solvent is not particularly limited, so long as it can be dissolved and/or suspended enzalutamide. A 1- to 100-fold amount (w/w) of the pharmaceutically acceptable solvent, or a 5- to 20-fold amount (w/w) of the pharmaceutically acceptable solvent in other embodiments may be contained, with respect to the total weight of enzalutamide and the polymer.

A method of removing the pharmaceutically acceptable solvent is not particularly limited, so long as the solvent can be removed from the liquid in which enzalutamide and the polymer are dissolved and/or suspended. Examples of the method include spray drying, drying under reduced pressure, forced-air drying, and the like, and spray drying may be used in other embodiments.

The process of manufacturing the pharmaceutical composition or its pharmaceutical formulation is not particularly limited, so long as it can produce the desired pharmaceutical formulation by using an appropriate combination of the above methods or known methods per se. Specifically, for example, the solid dispersion is mixed with one additive, or two or more additives, and known methods per se are carried out to obtain tablets, powders, fine granules, granules, dry syrups, or capsules.

The process of manufacturing the pharmaceutical composition or its pharmaceutical formulation is not particularly limited, so long as it can produce the desired pharmaceutical formulation by using an appropriate combination of the above methods or known methods per se.

The pharmaceutical composition can be produced, for example, by any known process including the steps of blending, granulation, specific size controlling, tableting, film coating and the like.

For example, the solid pharmaceutical composition in the form of powders, fine granules, granules or dry syrups can be produced by a process including the steps of (1) mixing the solid dispersion with one additive or two or more additives using blender, and (2) granulating the resulting mixture by dry granulation using dry granulator. In a case where the above various pharmaceutical additives are used as needed, these pharmaceutical additives may be added at any stage, e.g., during step (1), between steps (1) and (2), or during step (2).

The specific size controlling method can be adjusted the particle size of the granules. For example, the size may be adjusted 50 µm to 500 µm, 100 µm to 300 µm in another embodiment, 100 µm to 250 µm in still another embodiment using a sizing machine.

The granules may each be adjusted to any suitable size by being subjected to a grinding step prior to the mixing step. In the grinding step, any apparatus or means may be used as long as it generally allows pharmaceutical grinding of the drug and/or the pharmaceutical additive(s). In the mixing step of the individual components, which is subsequent to grinding, any apparatus or means may be used as long as it generally allows pharmaceutical mixing of the individual components into a uniform state.

The granulated product is then tabulated to produce tablets. Any tableting technique may be used for this purpose as long as it generally allows pharmaceutical production of compression molded products. Examples include techniques in which a granulated product is tabulated in admixture with one additive, or two or more additives. Any type of tablet machine may be used for this purpose as long as it generally allows pharmaceutical production of compression molded products. Examples include a rotary tablet machine, a single-shot tablet machine and the like. The tablet hardness is set to, for example, 50 to 300 N, or alternatively, 80 to 250 N, taking into consideration handling in production, distribution, and the like of medicaments.

After tableting, the tablet surface may be coated with a film coating. Any technique may be used for this purpose as long as it generally allows pharmaceutical tablet coating. Examples include pan coating processes and the like. Any type of film coating agent may be used for this purpose as long as it is generally used as a pharmaceutical additive for pharmaceutical tablet coating. Film coating agents may be added alone or in combination as appropriate in suitable amounts.

In general, the coating rate is not limited in any way as long as the tablet surface can be coated.

Any method may be used to produce the pharmaceutical composition sdisclosed herein or a pharmaceutical formulation thereof, as long as it allows production of pharmaceutical formulations having the desired effects by the method described above or an appropriate combination of methods known per se.

Tablet Formulations

In some embodiments, for manufacture of a tablet dosage form of an enzalutamide/polymer dispersion, an enzalutamide/polymer dispersion containing 55-65 wt % enzalutamide is used. In some embodiments, a 60% A:HPMCAS-M dispersion is used. A useful tablet contains approximately 70% of its total weight as 60% A:HPMCAS-M dispersion, with the remainder inactive excipients, including a disintegrant. In some embodiments, a tablet comprises sodium starch glycolate (e.g., EXPLOTAB®) as a disintegrant. In some embodiments, a tablet comprises croscarmellose sodium (e.g., AC-DI-SOL®) as a disintegrant. In some embodiments, such tablets comprise 6 to 10 wt % disintegrant. In some embodiments, a tablet comprises 266.67 mg 60% A:HPMCAS-M dispersion, and 30.5 mg croscarmellose sodium, in a 381 mg tablet; this corresponds to a dispersion content of 70 wt % and a disintegrant content of 8 wt %.

In some embodiments, a tablet contains approximately 55-65% of its total weight as 60% A:HPMCAS-M dispersion, with the remainder inactive excipients, including a disintegrant. In some embodiments, sodium starch glycolate (e.g., EXPLOTAB®) as a disintegrant. In some embodiments, tablets contain croscarmellose sodium (e.g., AC-DI-SOU)) as a disintegrant. In some embodiments, such tablets comprise 6 to 10 wt % disintegrant. For example, in some embodiments, a tablet of this type may comprise 266.67 mg 60% A:HPMCAS-M dispersion, and 34 mg croscarmellose sodium, in a 425 mg tablet. This corresponds to a dispersion content of 62.7 wt % and a disintegrant content of 8 wt %.

In some embodiments, a tablet contains approximately 45-55% of its total weight as 60% A:HPMCAS-M dispersion, with the remainder inactive excipients, including a disintegrant. In some embodiments, sodium starch glycolate (e.g., EXPLOTAB®) or croscarmellose sodium (e.g., AC-DI-SOU)), is used. In some embodiments, a tablet comprises 6 to 10 wt % disintegrant. For example, in some embodiments a tablet of this type may comprise 266.67 mg 60% A:HPMCAS-M dispersion, and 40 mg croscarmellose sodium, in a 500 mg tablet. This corresponds to a dispersion content of 53.3 wt % and a disintegrant content of 8 wt %. Larger tablets may be made, providing they contain 266.67 mg 60% A:HPMCAS-M dispersion, and at least 6 wt % disintegrant; in some embodiments, 8 wt % disintegrant.

Tablets comprising enzalutamide/polymer dispersions may be prepared using wet granulation, dry granulation, or direct compression. In some embodiments, dry granulation or direct compression is used.

In some embodiments, tablets comprise 60% A:HPMCAS-M dispersion, the disintegrant croscarmellose sodium, and microcrystalline cellulose (e.g., AVICEL® PH102). In some embodiments, tablets comprise 60% A:HPMCAS-M dispersion, the disintegrant croscarmellose sodium, microcrystalline cellulose (e.g., AVICEL® PH102), and lactose 318 Fast-Flo. In some embodiments, tablets comprise 60% A:HPMCAS-M dispersion, the disintegrant croscarmellose sodium, microcrystalline cellulose (e.g., AVICEL® PH102), lactose 318 Fast-Flo, and silica (e.g., CAB-O-SILO). An example of a 500 mg tablet formulation, manufactured by direct compression, comprises:

53.3 wt % 60% A:HPMCAS-M dispersion;
8.0 wt % croscarmellose sodium;
19.0 wt % microcrystalline cellulose;
19.0 wt % fast-flo lactose;
0.5 wt % silica; and
0.25 wt % magnesium stearate.

It will be apparent that said exemplary tablet may be made larger or smaller, without significant effect on performance, by making small variations in the amount of each excipient, providing that the tablet contains sufficient 60% A:HPMCAS-M dispersion to provide a 160 mg dose of enzalutamide. In some embodiments of larger or smaller tables, the relative ratios of the five listed excipients remains approximately constant.

Compositions disclosed herein may be used to treat any condition which is subject to treatment by administering enzalutamide. Accordingly, compositions can be used to treat hyperproliferative disorders, such as prostate cancer (e.g., hormone-refractory prostate cancer, hormone-sensitive prostate cancer), breast cancer, and ovarian cancer, in a mammal (including a human being) by administering to a mammal in need of such treatment a therapeutically effective amount of a composition disclosed herein.

The in vitro dissolution test to evaluate enhanced drug concentration in aqueous solution can be conducted by (1) adding with agitation a sufficient quantity of control composition, that is, the crystalline enzalutamide alone, to the in vitro test medium, typically MFD or PBS solution, to determine the maximum concentration of the enzalutamide achieved under the conditions of the test; (2) adding with agitation a sufficient quantity of test composition (e.g., the enzalutamide and polymer) in an equivalent test medium, such that if all the enzalutamide dissolved, the theoretical concentration of enzalutamide would exceed the observed maximum concentration of enzalutamide by a factor of about 20; and (3) comparing the measured MDC and/or aqueous concentration versus time $AUC_{90}$ of the test composition in the test medium with the maximum concentration, and/or the aqueous concentration versus time $AUC_{90}$ of the control composition. In conducting such a dissolution test, the amount of test composition or control composition used is an amount such that if all of the enzalutamide dissolved, the test enzalutamide concentration would be at least about 20-fold that of the control enzalutamide concentration.

The concentration of dissolved enzalutamide is typically measured as a function of time by sampling the test medium and plotting enzalutamide concentration in the test medium vs. time so that the MDC can be ascertained. The MDC is taken to be the maximum value of dissolved enzalutamide measured over the duration of the test. The enzalutamide concentration versus time $AUC_{90}$ is calculated by integrating the concentration versus time curve over any 90-minute time period between the time of introduction of the composition into the aqueous use environment (time equals zero) and 270 minutes following introduction to the use environment (time equals 270 minutes). Typically, when the composition reaches its MDC rapidly, in less than about 30 minutes, the time interval used to calculate $AUC_{90}$ is from time equals zero to time equals 90 minutes. However, if the $AUC_{90}$ over any 90-minute time period described above of a composition meets the criteria of compositions described herein, then the composition is included in compositions of this disclosure. The time period 270 min is chosen because of its physiological relevance. Drug absorption in mammals generally occurs in the small intestine, and the small intestinal transit time in humans is approximately 4.5 hr, or 270 min.

To avoid large enzalutamide particulates which would give an erroneous determination, the test solution is either filtered or centrifuged. "Dissolved enzalutamide" is typically taken as that material that either passes a 0.45 micron syringe filter or, alternatively, the material that remains in the supernatant following centrifugation. Filtration can be conducted using a 13 mm, 0.45 micron polyvinylidine difluoride syringe filter, such as the TITAN' sold by Scientific Resources under the trademark TITAN'. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (+/−10-40%) than that obtained with the filter specified above but will still allow identification of dispersions. It is recognized that this definition of "dissolved enzalutamide" encompasses not only monomeric solvated enzalutamide molecules but also a wide range of species such as polymer/enzalutamide assemblies that have submicron dimensions such as enzalutamide aggregates, aggregates of mixtures of polymer and enzalutamide, micelles, polymeric micelles, colloidal particles, polymer/enzalutamide complexes, and other such enzalutamide-containing species that are present in the filtrate or supernatant in the specified dissolution test.

The membrane permeability test described in the Examples below is carried out as follows. A drug-permeable membrane is placed between feed and permeate reservoirs. A sufficient quantity of test composition is added to a feed test medium and placed in the feed reservoir, while a water immiscible organic solution, such as a 60/40 mixture of decanol/decane, is placed in the permeate reservoir. Samples are removed from the permeate reservoir and analyzed for the concentration of drug as a function of time. From these data the maximum flux of drug across the membrane is determined, as is the total drug recovery, defined as the percentage of the amount of drug which has crossed the membrane after 240 minutes. Further details of this membrane permeation test are disclosed in U.S. Pat. No. 7,611,630 B2.

Nothing in this specification should be considered as limiting the scope of this disclosure. All examples presented are representative and non-limiting. The above-described embodiments can be modified or varied, as appreciated by those skilled in the art in light of the above teachings. It is therefore to be understood that, within the scope of the claims and their equivalents, the embodiments disclosed herein can be practiced otherwise than as specifically described.

In the examples below, "Control 1" is crystalline enzalutamide, obtained as described in U.S. Pat. No. 7,709,517B2, in which this compound is called RD162'; and "Control 2" is a 4.23 mg/ml solution of enzalutamide in LABRASOL® (Caprylocaproyl polyoxylglycerides).

Example 1. Preparation of Amorphous Enzalutamide

Amorphous enzalutamide was prepared by spray-drying a 3 wt % solution of enzalutamide dissolved in acetone using a lab-scale spray drier. The lab-scale drier consisted of a 27.6-cm diameter spray drier having a diameter-to-height ratio of greater than 3. The lab-scale drier was equipped with a Schlick 2.0 pressure nozzle. Heated drying gas (nitrogen) was delivered to the drying chamber through a perforated plate to provide a uniform flow of drying gas through the drying chamber. To form amorphous enzalutamide, the spray solution was delivered to the nozzle at a flow rate of 20 g/min and a pressure of 110 psig. In the drying chamber, the atomized droplets were combined with the nitrogen drying gas, which entered the system at a flow rate of 470 g/min and a temperature of 100° C. The spray-dried particles, evaporated solvent, and drying gas were removed from the spray-drying chamber at a temperature of 45° C. through an outlet port and sent to a high-efficiency cyclone separator where the spray-dried particles were collected. The evaporated solvent and drying gas were then sent to a filter for removal of any remaining particles before discharge.

Example 2. Preparation of Enzalutamide Dispersions with Concentration Enhancing Polymers A solid amorphous dispersion of 25 wt % enzalutamide and 75 wt % HPMCAS was prepared using a spray drying process as follows. A spray solution was prepared by dissolving 1 wt % enzalutamide and 3 wt % HPMCAS-M in acetone. This solution was spray-dried using the lab-scale spray drier described in Example 1. The solution was delivered to a Schlick 2.0 pressure nozzle atomizer at a pressure of 114 psig. The spray solution was delivered to the spray drier at a flow rate of 20 gm/min. The nitrogen drying gas was delivered to the nozzle at 102° C. and at a flow rate of 470 g/min. The outlet temperature of the spray dryer was 46° C. The resulting spray dried particles were removed using a cyclone separator. The spray drying parameters are summarized in Table 2.1.

Additional dispersions were made using various polymers and formulations, as summarized in Table 2.1.

TABLE 2.1

Preparation conditions for spray-dried dispersions (SDDs) of enzalutamide with polymers.

| SDD Composition and (Dispersion Number) | Spray Dryer | Solids in Spray Soln. (%) | Run Size (gA) | Drying Gas $T_{in}$ (C. °) | Drying Gas $T_{out}$ (C. °) | Drying Gas Flow Rate (g/min) | Spray Solution Feed Rate (g/min) | Spray Nozzle | Nozzle Pressure (psi) |
|---|---|---|---|---|---|---|---|---|---|
| 25% A HPMCAS-M SDD (D1) | lab-scale drier | 4.0 | 6.4 | 102 | 46 | 470 | 20 | Schlick 2.0 | 114 |
| 25% A PVP-VA64 SDD (D2) | lab-scale drier | 4.0 | 1.5 | 112 | 46 | 470 | 20 | Schlick 2.0 | 111 |
| 60% A HPMCAS-M SDD (D3) | lab-scale drier | 8.0 | 9.0 | 109 | 47 | 470 | 25 | Schlick 2.0 | 109 |
| 25% A HPMCAS-M SDD (D4) | mini | 2.0 | 50 mg | 100 | 23 | 20 | 0.65 | 2-fluid* | |
| 40% A HPMCAS-M SDD (D5) | mini | 1.5 | 50 mg | 100 | 23 | 20 | 0.65 | 2-fluid | |
| 60% A HPMCAS-M SDD (D6) | mini | 1.0 | 50 mg | 100 | 23 | 20 | 0.65 | 2-fluid | |
| 80% A HPMCAS-M SDD (D7) | mini | 1.0 | 50 mg | 100 | 23 | 20 | 0.65 | 2-fluid | |
| 25% A HPMCAS-H SDD (D8) | mini | 2.0 | 50 mg | 100 | 23 | 20 | 0.65 | 2-fluid | |
| 40% A HPMCAS-H SDD (D9) | mini | 1.5 | 50 mg | 100 | 23 | 20 | 0.65 | 2-fluid | |
| 40% A PVP VA64 SDD (D10) | mini | 1.0 | 50 mg | 100 | 23 | 20 | 0.65 | 2-fluid | |
| 25% A HPMCAS-MG SDD (D11) | lab-scale drier | 8.0 | 10 | 107 | 44 | 510 | 22 | Schlick 2.0 | 106 |
| 60% A HPMCAS-MG SDD (D12) | lab-scale drier | 8.0 | 20 | 109 | 55 | 490 | 22 | Schlick 2.0 | 104 |
| 60% A HPMCAS-MG SDD (D13) | PSD-1 | 18.0 | 900 | 99 | 30 | 1750 | 230 | Spray Systems SK79-16 | 330-370 |
| 60% A HPMC-E3Prem SDD (D14) | mini | 1.5 | 100 mg | 105 | 23 | 20 | 0.65 | 2-fluid | |
| 60% A HPMCP-55 SDD (D15) | mini | 1.5 | 100 mg | 105 | 23 | 20 | 0.65 | 2-fluid | |
| 60% A Eudragit-L100 SDD (D16) | mini | 1.5 | 100 mg | 105 | 23 | 20 | 0.65 | 2-fluid | |

*2-fluid nozzle is a Spraying Systems 1650 liquid, 64 air cap, available from Spraying Systems Co. ®, Wheaton, IL
The "mini" spray-dryer consisted of an atomizer in the top cap of a vertically oriented 11-cm diameter stainless steel pipe.
The PSD-1 spray dryer is a Niro type XP Portable Spray-Dryer with a Liquid-Feed Process Vessel.

Example 3. PXRD Diffractograms of Spray-Dried Amorphous Drug and Enzalutamide/Polymer Dispersions, and Bulk Crystalline Drug The dispersions were analyzed by powder X-ray diffraction (PXRD) using an AXS D8 Advance PXRD measuring device (Bruker, Inc. of Madison, Wisconsin) using the following procedure. Samples (approximately 30 to 100 mg) were packed in Lucite sample cups fitted with Si(511) plates as the bottom of the cup to give no background signal. Samples were spun in the (p plane at a rate of 30 rpm to minimize crystal orientation effects. The x-ray source (KCu$_\alpha$, λ=1.54 Å) was operated at a voltage of 45 kV and a current of 3 mA. Data for each sample were collected over a period of 120 minutes in continuous detector scan mode at a scan speed of 8 seconds/step and a step size of 0.04°/step. Diffractograms were collected over the 2θ range of 4° to 40°.

The diffractograms in FIG. 1 demonstrate that spray-dried enzalutamide, a 25% A:PVP-VA64 SDD, a 25% A:HPMCAS-M SDD, and a 60% A:HPMCAS-MG SDD all are completely amorphous, characterized by the absence of sharp crystallographic x-ray peaks.

Example 4. In Vitro Dissolution of Enzalutamide Formulations and Controls

In vitro dissolution studies were carried out for a subset of the formulations whose manufacture is described in Example 2. These dissolution studies utilized the Microcentrifuge Dissolution Test described above. The formulations tested were amorphous enzalutamide, various enzalutamide/Polymer spray-dried dispersions (SDDs), and Controls 1 and 2. A dose of 200 µg/ml enzalutamide was chosen, in order to be 10 to 20 times higher than the solubility of crystalline enzalutamide, in order to evaluate the ability of formulations to achieve enzalutamide supersaturation and sustainment of supersaturation relative to crystalline drug. The dissolution medium was Model Fasted Duodenal Solution (MFDS), which consisted of an aqueous solution comprising 20 mM Na$_2$HPO$_4$, 47 mM KH$_2$PO$_4$, 87 mM NaCl, 0.2 mM KCl, at pH 6.5 and 290 mOsm/kg, additionally containing 7.3 mM sodium taurocholic acid and 1.4 mM of 1-palmitoyl-2-oleyl-sn-glycero-3-phosphocholine.

TABLE 4.1

Microcentrifuge dissolution test data for enzalutamide spray-dried dispersions (SDDs), amorphous enzalutamide, and controls.

| Formulation (Dispersion #) | Enzalutamide Concentration (µg/ml) | | | | | | |
|---|---|---|---|---|---|---|---|
| | 0 min | 4 min | 10 min | 20 min | 40 min | 90 min | 1200 min |
| 25% A HPMCAS-M SDD (D4) | 0.0 | 150 | 150 | 150 | 160 | 160 | 100 |
| 40% A HPMCAS-M SDD (D5) | 0.0 | 110 | 86 | 93 | 110 | 120 | 100 |
| 60% A HPMCAS-M SDD (D6) | 0.0 | 75 | 78 | 93 | 100 | 110 | 100 |
| 80% A HPMCAS-M SDD (D7) | 0.0 | 87 | 100 | 130 | 130 | 130 | 40 |
| 25% A HPMCAS-H SDD (D8) | 0.0 | 110 | 110 | 110 | 110 | 110 | 110 |
| 40% A HPMCAS-H SDD (D9) | 0.0 | 100 | 110 | 110 | 110 | 110 | 110 |
| 25% A PVP VA64 SDD (D2) | 0.19 | 110 | 110 | 110 | 110 | 110 | Not Done |
| 40% A PVP VA64 SDD (D10) | 0.0 | 100 | 100 | 110 | 110 | 110 | 40 |
| Amorphous (spray-dried) enzalutamide - BREC-0035-09B(V) | 0.0 | 61 | 100 | 100 | 110 | 120 | 30 |
| Crystalline enzalutamide (Control 1) | 0.0 | 1 | 3 | 5 | 6 | 7 | 9 |
| 4.23 mgA/mL enzalutamide in Labrasol (Control 2) | 0.0 | 170 | 180 | 170 | 170 | 170 | 190 |

TABLE 4.2

Microcentrifuge dissolution data (C$_{max}$ and AUC$_{90}$) for enzalutamide spray-dried dispersions (SDDs), amorphous enzalutamide, and controls.

| Sample Tested (Dispersion #) | C$_{max, 90}$[a] (µg/mL) | AUC$_{90}$[b] (min*µg/mL) |
|---|---|---|
| 25% A HPMCAS-M SDD (D4) | 160 | 13,600 |
| 40% A HPMCAS-M SDD (D5) | 120 | 9,200 |
| 60% A HPMCAS-M SDD (D6) | 110 | 8,500 |
| 80% A HPMCAS-M SDD (D7) | 130 | 11,200 |
| 25% A HPMCAS-H SDD (D8) | 110 | 9,800 |
| 40% A HPMCAS-H SDD (D9) | 110 | 9,700 |
| 25% A PVP VA64 SDD (D2) | 110 | 9,700 |
| 40% A PVP VA64 SDD (D10) | 110 | 9,800 |
| Amorphous (spray-dried) enzalutamide - BREC-0035-09B(V) | 120 | 9,500 |
| Crystalline enzalutamide (Control 1) | 7 | 500 |
| 4.23 mgA/mL enzalutamide in Labrasol (Control 2) | 180 | 15,200 |

[a]C$_{max, 90\ min}$ = maximum drug concentration through 90 minutes.
[b]AUC$_{90\ min}$ = area under the curve at 90 minutes.

The data in Tables 4.1 and 4.2 demonstrate that amorphous enzalutamide, a Labrasol solution of enzalutamide, and various spray-dried dispersions (SDDs) of enzalutamide with the polymers HPMCAS and PVP-VA64 all exhibit a large enzalutamide supersaturation when dissolved, relative to crystalline enzalutamide, in addition to the ability to maintain this supersaturation.

The AUC$_{90}$ values for the SDDs in Table 4.2 are all greater than 5 times the AUC$_{90}$ for crystalline enzalutamide (Control 1). The C$_{max}$ 90 values for the SDDs in Table 4.2 are all greater than 5 times the C$_{max}$ 90 for crystalline enzalutamide (Control 1).

Example 5. Glass Transition Temperatures (Tgs) as a Function of Relative Humidity Below Tg, an amorphous material is said to be in a "glassy" state in which molecular mobility is severely restricted. Above Tg, an amorphous material is in a state in which molecular mobility is increased significantly relative to the "glassy" state. Glass transition temperatures Tg were determined for amorphous enzalutamide, and for spray-dried dispersions (SDDs) of enzalutamide with HPMCAS-M or PVP-VA64, at <5% and 75% relative humidity (RH). Tgs were determined by modulated differential scanning calorimetry (mDSC), utilizing the following protocol. Samples (about 5 mg) were equilibrated at the desired RH overnight in an environmental chamber at ambient temperature. The samples were then loaded into pans and sealed inside the environmental chamber. The samples were analyzed on a Q1000 mDSC (TA Instruments, New Castle, Delaware). Samples were typically scanned over the temperature range of −40° C. to 180° C., at a scan rate of 2.5° C./min, and a modulation rate of ±1.5° C./min. The data sampling interval was 0.20 sec/point. The Tg was calculated based on half height.

Tg data are presented in Table 5.1. As is generally observed, Tg decreases with increasing RH because the amorphous material is plasticized by incorporated water vapor as the % RH increases. Generally, Tg decreases approximately linearly as % RH increases.

TABLE 5.1

T$_g$ as a Function of Relative Humidity (RH) for enzalutamide SDDs

| | T$_g$ (° C.) | |
|---|---|---|
| SDD Formulation (Dispersion #) | <5% RH | 75% RH |
| Amorphous (spray-dried) MDV-3100 | 88.5 | 64.0 |
| 80% A HPMCAS-M (D7) | 90.4 | 59.3 |
| 60% A HPMCAS-M (D6) | 87.1 | 52.0 |
| 25% A HPMCAS-M (D4) | 93.1 | 50.7 |
| 40% A HPMCAS-M (D5) | 91.3 | 51.9 |
| 25% A HPMCAS-H (D8) | 94.0 | 51.2 |
| 40% A HPMCAS-H (D9) | 91.1 | 51.2 |
| 40% A PVP VA64 (D10) | 103.3 | 34.9 |
| 25% A PVP VA64 (D2) | 105.5 | 30.8 |

In order to assure that a dispersion will maintain its amorphous character (and thus its capacity to supersaturate a solution), it is desirable to choose a dispersion composition whose Tg is above the temperatures at which the product may be stored. If the product is stored at a temperature above its Tg, the amorphous drug within the dispersion will be relatively mobile and can diffuse into drug-rich patches and can crystallize. This is undesirable. Typical storage challenge conditions dictated by the US Food and Drug Administration are 40° C./25% RH, 50° C./20% RH, and 40° C./75% RH. At 75% RH, 100% A spray-dried enzalutamide (pure amorphous enzalutamide) and the enzalutamide/HPMCAS SDDs exhibit Tgs which are above each of the FDA challenge conditions (30° C., 40° C., 50° C.). This is highly desirable, and these materials will not need protective packaging to protect them in high humidity environments.

The 25% A and 40% A enzalutamide dispersions with the concentration-enhancing polymer PVP-VA64 exhibit Tgs at 30.8° C. and 34.9° C., respectively. If enzalutamide/PVP-VA dispersions encounter storage conditions above their Tgs (such as 40° C.), they can possibly undergo undesirable change. Thus enzalutamide/PVP-VA dispersions should be stored in protective packaging (such as foil-foil blisters) which prevents ingress of water vapor into the dispersion.

Amorphous enzalutamide and MCV3100/HPMCAS dispersions have high Tgs.

Example 6. Particle Morphology of Amorphous Enzalutamide, and SDDs of Enzalutamide with HPMCAS and PVP-VA Scanning electron micrographs (SEMs) were obtained for samples before and after 1 day exposure to a 50° C./75% RH environment. These SEMs are presented in FIG. 2. After exposure of these samples to this challenging storage environment, no crystals were seen, indicative of the ability of these samples to maintain the amorphous character of enzalutamide. For three of the four samples, the 1 day storage challenge resulted in fusion of particles to form larger particles (100% A Spray-dried, 80% A:HPMCAS-MG, 40% A:PVPVA), with this effect being extreme for 40% A:PVPVA. Thus these three embodiments would require controlled storage conditions to maintain their efficacy. The 60% A:HPMCAS-MG SDD did not undergo fusion to larger particles over the 1 day storage challenge, and would not require controlled storage conditions to maintain efficacy.

In some embodiments, enzalutamide/HPMCAS SDDs have a drug content less than 80%.

Example 7. Capacity of Enzalutamide SDDs to Maintain Supersaturation after Suspension in Aqueous Media Drugs and drug formulations are sometimes dosed as aqueous suspensions, particularly for pediatric patients. The ability of various enzalutamide SDDs to retain their ability to maintain drug supersaturation in vitro was assessed by using the microcentrifuge dissolution test to measure drug dissolution after suspension in 0.5% methylcellulose in water for 2 hours. Methylcellulose is a standard viscosifying suspending agent which is used to maintain drug particles in suspension in oral suspension dosage forms. The table below presents in vitro dissolution performance before and after suspension in 0.5% methylcellulose.

TABLE 7.1

In vitro dissolution behavior of SDDs before and after suspension for 2 hr in aqueous 0.5% methylcellulose.

| Sample (Dispersion #) | $C_{max}$ 90 (mcg/ml) | $AUC_{90}$ (min · mcg/ml) | $AUC_{90}$ % of 0 Hr Value |
|---|---|---|---|
| 25% A: PVPVA64 (D2), 0 hr | 130 | 9,600 | — |
| 25% A: PVPVA64 (D2), 2 hr | 130 | 7,100 | 74 |
| 25% A: HPMCAS-MG (D17), 0 hr | 140 | 12,200 | — |
| 25% A: HPMCAS-MG (D17), 2 hr | 140 | 12,400 | 102 |
| 60% A: HPMCAS-MG (D3), 0 hr | 120 | 9,500 | — |
| 60% A: HPMCAS-MG (D3), 2 hr | 120 | 9,600 | 101 |
| Amorphous enzalutamide, 0 hr | 110 | 8,900 | — |
| Amorphous enzalutamide, 2 hr | 100 | 8,800 | 99 |

Amorphous enzalutamide and the SDDs with HPMCAS-MG maintained their ability to effect sustained supersaturation after suspension for 2 hr in aqueous methylcellulose. Incubation of a 25% A:PVPVA64 SDD for 2 hr in aqueous methylcellulose resulted in a 26% loss in supersaturation capacity, as measured by $AUC_{90}$.

Example 8. Membrane-Permeation (MP) Dissolution Test

The MP-dissolution test, whose details are described above, measures a capability of low solubility drug formulations which is not measured in the microcentrifuge dissolution test utilized in Examples 4 and 7. This test mimics an aspect of the in vivo situation in the GI tract. In the in vivo situation, it is generally accepted that free drug in solution (i.e. individual drug molecules dissolved in the GI medium without association with formulation components) is the species which is absorbed across the gastrointestinal wall into the bloodstream. As free drug is absorbed, the formulation must be capable of supplying more free drug for absorption. The membrane permeation test measures the amount of drug which crosses a polymeric membrane (as a model of the GI wall) over time, and thus reflects the ability of the formulation to resupply free drug in solution to be further passively transported across the polymeric membrane. In Table 8.1 below, Maximum Flux is the maximum observed rate of permeation across the polymeric membrane, based on the slope of the absorption curve over any period within the 240 minute duration of the experiment, normalized for membrane area. Total drug recovery is the % of the initial drug dose which has crossed the membrane when the test ended at 240 minutes.

TABLE 8.1

Membrane permeation tests for various enzalutamide SDDs and controls.

| Sample (Dispersion #) | Total Drug Recovery (%) | Maximum Flux (μg/cm$^2$ × min) |
|---|---|---|
| 25% A HPMCAS-M SDD (D4) | 87 | 3.3 |
| 40% A HPMCAS-M SDD (D5) | 83 | 2.8 |
| 60% A HPMCAS-M SDD (D6) | 87 | 2.8 |
| 80% A HPMCAS-M SDD (D7) | 69 | 2.0 |
| 25% A HPMCAS-H SDD (D8) | 91 | 3.3 |
| 40% A HPMCAS-H SDD (D9) | 86 | 2.6 |
| 25% A: PVP-VA64 SDD (D2) | 94 | 4.8 |

TABLE 8.1-continued

Membrane permeation tests for various enzalutamide SDDs and controls.

| Sample (Dispersion #) | Total Drug Recovery (%) | Maximum Flux (µg/cm² × min) |
|---|---|---|
| 40% A PVP VA64 SDD (D10) | 85 | 2.8 |
| Amorphous (spray-dried) enzalutamide | 56 | 1.3 |
| Crystalline enzalutamide (Control 1) | 28 | 0.4 |

These data (Table 8.1) demonstrate that amorphous enzalutamide and the SDDs with PVP-VA64 and HPMCAS are able to resupply free drug as free drug is transported across the polymeric membrane, at a rate (flux) and an extent superior to crystalline enzalutamide (Control 1). The SDDs perform better than amorphous enzalutamide in this respect. The lesser capacity of amorphous enzalutamide is likely due to slower dissolution than the SDDs, due to higher hydrophobicity. The data in Table 8.1 also indicate that HPMCAS-SDDs at 25% A, 40% A, and 60% A are superior to HPMCAS-SDDs at 80% A. Accordingly, in some embodiments enzalutamide/HPMCAS SDDs have an enzalutamide content less than 80% A. The data in Table 8.1 also indicate that enzalutamide SDDs with the M- and H-grades of HPMCAS perform equally well.

Example 9. Enzalutamide SDDs with the Polymers HPMC, HPMCP, and EUDRAGIT-L100®

A 60% A enzalutamide SDD was prepared with each of three polymers: hydroxypropylmethylcellulose (E3 Prem grade) (HPMC E3 Prem); hydroxymethylcellulose phthalate (grade with nominal phthalate content of 31%) (HPMCP-55); anionic 1:1 copolymer of methacrylic acid and methylmethacrylate (EUDRAGIT L100®). 60% A SDDs were prepared with these three polymers, using the mini spray drier, and the conditions shown in Table 2. Each of the three 60% A SDDs exhibited no sharp features in their PXRD diffactograms, and were thus amorphous.

The three 60% SDDs were tested in the in vitro microcentrifuge dissolution test, in addition to a 60% A HPMCAS-M dispersion and Control 1 (crystalline enzalutamide). Table 9.1 presents the dissolution data, and Table 9.2 presents $C_{max}$ and $AUC_{90}$ values derived from these dissolution data. All four SDDs exhibited enzalutamide supersaturation ($C_{max}$) and sustained supersaturation ($AUC_{90}$), relative to crystalline drug (Tables 9.1 and 9.2).

Table 9.1 shows that the enzalutamide SDDs with HPMCP-55 and with EUDRAGIT L100® exhibit decreased enzalutamide concentration in solution after the 40 minute time point, while SDDs with HPMCAS and HPMC E3 Prem do not. This is reflected in the in vitro $AUC_{90}$ data shown in Table 9.2.

TABLE 9.1

In vitro dissolution (microcentrifuge dissolution test) of various enzalutamide SDDs and crystalline enzalutamide.

| | Average µg/mL | | | | |
|---|---|---|---|---|---|
| Time (min) | 60% A: HPMCAS-M (Disp D12) | 60% A: HPMC (Disp D14) | 60% A: HPMCP (Disp D15) | 60% A: Eudragit (Disp D16) | Crystalline enzalutamide |
| 0 | 0.00 | 0.00 | 0.00 | 0.00 | 0.32 |
| 4 | 77.69 | 108.33 | 90.21 | 57.80 | 5.23 |
| 10 | 84.96 | 108.65 | 88.19 | 68.93 | 8.04 |
| 20 | 93.53 | 109.16 | 100.48 | 81.42 | 7.69 |
| 40 | 102.73 | 109.70 | 109.37 | 91.94 | 8.65 |
| 90 | 108.32 | 104.10 | 36.07 | 34.19 | 9.14 |
| 1200 | 58.82 | 36.29 | 21.75 | 23.66 | 12.12 |

TABLE 9.2

$C_{max}$ and $AUC_{90}$ values for various enzalutamide SDDs and crystalline enzalutamide (microcentrifuge dissolution test).

| Sample (Dispersion #) | $C_{max,\ 90\ min}$[a] (µg/mL) | $AUC_{90\ min}$[b] (min*µg/mL) |
|---|---|---|
| 60% A HPMCAS-M SDD (D12) | 110 | 8,800 |
| 60% A HPMC E3 Prem SDD (D14) | 110 | 9,500 |
| 60% A HPMCP-55 SDD (D15) | 110 | 7,400 |
| 60% A Eudragit-L100 SDD (D16) | 90 | 6,100 |
| Crystalline enzalutamide (Control 1) | 10 | 740 |

[a] $C_{max,\ 90\ min}$ = maximum drug concentration through 90 minutes.
[b] $AUC_{90\ min}$ = area under the curve at 90 minutes.

The membrane permeation test was carried out for 60% A enzalutamide SDDs with HPMCAS-M, HPMC E3 Prem, HPMCP-55, and Eudragit-L100, as described in Example 8. The data in Table 9.3 demonstrate that each of the four SDDs exhibit higher transmembrane flux than crystalline enzalutamide, and have the capacity to replace absorbed free drug. The data in Table 9.3 also demonstrate that the SDDs with HPMCAS-M and HPMC E3 Prem have greater transmembrane flux and thus greater capacity to replace absorbed free drug than do SDDs with HPMCP-55 and Eudragit-L100.

TABLE 9.3

Membrane-Permeation Test Results for SDDs and Crystalline enzalutamide

| Formulation (Dispersion #) | Maximum Flux ($\mu g/cm^2$-min) | Total Drug Recovery (%) |
|---|---|---|
| 60% A: HPMCAS-MG SDD (D12) | 3.7 | 81 |
| 60% A: HPMC E3 Prem SDD (D14) | 2.1 | 75 |
| 60% A: HPMCP HP55 SDD (D15) | 1.6 | 62 |
| 60% A: Eudragit L100 SDD (D16) | 1.7 | 55 |
| Crystalline enzalutamide (Control 1) | 0.4 | 35 |

Example 10

One Kilo-scale Batch of 60% A:HPMCAS-M SDD (Dispersion D18). A large batch of 60% A:HPMCAS-M SDD was prepared using a PSD-1 Spray-drier. Spray-drying conditions are presented in Table 10.1 (and in Table 2.1). Powder properties for the spray-dried material after tray-drying are also presented in Table 10.1.

TABLE 10.1

Spray-drying conditions and powder properties for 1 kilo-scale lot of 60% A: HPMCAS-M enzalutamide SDD (Dispersion D18).

| SPRAY-DRYING CONDITIONS | |
|---|---|
| Solids in spray solution | 18.0% |
| Run size | 900 g enzalutamide |
| Run time | 36 min |
| Drying gas $T_{in}$ | 100 ± 10° C. |
| Drying gas $T_{out}$ | 30 ± 5° C. |
| Drying gas flow rate | 1750 ± 300 g/min |
| Spray solution feed rate | 230 ± 30 g/min |
| Spray Systems SK79-16 nozzle pressure | 370 ± 100 psi |
| SDD PARTICLE PROPERTIES | |
| Powder bulk density | 0.33 g/cc |
| Powder tapped density | 0.42 g/cc |
| Volume Mean Diameter | 30 μm |
| DV10 | 9 μm |
| DV50 | 25 μm |
| DV90 | 59 μm |
| Span [(DV90-DV10)/DV50] | 2.0 (unit-less) |

Example 11

Preparation of enzalutamide drug/polymer dispersions by hot melt extrusion (HME).

HME dispersions were produced using dry-powder blends of enzalutamide and HPMCAS-M or PVP VA at three different drug loadings: 25% A, 40% A, and 60% A. Using a volumetric powder feeder, the blends were fed at a controlled rate to a 7.5-mm MP&R™ Model ME7.5 Twin-Screw Extruder (MP&R, Hackensack, NJ). The extruder is capable of reaching 210° C. and is equipped with a ⅛-inch cylindrical die. Extrudates were milled by hand using a mortar and pestle for subsequent testing. For a variety of extrusion runs, Table 11.1 presents the extrusion temperature, the crystallinity of the dispersion (amorphous is desired), and the glass transition temperature (Tg) measured by DSC.

TABLE 11.1

Extrusion temperature, and extrudate properties after milling with mortar and pestle

| Formulation (Dispersion #) | Control Temp.[a] (° C.) | Crystallinity by PXRD & Differential Scanning Calorimetry | $T_g$ (° C.) |
|---|---|---|---|
| 25% A: PVP-VA64 (D19) | 150 | Amorphous | 104 |
| 25% A: PVP-VA64 (D20) | 195 | Amorphous | 104 |
| 40% A: PVP-VA64 (D21) | 195 | Amorphous | 103 |
| 60% A: PVP-VA64 (D22) | 170 | Crystalline | 103 |
| 60% A: PVP-VA64 (D23) | 190 | Amorphous | 99 |
| 25% A: HPMCAS-M (D24) | 170 | Partially Crystalline* | 93 |
| 25% A: HPMCAS-M (D25) | 190 | Partially Crystalline | 95 |
| 25% A: HPMCAS-M (D26) | 195 | Partially Crystalline | 95 |
| 40% A: HPMCAS-M (D28) | 195 | Partially Crystalline | 90 |
| 40% A: HPMCAS-M (hot plate)[b] (D29) | 220 | Amorphous | 88 |
| 60% A: HPMCAS-M (D30) | 170 | Crystalline | — |

*Partially Crystalline means that while a Tg was observed, a crystalline drug melt peak was also observed. The PXRD showed evidence that some crystals were present. Controls were not performed to identify the amount of drug that was amorphous or crystalline.
[a]This is the control temperature for the terminal extruder barrels and the die. The actual product temperature is higher in the extruder due to additional frictional heat. It is difficult to measure the actual product temperature but was done using a temperature probe during the preparation of Dispersion D26. In that case, the extruder control temperature was 195° C. and the product temperature was measured at approximately 215° C.
[b]This sample was prepared on a hot plate at a temperature higher than was possible using the MP&R extruder.

The results in Table 11.1 demonstrate that amorphous enzalutamide:PVP-VA64 dispersions can be prepared by HME at 25% A and 40% A. Amorphous 60% A:PVP-VA64 dispersions can also be prepared if the temperature is held at 190° C. enzalutamide dispersions with HPMCAS-M were crystalline or partially crystalline, when prepared at the temperatures possible on the extruder used. Preparation at 220° C. on a hot plate resulted in an amorphous 40% A:HPMCAS-M dispersion. Preparation of HME dispersions of MDC3100 with HPMCAS at temperatures above 200° C. is non-optimal because HPMCAS degrades in this temperature range.

Dissolution of enzalutamide/polymer dispersions prepared by HME was evaluated using the microcentrifuge dissolution test, after dispersions were sieved to give various particle size ranges. Dissolution results are presented in Table 11.2.

TABLE 11.2

Microcentrifuge dissolution test results for enzalutamide dispersions prepared by hot melt extrusion. The total amount of sample dosed was 200 mcg per ml of dissolution medium. The dissolution medium was Model Fasted Duodenal Solution (MFDS) (0.5 wt % NaTC/POPC in PBS, pH 6.5, 290 mOsm). Results for SDDs of similar composition are presented for comparison.

| Sample (Dispersion #) | $C_{max90}{}^{a}$ (μg/mL) | $AUC_{90}{}^{b}$ (min * μg/mL) |
|---|---|---|
| 25% A HPMCAS-M SDD (D11) | 130 | 11,000 |
| 25% A HPMCAS-M HME dispersion (150 to 355 μm) (D26) | 110 | 6,000 |

TABLE 11.2-continued

Microcentrifuge dissolution test results for enzalutamide dispersions prepared by hot melt extrusion. The total amount of sample dosed was 200 mcg per ml of dissolution medium. The dissolution medium was Model Fasted Duodenal Solution (MFDS) (0.5 wt % NaTC/POPC in PBS, pH 6.5, 290 mOsm). Results for SDDs of similar composition are presented for comparison.

| Sample (Dispersion #) | $C_{max90}{}^a$ (µg/mL) | $AUC_{90}{}^b$ (min * µg/mL) |
|---|---|---|
| 25% A HPMCAS-M HME dispersion (50 to 150 µm) (D26) | 140 | 10,700 |
| 25% A HPMCAS-M HME dispersion (<50 µm) (D26) | 140 | 11,600 |
| 40% A HPMCAS-MG SDD (D31) | 110 | 9,100 |
| 40% A HPMCAS-MG HME dispersion (150 to 355 µm) (D28) | 40 | 2,300 |
| 40% A HPMCAS-MG HME dispersion (50 to 150 µm) (D28) | 80 | 6,200 |
| 40% A HPMCAS-MG HME dispersion (<50 µm) (D28) | 110 | 8,800 |
| 25% A PVP VA SDD (D2) | 130 | 9,700 |
| 25% A PVP VA HME dispersion (150 to 355 µm) (D20) | 90 | 6,400 |
| 25% A PVP VA HME dispersion (50 to 150 µm) (D20) | 110 | 7,900 |
| 25% A PVP VA HME dispersion (<50 µm) (D20) | 130 | 9,000 |
| 40% A PVP VA SDD (D10) | 110 | 7,500 |
| 40% A PVP VA HME dispersion (150 to 355 µm) (D21) | 60 | 4,700 |
| 40% A PVP VA HME dispersion (50 to 150 µm) (D21) | 100 | 8,200 |
| 40% A PVP VA HME dispersion (<50 µm) (D21) | 130 | 8,500 |

$^a C_{max90}$ = maximum drug concentration through 90 minutes
$^b AUC_{90}$ = area under the time/concentration curve at 90 minutes The data in Table 11.2 demonstrate that there is a particle size effect for supersaturation using HME-prepared dispersions of enzalutamide. HME dispersions with HPMCAS or PVP-VA, with a particle size <50 µm, are as efficacious as SDDs of identical composition. In some cases, HME dispersions with particle size 50-150 µm are also similar in efficacy to SDDs of identical composition. HME dispersions with particle size 150-355 µm are generally less efficacious than SDDs in achieving and maintaining supersaturation of enzalutamide.

Example 12. Relative Bioavailability of Enzalutamide Amorphous Drug and Spray-Dried Dispersion Formulations in Rats Five groups of jugular vein-cannulated CD® rats (n=6 per group) were dosed five enzalutamide formulations by oral gavage, at a dose of 20 mg/kg, in a volume of 2 ml/kg. Blood samples were obtained at 1, 3, 6, 12, 24, 36, 48, 60, and 72 hr post-dose.

The analytes, enzalutamide, MDPC0002, and MDPC0001 and internal standards (IS), N-$^{13}$CD$_3$-enzalutamide, MDPC0002-$^{13}$CD$_3$, and MDPC0001-$^{13}$CD$_3$ were extracted from 0.050 µL of rat plasma by a liquid-liquid extraction procedure. Internal standard working solution (25.0 µL) was added to all wells except the matrix blank. A 25.0-µL volume of acetonitrile was added all matrix blank samples. After adding 200 µL of 5% sodium bicarbonate in water buffer solution, the plate was vortexed for approximately 10 seconds. A Tomtec Quadra 96-well pipettor was used to add 1.050 mL of methyl tert-butyl ether (MTBE) to all wells, mixed, and approximately 1.00 mL of the organic layer was transferred to a clean 96-well plate. The samples were evaporated under heated nitrogen and reconstituted with 250 µL of 0.1% formic acid in methanol/water (40:60, v/v). The plate was covered and gently vortexed for approximately seconds. The extracts were chromatographed under reverse phase conditions on an ACE 5 C18 HPLC 5 µm, 2.1×30 mm column. The compounds were detected and quantified by tandem mass spectrometry in positive ion mode on an MDS Sciex API 3000 equipped with a Turbo IONSPRAY® probe. Calibration curves were obtained by performing a linear regression (weighted $1/x^2$) of the data from the calibration standards.

Plasma enzalutamide concentration vs. time curves were prepared, and values for the following parameters were determined. $C_{max}$ is the highest enzalutamide concentration observed for each rat. Tmax is the time that $C_{max}$ is first achieved. $AUC_{0-72}$ is the area under the plasma enzalutamide concentration vs. time plot out to 72 hr post-dosing. Pharmacokinetic data for the formulations studied are presented in Table 12.1.

TABLE 12.1

Mean pharmacokinetic parameters (± standard deviation) in rats for enzalutamide formulations. Crystalline drug, amorphous drug, and SDDs were dosed in suspension in a 0.5% methylcellulose vehicle.

| enzalutamide Formulation | $C_{max}$ (µg/ml) | Tmax (hr) | $AUC_{0-72}$ (µg · hr/ml) |
|---|---|---|---|
| Crystalline drug (Control 1) | 3.53 ± 0.66 | 6.05 ± 0.92 | 72.7 ± 18.4 |
| Solution in Labrasol (4.23 mg/ml) (Control 2) | 10.1 ± 1.38 | 5.86 ± 0.99 | 201 ± 42.9 |
| Spray-dried amorphous drug | 7.14 ± 0.97 | 2.55 ± 0.57 | 121 ± 16.4 |
| 25% A: HPMCAS-M | 10.8 ± 1.63 | 2.96 ± 0.65 | 171 ± 40.2 |
| 60% A: HPMCAS-M | 10.3 ± 1.66 | 3.30 ± 0.77 | 196 ± 39.6 |

These data demonstrate that dosing a suspension of amorphous enzalutamide results in a higher $C_{max}$ and AUC than after dosing a suspension of crystalline drug (Control 1).

Even greater improvement is observed after dosing a Labrasol solution, a 25% A:HPMCAS-M SDD, or a 60% A:HPMCAS-M SDD.

The $AUC_{0-72}$ data demonstrate that the 25% A:HPMCAS-M and 60% A:HPMCAS-M dispersions give higher bioavailability than the spray-dried amorphous drug. The 60% A:HPMCAS-M dispersion is equivalent in $C_{max}$ and $AUC_{0-72}$ to the Labrasol solution.

Example 13. Relative Bioavailability of Enzalutamide Amorphous Drug and Hot Melt Extrusion (HME) Dispersion Formulations in Rats Six groups of jugular vein-cannulated CD® rats (n=6 per group) were dosed six enzalutamide formulations by oral gavage, at a dose of 20 mg/kg, in a volume of 2 ml/kg, with the exception of one group which was dosed intravenously via tail vein. Blood samples were obtained at 1, 3, 6, 12, 24, 36, 48, 60, and 72 hr post-dose.

The analytes, enzalutamide, MDPC0002, and MDPC0001 and internal standards (IS), N-$^{13}$ CD$_3$-enzalutamide, MDPC0002-$^{13}$CD$_3$, and MDPC0001-$^{13}$ CD$_3$ were extracted from 0.050 µL of rat plasma by a liquid-liquid extraction procedure. Internal standard working solution (25.0 µL) was added to all wells except the matrix blank. A 25.0-µL volume of acetonitrile was added all matrix blank samples. After adding 200 µL of 5% sodium bicarbonate in water buffer solution, the plate was vortexed for approximately 10 seconds. A Tomtec Quadra 96-well pipettor was used to add 1.050 mL of methyl tert-butyl ether (MTBE) to all wells, mixed, and approximately 1.00 mL of the organic layer was transferred to a clean 96-well plate. The samples were evaporated under heated nitrogen and reconstituted with 250 µL of 0.1% formic acid in methanol/water (40:60, v/v). The plate was covered and gently vortexed for approximately seconds. The extracts were chromatographed under reverse phase conditions on an ACE 5 C18 HPLC 5 µm, 2.1×30 mm column. The compounds were detected and quantified by tandem mass spectrometry in positive ion mode on an MDS Sciex API 3000 equipped with a Turbo IONSPRAY® probe. Calibration curves were obtained by performing a linear regression (weighted $1/x^2$) of the data from the calibration standards.

Plasma enzalutamide concentration vs. time curves were prepared, and values for the following parameters were determined. $C_{max}$ is the highest enzalutamide concentration observed for each rat. Tmax is the time that $C_{max}$ is first achieved. $AUC_{0-72}$ is the area under the plasma enzalutamide concentration vs. time plot out to 72 hr post-dosing. Pharmacokinetic data for the formulations studied are presented in Table 13.1.

TABLE 13.1

Mean $AUC_{0-inf}$ and % Bioavailability in rats for enzalutamide formulations.
Crystalline drug, amorphous drug, and HME dispersion formulations were dosed in suspension in a 0.5% methylcellulose vehicle. For intravenous dosing, enzalutamide was dissolved in 50% polyethyleneglycol-400/20% ethanol (200 proof)/30% sterile water for injection (USP), and was dosed via tail vein.

| enzalutamide Formulation | Mean $AUC_{0-inf}$ (µg · hr/ml) | Bioavailability (%)* |
|---|---|---|
| Intravenous (IV) | 231 | — |
| Crystalline drug (Control 1) | 62.6 | 27.1 |
| Solution in Labrasol (4.23 mg/ml) (Control 2) | 225 | 97.4 |
| Spray-dried amorphous drug | 132 | 57.1 |
| 25% A: PVP-VA64 HME dispersion | 167 | 72.3 |
| 60% A: PVP-VA64 HME dispersion | 142 | 61.5 |
| 25% A: HPMCAS HME dispersion | 187 | 81.0 |

*Bioavailability = Mean $AUC_{0-inf}$/IV Mean $AUC_{0-inf}$. For example, 62.6/231 = 27.1%

These data demonstrate that dosing a suspension of amorphous enzalutamide results in a higher AUC than after dosing a suspension of crystalline drug (Control 1). Even greater improvement is observed after dosing HME dispersions of enzalutamide with the polymers PVP-VA64 and HPMCAS. The HME dispersion with HPMCAS gave a higher bioavailability than the dispersions with PVP-VA64.

Example 14. Tablets Containing Enzalutamide/Polymer Spray-Dried Dispersions

Enzalutamide tablets were prepared by direct compression, from the formulation in Table 14.1.

TABLE 14.1

Tablet composition.

| Component | Quantity (mg/tablet) |
|---|---|
| 60% A enzalutamide/HPMCAS-M SDD | 266.7 |
| Colloid silicon dioxide (Cab-O-Sil M5P) | 2.5 |
| Microcrystalline cellulose (Avicel PH102) | 94.8 |
| Lactose monohydrate, spray-dried (Fast Flo 316) | 94.7 |
| Croscarmellose sodium (Ac-Di-Sol) | 40.0 |
| Magnesium stearate | 1.3 |
| TOTAL | 500.0 |

The following procedure was used to form the tablets. First, the solid amorphous dispersion was added to an appropriate container. A portion of the solid amorphous dispersion (approximately 3 to 10 times the weight of colloidal silicon dioxide) was added to an LDPE bag containing the colloidal silicon dioxide. The SDD was manually mixed with the silicon dioxide for approximately 2 minutes. The mixture was passed through a No. 30 mesh screen, and added to the container. The mixture was blended for 15 minutes at 12 rpm using a Turbula mixer. Microcrystalline cellulose, lactose monohydrate, and croscarmellose sodium were added to the container, and the mixture was blended for 15 minutes.

Next, the mixture was subjected to high-shear mixing by passing it through a Comil 197 equipped with a 0.032-inch screen and 1601 impeller (impeller speed 1000 rpm). Since the Comil has a chamber diameter of 2.2 inches, the Froude Number for this high-shear mixing is about 125. The milled material was added to a container. A portion (approximately 3 to 10 times the weight of magnesium stearate) was added to an LDPE bag containing the magnesium stearate. The material was manually mixed with the magnesium stearate for approximately 30 seconds to 2 minutes, passed through a No. 20 mesh screen, and added to the container. The mixture was blended for 5 minutes at 12 rpm using a Turbula mixer.

Tablets were compressed using a rotary single-layer press, with 13/32" standard round convex tooling. Tablets weighed 500 mg each, with a hardness of 12 to 16 kP.

Carr's Index Testing

The flowability for Example 14 tablet blend, and for the dispersion alone, was evaluated using the Carr's index calculated from bulk and tap density. First, bulk density is measured using a graduated cylinder. The empty cylinder is weighed, the material is added, the final weight and volume are measured, and bulk density is calculated as shown below.

Bulk Density=Weight of Sample($g$)÷Volume of Sample($cc$)

To measure the tapped density, the sample in the cylinder above is placed in a VanKel tap density instrument, set for 2000 cycles. The ending volume is recorded, and the tapped density is calculated as shown below.

Tapped Density=Weight of Sample($g$)÷Volume of Sample after2000$Tap$ Cycles($cc$)

Carr's index was determined using the following equation $$C = 100 \times \left(1 - \frac{\rho_B}{\rho_T}\right)$$

where $\rho_B$ is equal to the bulk density and P T is equal to the tapped density. The results are shown below in Table A.

TABLE A

Carr's Index

| Formulation | Carr's Index |
|---|---|
| 60% enzalutamide:HPMCAS-M SDD | 33.3% |
| Example 14 tablet blend (made with colloidal silicon dioxide and high-shear mixing) | 24.2% |

The lower Carr's index of the formulation of Example 14 demonstrates improved flow properties of the dispersion, which enables tablet formation using a direct compression Process.

Example 15. Human Pharmacokinetics Study

A randomized, two-period crossover pilot bioequivalence and food effect study was carried out in humans. This study compared two formulations. The reference formulation was a liquid-filled, soft gelatin capsule containing 40 mg enzalutamide dissolved in Labrasol; four such capsules are required to deliver a 160 mg dose. The test formulation was a tablet containing 160 mg enzalutamide in the form of a 60% A:HPMCAS-M spray-dried dispersion. The liquid-filled capsule formulation had previously been used in clinical studies in castration-resistant prostate cancer. The four-capsule regimen is inconvenient because of the number of capsules that must be taken, particularly in the light of the fact that cancer patients have to take multiple drugs. The objectives of the human pharmacokinetics study were as follows:
1. To evaluate the bioequivalence of two oral formulations of enzalutamide following a single 160 mg dose in healthy male subjects under fasted conditions;
2. To evaluate the bioequivalence of two oral formulations of enzalutamide following a single 160 mg dose in healthy male subjects under fed conditions;
3. To assess the effects of food on the rate and extent of absorption of two oral formulations following a single 160 mg dose in healthy male subjects;
4. To evaluate the safety and tolerability of two oral formulations of enzalutamide following a single 160 mg dose in healthy male subjects under fasted or fed conditions.

Figure 8:
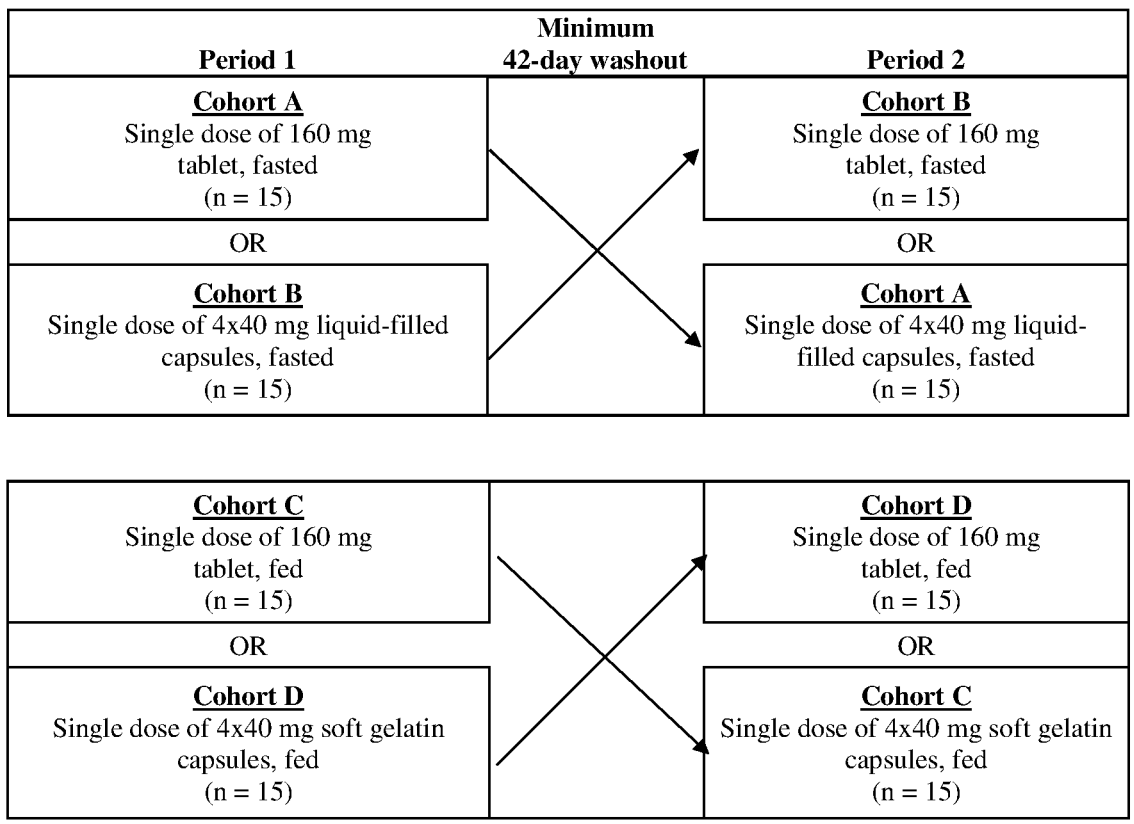
FIG. 8 shows the division of sixty healthy adult male subjects into four cohorts in Example 15.

Sixty healthy adult male subjects were divided into four cohorts as shown in FIG. 8.

The fasted conditions involved an overnight fast from food (minimum 10 hours) prior to dosing, and the fed conditions involved a standard high-fat, high-calorie meal that was ingested within 30 minutes prior to dosing. The high-fat, high-calorie meal was described in "US FDA Guidance for Industry: Food Effect Bioavailability and Fed Bioequivalence Studies (December 2002)." In both the fasted and fed conditions, the clinical research personnel administered the study medication at approximately 0800 hours with ambient temperature water to a total volume of about 240 mL. Subjects were required to swallow the study medication whole and not chew the medication prior to swallowing. The subjects were required to refrain from drinking beverages other than water during the first 4 hours after dosing. Water was allowed except 1 hour pre and post dose. Lunch was served ~4 hours post dose, and dinner was served ~9 to 10 hours post dose.

Blood samples for pharmacokinetics determinations were collected in each period as follows:
Day 1: pre-dose (0 hr) and post-dose 15, 30, and 45 minutes; and at 1, 2, 3, 4, 6, 8, and 12 hours;
Day 2: 0 and 12 hours; Days 3, 5, 7, 14, 21, 28, 35, and 42: 0 hours.

Plasma isolated from the whole blood samples was analyzed for concentrations of enzalutamide and its metabolites MDPC0001 and MDPC0002 using a sensitive, specific, and validated assay based on liquid chromatography and tandem mass spectroscopy (LC/MS/MS). The analytes, enzalutamide, MDPC0002, and MDPC0001 and internal standards (IS), N 13CD3 enzalutamide, MDPC0002 13CD3, and MDPC0001-13CD3 were extracted from 0.050 µL of plasma by a liquid extraction procedure. Internal standard working solution (25.0 µL) was added to all wells except the matrix blank. A 25.0-µL volume of acetonitrile was added all matrix blank samples. After adding 200 µL of 5% sodium bicarbonate in water buffer solution, the plate was vortexed for approximately 10 seconds. A Tomtec Quadra 96-well pipettor was used to add 1.050 mL of methyl tert-butyl ether (MTBE) to all wells, mixed, and approximately 1.00 mL of the organic layer was transferred to a clean 96-well plate. The samples were evaporated under heated nitrogen and reconstituted with 250 µL of 0.1% formic acid in methanol/water (40:60, v/v). The plate was covered and gently vortexed for approximately 10 seconds. The extracts were chromatographed under reverse phase conditions on an ACE 5 C18 HPLC 5 µm, 2.1×30 mm column. The compounds were detected and quantified by tandem mass spectrometry in positive ion mode on an MDS Sciex API 3000 equipped with a Turbo IONSPRAY® probe. Calibration curves were obtained by performing a linear regression (weighted 1/x2) of the data from the calibration standards.

A summary of pharmacokinetic parameters is presented in Table 15.1.

TABLE 15.1

Analysis of Formulation Bioequivalence: Geometric Mean (CV %) Plasma Enzalutamide Pharmacokinetic Parameter Values by Treatment and Food Condition A. Comparison of Tablet and Capsule Formulations under Fasted Conditions

| Pharmacokinetic Parameters (Units)[a] | Tablet Formulation, Fasted Conditions (Test) | Liquid-Filled Soft Gelatin Capsule Formulation, Fasted Conditions (Reference) | Ratio[b] (%) | 90% Confidence Interval (%) Lower | Upper |
|---|---|---|---|---|---|
| n | 28 | 29 | — | — | — |
| $AUC_{Day1-7}$ (µg · h/mL) | 177 (24) | 185 (25) | 95 | 92 | 97 |
| $AUC_{0-t}$ (µg · h/mL) | 255 (29) | 269 (30) | 95 | 92 | 97 |
| $AUC_{0-inf}$ (µg · h/mL) | 263 (28) | 278 (29) | 94 | 92 | 97 |
| $C_{max}$ (µg/mL) | 2.98 (24) | 5.16 (20) | 57 | 54 | 62 |
| $t_{max}$[c] (h) | 4.00 (2.00-6.00) | 1.00 (0.75-3.00) | — | — | — |
| $t_{1/2}$ (days) | 3.45 (36) | 3.67 (32) | — | — | — |

B. Comparison of Tablet and Capsule Formulations under Fed Conditions

| Pharmacokinetic Parameters (units) | Tablet Formulation, Fed Conditions (Test) | Liquid-Filled Soft Gelatin Capsule Formulation, Fed Conditions (Reference) | Ratio[d] (%) | 90% Confidence Interval (%) Lower | Upper |
|---|---|---|---|---|---|
| n | 15 | 15 | — | — | — |
| $AUC_{Day1-7}$ (µg · h/mL) | 191 (20) | 187 (19) | 102 | 91 | 114 |
| $C_{max}$ (µg/mL) | 2.96 (25) | 3.86 (35) | 77 | 65 | 91 |
| $t_{max}$[c] (h) | 1.00 (4.00-24.00) | 2.00 (0.50-6.00) | — | — | — | n = total number of subjects contributing to the summary statistics for PK parameters
[a]Area under the plasma concentration-time profile from time zero to Day 7 ($AUC_{Day1-7}$), AUC from time zero to the last measurable concentration ($AUC_{0-t}$), AUC from time zero to infinity ($AUC_{0-inf}$), maximum plasma concentration ($C_{max}$), and time to maximum plasma concentration ($t_{max}$).
[b]Ratio of least squares means (Test/Reference) based on crossover-treatment bioequivalence statistical tests.
[c]Median (range).
[d]Ratio of least squares means (Test/Reference) based on parallel-treatment bioequivalence statistical tests.

The analysis showed the extent of oral bioavailability for the Test and Reference formulations to be equivalent, the AUCs for the two formulations being essentially the same regardless of food conditions (fasted or fed).

Example 16

After 1 part by weight of enzalutamide and 3 parts by weight of hydroxypropylmethylcellulose acetate succinate (HPMCAS-MG,Shin-Etsu Chemical Co.,Ltd) were dissolved in acetone, a spray dryer (QSD-0.8-CC, GEA) was used to obtain a solid dispersion.
After the solid dispersion was mixed with calcium hydrogen phosphate hydrate, croscarmellose sodium and magnesium stearate by mortar and pestle, the mixture was formed into tablets by using an oil press tableting machine to obtain a tablet containing the solid dispersion at 12 kN of tableting pressure. The formulation is shown in Table 16.

Example 17

After 1 part by weight of enzalutamide and 3 parts by weight of hydroxypropylmethylcellulose acetate succinate were dissolved in acetone, a spray dryer (QSD-0.8-CC, GEA) was used to obtain a solid dispersion.
After the solid dispersion was mixed with calcium hydrogen phosphate hydrate, croscarmellose sodium and magnesium stearate, the mixture was formed into granules using dry granulation machine (roller compactor, TF-MINI, FRE-UND). After the resulting granules were mixed with croscarmellose sodium and magnesium stearate, the mixture was formed into tablets using a rotary tableting machine to obtain a tablet containing the solid dispersion. After tableting, the tablet was filmcoated by using filmcoating machine (HCT-30 Hi coater 30, FREUND). The formulation is shown in Table 16.

TABLE 16

| component | Example 16 | Example 17 | Example 18 | Example 21 |
|---|---|---|---|---|
| enzalutamide | 80.0 | 80.0 | 80.0 | 160 |
| hydroxypropylmethyl-cellolose acetate succinate | 240.0 | 240.0 | 160.0 | 106.7 |
| calcium hydrogen phosphate hydrate | 160.6 | 160.6 | 240.6 | — |
| colloidal silicon dioxide | — | — | — | 2.5 |
| microcrystalline cellulose | — | — | — | 94.8 |
| lactose monohydrate | — | — | — | 94.7 |
| croscarmellose sodium | 54.0 | 54.0 | 54.0 | 40.0 |
| magnesium stearate | 5.4 | 5.4 | 5.4 | 1.30 |
| filmcoating agent | — | 16.2 | — | 17.5 |
| total (mg) | 540.0 | 556.2 | 540.0 | 517.5 |
| tablet size | 14.8 mm × 7.8 mm | | — | — |

Example 18

After 1 part by weight of enzalutamide and 2 parts by weight of hydroxypropylmethylcellulose acetate succinate were dissolved in acetone, a spray dryer (QSD-0.8-CC, GEA) was used to obtain a solid dispersion. Further, a tablet was prepared as the same method as Example 16. The formulation is shown in Table 16.

Example 19

A solid dispersion, which comprises 1 part by weight of enzalutamide and 1.5 part by weight of hydroxypropylmethylcellulose acetate succinate, was prepared as the same method as Example 18.

Example 20

A solid dispersion, which comprises 1 part by weight of enzalutamide and 1 part by weight of hydroxypropylmethylcellulose acetate succinate, was prepared as the same method as Example 18.

Example 21

A solid dispersion, which comprises 1 part by weight of enzalutamide and 0.67 part by weight of hydroxypropylmethylcellulose acetate succinate, was prepared as the same method as Example 18.

The solid dispersion was mixed with colloidal silicon dioxide. Microcrystalline cellulose, lactose monohydrate, and croscarmellose sodium are added to the mixture and blending is continued. The mixture is then milled. After magnesium stearate is mixed with the milled mixture, core tablets are compressed on a tablet press. The tablet was filmcoated by using filmcoating machine.

Example 22: Solubility Test

Enzalutamide and the polymer were dissolved in 2 mL of 50% acetone and 50% USP 6.8 buffer. The polymer was used each of hydroxypropylmethylcellulose 2910 (TC-5E, Shin-Etsu Chemical Co., Ltd.), hydroxypropylmethylcellulose 2910 (TC-5R, Shin-Etsu Chemical Co., Ltd.), polyvinylpyrrolidone(Kollidon, BASF), copolyvidone (Kollidon VA-64, BASF), hydroxypropylmethylcellulose acetate succinate(HPMCAS-MG,Shin-Etsu Chemical Co.,Ltd) and was dissolved in 500 mL of a second fluid for disintegrating test used in a dissolution test described in the Japanese Pharmacopoeia fifteenth edition. For comparison, 2 mL of 50% acetone and 50% USP 6.8 buffer dispersed enzalutamide without such polymers was prepared.

To each vessel, 2 mL of a solution of enzalutamide was added, and the solubility of enzalutamide was measured after 5 minitues. The test was carried out using 900 mL of a USP phosphate buffer (pH 6.8) as a test solution.

Each solubility is shown in Table 17.

Example 23: Dissolution Test

Figure 3:
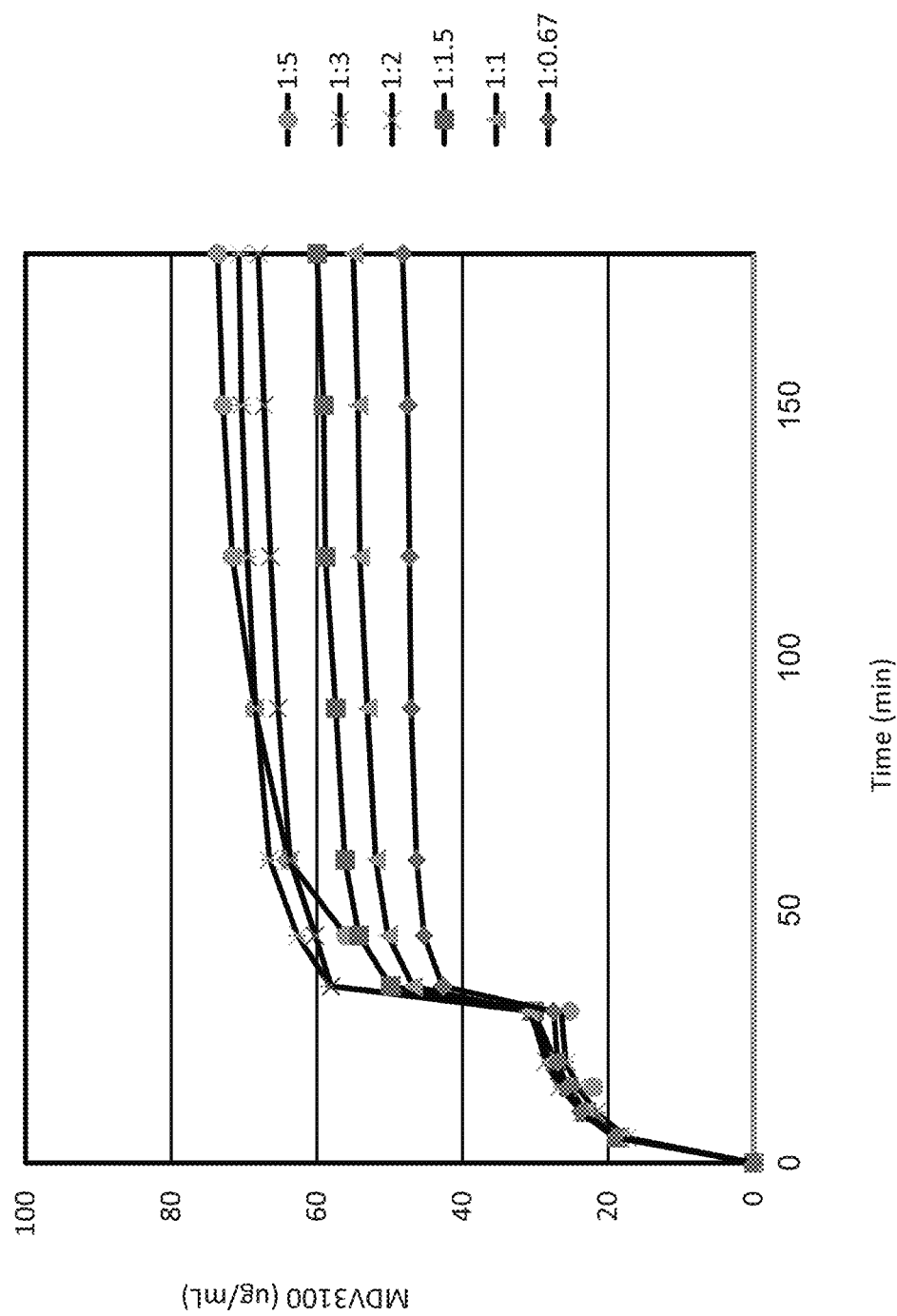
FIG. 3 is a dissolution profile of the solid dispersions obtained by Example 17 (1:3), 18 (1:2), 19 (1:1.5), 20 (1:1), and 21 (1:0.67) in Example 23.
Figure 4:
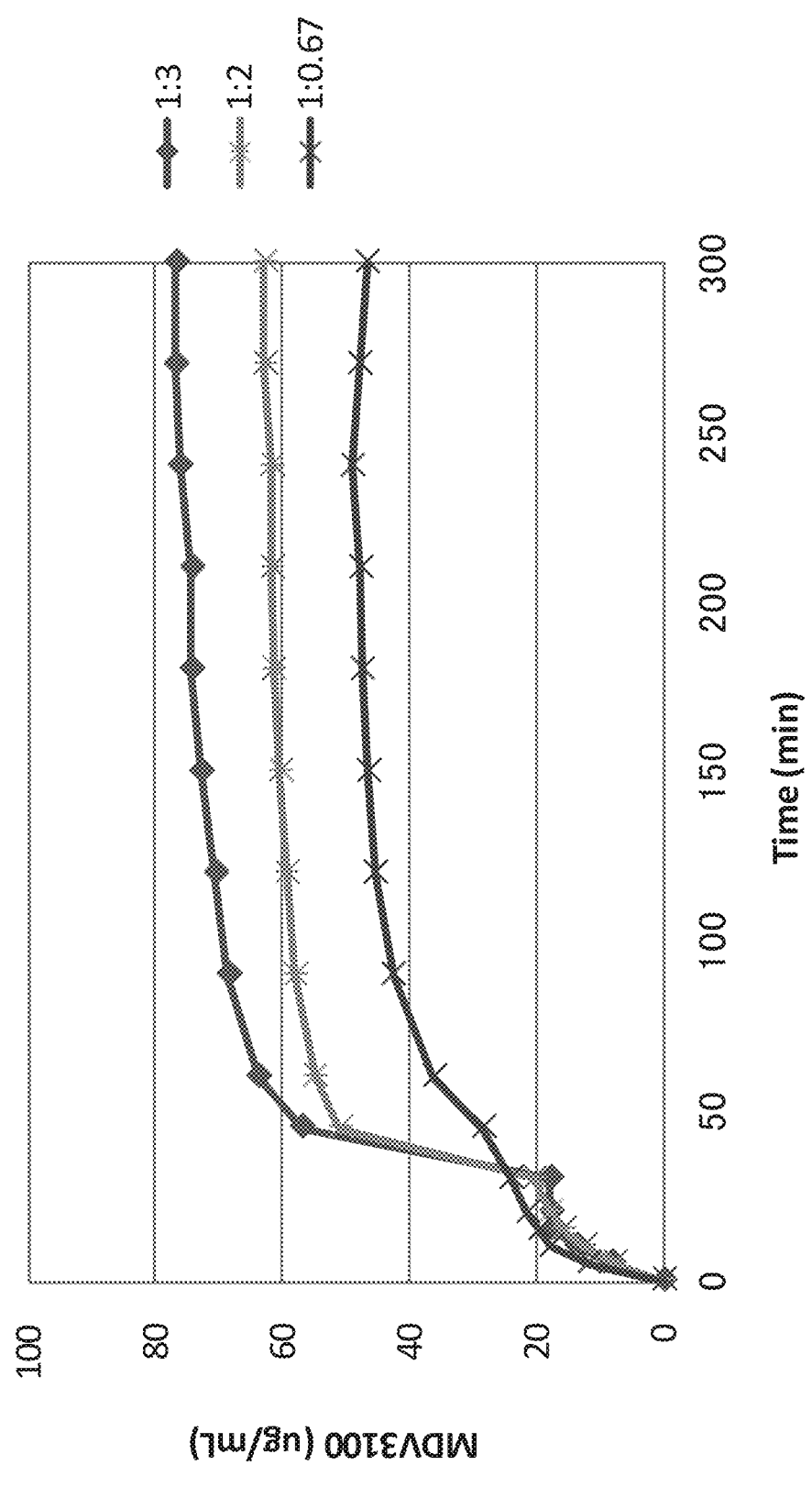
FIG. 4 is a dissolution profile of the tablets obtained by Example 16 (1:3), 18 (1:2), and 21 (1:0.67) in Example 23.

A drug release property from each of the solid dispersion prepared in Examples 1 to 6 or each of the tablet prepared in Examples 1, 3 and 6 was evaluated by a liquid-replacement dissolution test, in which a paddle method (50 rpm) was started using 300 mL of 0.03N hydrochloric acid (pH1.2), and the liquid conditions for the dissolution test were changed to pH6.8 and 900 mL 30 minutes after the beginning of the USP 34-NF 29. The drug release property was evaluated. The dissolution profiles of the enzalutamide from the solid dispersion and the tablet are shown in FIG. 3, FIG. 4, respectively.

Example 24: Evaluation of Dissolution Stability

Figure 5:
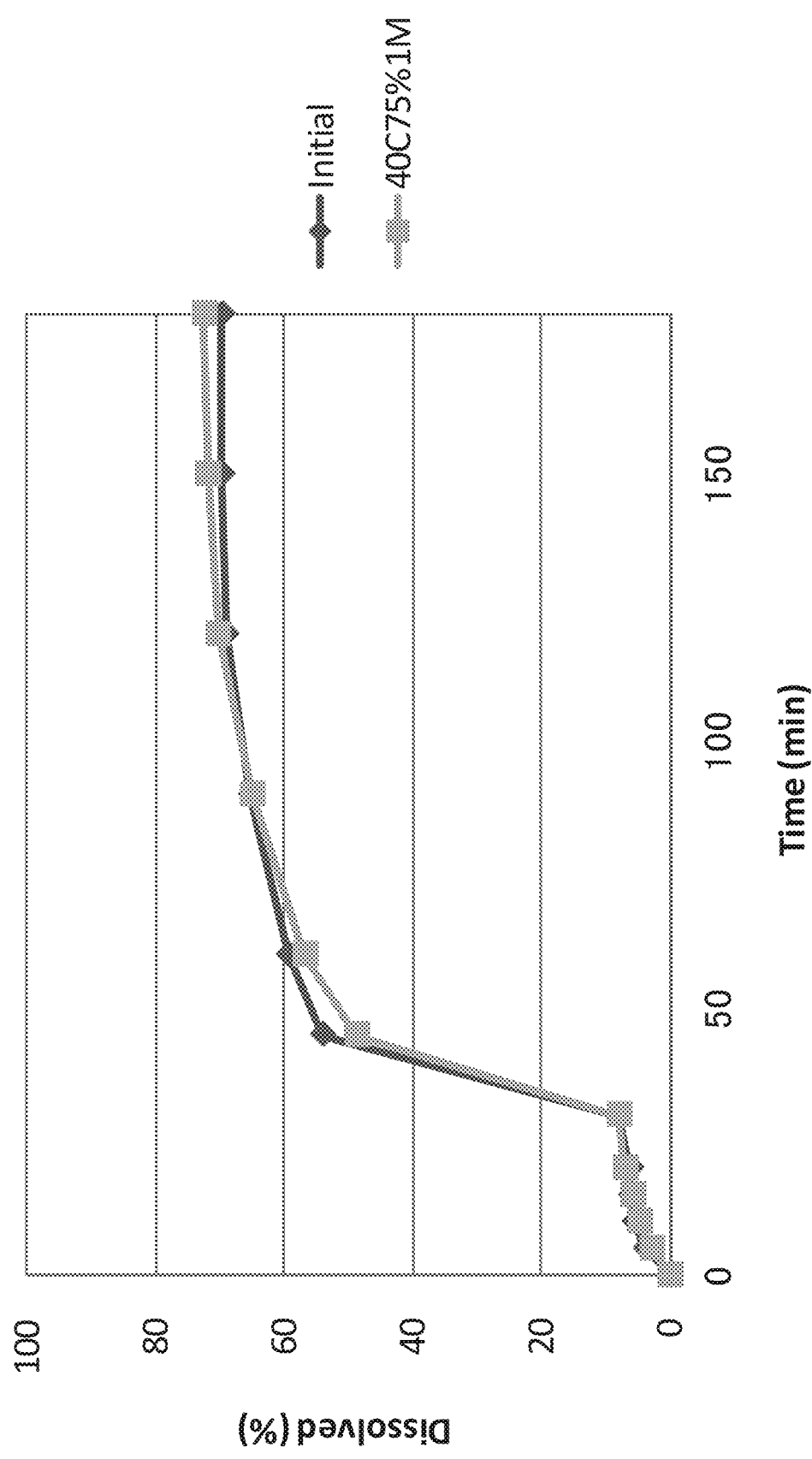
FIG. 5 is a dissolution profile of the initial tablet obtained by Example 17 and the tablet stored at 40° C. and 75% relative humidity for 1 month in Example 24.

The tablet obtained in Example 17 was subjected to a dissolution test to study their dissolution immediately after formulation (at the start of storage) and after storage at 40° C. and 75% relative humidity for 1 month. The dissolution test was accomplished by the paddle method described the United States Pharmacopoeia. A liquid-replacement dissolution test, in which a paddle method (50 rpm) was started using 300 mL of 0.03N hydrochloric acid (pH1.2), and the liquid conditions for the dissolution test were changed to pH6.8 and 900 mL 30 minutes after the beginning of the USP 34-NF 29. The drug release property was evaluated. The dissolution profile is shown in FIG. 5.

Example 25: Dog Absorption Test

The tablets prepared in Examples 16, 18, and 21 and a soft capsule for control were orally administered to dogs. The formulation of the soft capsule is shown in Table 18. Percentage of blood exposure of enzalutamide compared to the soft capsule, % AUC and % $C_{max}$, were evaluated.

The test formulations were administered with 50 mL water to dogs had been fasted over night. The test formulations were used one tablet in case of the tablet comprised 160 mg enzalutamide (Example 21), two tablets in case of the tablet comprised 80 mg enzalutamide (Example 16 and 17), or 4 capsules comprised 40 mg enzalutamide for control.

After orally administered the test formulations, blood samples were collected with time. A drug concentration in the plasma (ng/mL) was measured and calculated maximum drug concentration(Cmax) and AUC for 168 hr (AUC0-168 h: ng*h/mL). The dogs adjusted acid condition in the stomach were used in this test on the assumption of healthy individuals.

% AUC and % Cmax of each formulation are shown in Table 19.

TABLE 17

| polymer | solubility (μg/mL) |
|---|---|
| hydroxypropylmethylcellulose 2910 (TC-5E) | 42.7 |
| hydroxypropylmethylcellulose 2910 (TC-5R) | 39.2 |
| polyvinylpyrrolidone | 40.1 |
| copolyvidone | 47.4 |
| hydroxypropylmethylcellulose acetate succinate | 31.1 |
| without polymer | 29.0 |

TABLE 18

| | soft capsule |
|---|---|
| enzalutamide | 40.000 |
| caprylocaproyl polyoxylglycerides | 904.96 |
| BHA | 0.946 |
| BHT | 0.095 |
| total (mg) | 946.0 |

TABLE 19

| | Dog PK results | |
|---|---|---|
| | % Cmax | % AUC |
| Example 6 | 102 | 99 |
| Example 8 | 92 | 84 |
| Example 21 | 72 | 70 |
| Soft Capsule | 100 | 100 |

Example 26: X-Ray Analysis

The solid dispersions prepared in Examples 16 and 18, and crystalline enzalutamide were evaluated for crystallinity using X rays. In addition, the initial tablet prepared in Example 17 and the tablet after stored at 40° C. and 75% relative humidity for 1 month in Test Example 18.

Figure 7A:
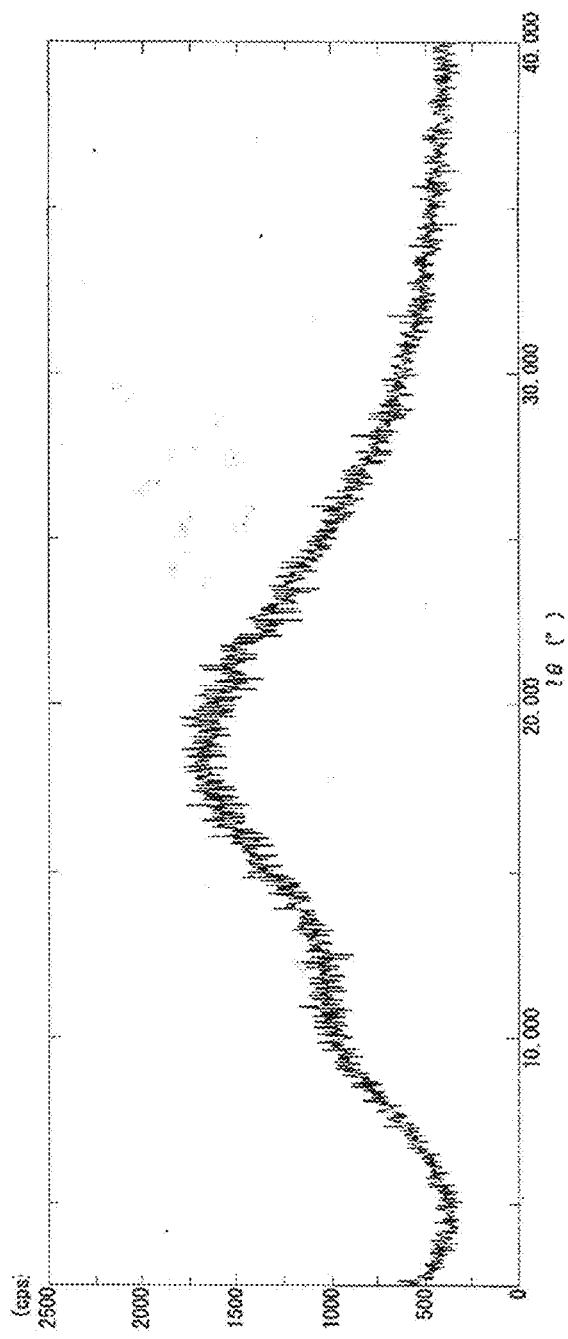
FIG. 7A and FIG. 7B are X-ray diffraction spectra of the solid dispersion which was prepared in Example 17 and stored at 40° C. and 75% relative humidity for 1 month in Example 26.
Figure 7B:
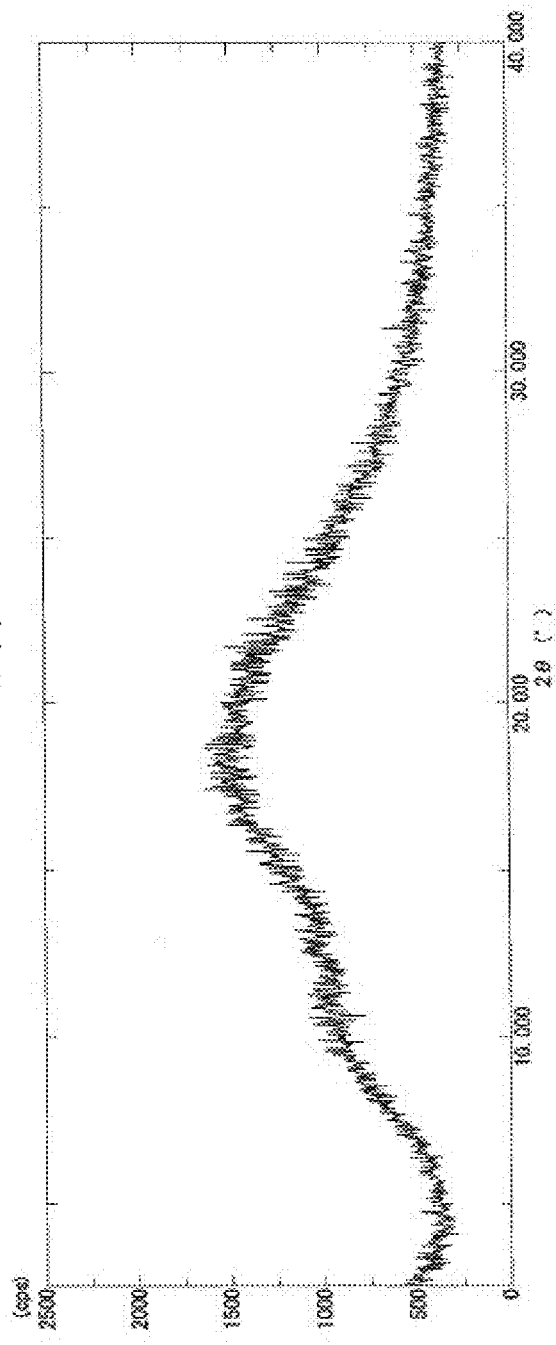

As shown in FIG. 6, the solid dispersions prepared in Examples 16 and 18 were amorphous. As shown in FIG. 7, the tablet obtained by storing the solid dispersion prepared in Example 17 at 40° C. and 75% relative humidity for 1 month in Test Example 19 was also amorphous.

The invention claimed is:

1. A pharmaceutical composition comprising a solid dispersion consisting essentially of amorphous enzalutamide and hydroxypropyl methylcellulose acetate succinate.

2. The pharmaceutical composition according to claim 1, wherein the solid dispersion is a spray-dried dispersion.

3. A pharmaceutical composition comprising a solid dispersion consisting essentially of amorphous enzalutamide and hydroxypropyl methylcellulose acetate succinate, wherein the solid dispersion is a spray-dried dispersion, and wherein the amorphous enzalutamide remains amorphous following storage of the spray-dried dispersion at 40° C. and 75% relative humidity for 1 month.

4. A tablet comprising the pharmaceutical composition according to claim 2.

5. The tablet according to claim 4, wherein the amount of amorphous enzalutamide is 80 mg.

6. The tablet according to claim 4 further comprising croscarmellose sodium and magnesium stearate.

7. A tablet comprising a pharmaceutical composition comprising:
  a solid dispersion consisting essentially of amorphous enzalutamide and hydroxypropyl methylcellulose acetate succinate, wherein the solid dispersion is a spray-dried dispersion,; and
  croscarmellose sodium and magnesium stearate, wherein the croscarmellose sodium is 6% to 10% of the total tablet weight.

* * * * *